US009833445B2

(12) United States Patent
DeWitt

(10) Patent No.: US 9,833,445 B2
(45) Date of Patent: *Dec. 5, 2017

(54) 5-DEUTERO-2,4-THIAZOLIDINEDIONE DERIVATIVES AND COMPOSITIONS COMPRISING AND METHODS OF USING THE SAME

(71) Applicant: DeuteRx, LLC, Andover, MA (US)

(72) Inventor: Sheila DeWitt, Auburn, NH (US)

(73) Assignee: DEUTERX, LLC, Andover, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/226,240

(22) Filed: Aug. 2, 2016

(65) Prior Publication Data

US 2017/0049762 A1 Feb. 23, 2017

Related U.S. Application Data

(63) Continuation of application No. 14/616,317, filed on Feb. 6, 2015, now Pat. No. 9,416,117, which is a continuation of application No. 14/211,905, filed on Mar. 14, 2014, now Pat. No. 8,969,581.

(60) Provisional application No. 61/786,118, filed on Mar. 14, 2013.

(51) Int. Cl.
C07D 213/72 (2006.01)
A61K 31/4439 (2006.01)
C07D 417/12 (2006.01)
C07D 277/34 (2006.01)
C07B 59/00 (2006.01)

(52) U.S. Cl.
CPC ........ A61K 31/4439 (2013.01); C07B 59/002 (2013.01); C07D 277/34 (2013.01); C07D 417/12 (2013.01)

(58) Field of Classification Search
CPC .................................................. A61K 31/4439
USPC ........................................................ 546/304
See application file for complete search history.

(56) References Cited

U.S. PATENT DOCUMENTS

| 4,421,865 | A | 12/1983 | Shen |
| 4,687,777 | A | 8/1987 | Meguro et al. |
| 5,149,820 | A | 9/1992 | Borretzen et al. |
| 5,441,971 | A | 8/1995 | Sohda et al. |
| 6,221,335 | B1 | 4/2001 | Foster |
| 6,334,997 | B1 | 1/2002 | Foster et al. |
| 6,432,993 | B1 | 8/2002 | Fujita et al. |
| 6,440,710 | B1 | 8/2002 | Keinan et al. |
| 6,603,008 | B1 | 8/2003 | Ando et al. |
| 6,706,746 | B2 | 3/2004 | Fujita et al. |
| 7,517,990 | B2 | 4/2009 | Ito et al. |
| 8,067,450 | B2 | 11/2011 | Colca et al. |
| 8,236,786 | B2 | 8/2012 | Finch et al. |
| 8,263,631 | B2 | 9/2012 | Fujiwara et al. |
| 8,389,556 | B2 | 3/2013 | Colca et al. |
| 8,722,710 | B2 | 5/2014 | Czarnik |
| 8,969,581 | B2 | 3/2015 | DeWitt |
| 9,123,444 | B2 | 9/2015 | Subramaniam et al. |
| 9,416,117 | B2 | 8/2016 | DeWitt |
| 2003/0181494 | A1 | 9/2003 | Neogi et al. |
| 2004/0253180 | A1 | 12/2004 | Foster et al. |
| 2007/0082929 | A1 | 4/2007 | Gant et al. |
| 2007/0197695 | A1 | 8/2007 | Potyen et al. |
| 2009/0028868 | A1 | 1/2009 | Fujiwara et al. |
| 2009/0076093 | A1 | 3/2009 | Czarnik |
| 2009/0082405 | A1 | 3/2009 | Czarnik |
| 2012/0015982 | A1 | 1/2012 | Colca et al. |
| 2014/0221369 | A1 | 8/2014 | DeWitt |
| 2014/0243377 | A1 | 8/2014 | Czarnik |
| 2014/0275180 | A1 | 9/2014 | DeWitt |
| 2015/0284346 | A1 | 10/2015 | DeWitt |
| 2016/0331737 | A1 | 11/2016 | DeWitt et al. |

FOREIGN PATENT DOCUMENTS

| EP | 1628646 B1 | 7/2010 |
| WO | WO-95/26325 A2 | 10/1995 |
| WO | WO-99/18081 A1 | 4/1999 |
| WO | WO-03/033494 A1 | 4/2003 |
| WO | WO-03/059271 A2 | 7/2003 |
| WO | WO-2004/073622 A2 | 9/2004 |
| WO | WO-2005/058827 A1 | 6/2005 |
| WO | WO-2006/064826 A1 | 6/2006 |
| WO | WO-2006/083781 A1 | 8/2006 |
| WO | WO-2006/126673 A1 | 11/2006 |
| WO | WO-2007/007656 A1 | 1/2007 |
| WO | WO-2007/100027 A1 | 9/2007 |
| WO | WO-2007/109024 A2 | 9/2007 |
| WO | WO-2007/136129 A1 | 11/2007 |
| WO | WO-2008/099944 A1 | 8/2008 |
| WO | WO-2010/015818 A1 | 2/2010 |
| WO | WO-2010/150014 A1 | 12/2010 |
| WO | WO-2011/017244 A1 | 2/2011 |
| WO | WO-2011/065420 A1 | 6/2011 |

(Continued)

OTHER PUBLICATIONS

Tanis, J Med Chem. 1996, 39(26) 5053-5066.*
Aithal et al., "Randomized, Placebo-Controlled Trial of Pioglitazone in Nondiabetic Subjects with Nonalcoholic Steatohepatitis," *Gastroenterology* (2008), vol. 135, pp. 1176-1184.
Baillie, T., "The Use of Stable Isotopes in Pharmacological Research", Pharmacological Reviews, 33(2):81-132 (1981).
Bharatam et al., "Rapid Racemization in Thiazolidinediones: A Quantum Chemical Study", J. Phys. Chem. A., 108:3784-3788 (2004).

(Continued)

*Primary Examiner* — Nizal Chandrakumar
(74) *Attorney, Agent, or Firm* — Goodwin Procter LLP

(57) ABSTRACT

The invention provides 5-deuterium-enriched 2,4-thiazolidinediones (e.g., 5-[4-[2-(5-ethyl-2-pyridyl)-2-oxoethoxy]benzyl]-5-deutero-thiazolidine-2,4-dione), deuterated derivatives thereof, stereoisomers thereof, pharmaceutically acceptable salt forms thereof, and methods of treatment using the same.

42 Claims, 6 Drawing Sheets

(56) References Cited

FOREIGN PATENT DOCUMENTS

| WO | WO-2011/098799 A2 | 8/2011 |
|---|---|---|
| WO | WO-2011/098801 A1 | 8/2011 |
| WO | WO-2011/100685 A2 | 8/2011 |
| WO | WO-2011/133441 A2 | 10/2011 |
| WO | WO-2013/011402 A1 | 1/2013 |
| WO | WO-2013/056232 A2 | 4/2013 |
| WO | WO-2013/134626 A1 | 9/2013 |
| WO | WO-2014/121036 A1 | 8/2014 |
| WO | WO-2014/152843 A1 | 9/2014 |
| WO | WO-2015/109037 A1 | 7/2015 |

OTHER PUBLICATIONS

Boettcher et al., "Meta-analysis: Pioglitazone Improves Liver Histology and Fibrosis in Patients with Non-Alcoholic Steatohepatitis," Aliment Pharmacol Ther, vol. 35, pp. 66-75 (2012).
Browne, T., "Stable Isotope Techniques in Early Drug Development: An Economic Evaluation", J Clin Pharmacol, 38:213-220 (1998).
Buteau, K., "Deuterated Drugs: Unexpectedly Nonobvious?", 10 J. High Tech. L. 22 (2009) (53 pages).
Cabrero et al., "Peroxisome Proliferator-Activated Receptors and the Control of Inflammation", Current Drug Target—Inflammation & Allergy, 1(3):243-248 (2002) (Abstract).
Chalasani et al., "The Diagnosis and Management of Non-Alcoholic Fatty Liver Disease: Practice Guideline by the American Association for the Study of Liver Diseases, American College of Gastroenterology, and the American Gastroenterological Association," Hepatology (2012), vol. 55, No. 6, pp. 2005-2023.
Chen et al., "Insulin Resistance and Metabolic Derangements in Obese Mice Are Ameliorated by a Novel Peroxisome Proliferator-activated Receptor γ-sparing Thiazolidinedione", J. Biol. Chem., 287(28):23537-23548 (2012).
Cherrah et al., "Study of Deuterium Isotope Effects on Protein Binding by Gas Chromatography/Mass Spectrometry. Caffeine and Deuterated Isotopomers", Biomedical and Environmental Mass Spectrometry, 14:653-657 (1987).
Colca et al., "Identification of a Mitochondrial Target of Thiazolidinedione Insulin Sensitizers (mTOT)-Relationship to Newly Identified Mitochondrial Pyruvate Carrier Proteins", PLOS One, 8(5)e61551:1-10 (2013).
Dyck et al., "Effects of Deuterium Substitution on the Catabolism of β-Phenylethylamine: An In Vivo Study", J Neurochem, 46(2):399-404 (1986).
Federal Register "Examination guidelines" p. 1-34, Sep. 1, 2010.
Federico, et al., "Focus on emerging drugs for the treatment of patients with non-alcoholic fatty liver disease," World Journal of Gastroenterology (2014), vol. 20, pp. 16841-16857.
Foster, A., "Deuterium Isotope Effects in the Metabolism of Drugs and Xenobiotics: Implications for Drug Design", Adv. Drug Res., 14:2-40 (1985).
Gouyette, A., "Synthesis of Deuterium-labelled Elliptinium and its Use in Metabolic Studies", Biomedical and Environmental Mass Spectrometry, 15:243-247 (1988).
Harbeson et al., "Deuterium in Drug Discovery and Development", Annual Reports in Med Chem, 46:403-417 (2011).
Honma et al.,"The Metabolism of Roxatidine Acetate Hydrochloride", Drug Metabolism and Disposition, 15(4):551-559 (1987).
Hutt et al., "The Chiral Switch: The Development of Single Enantiomer Drugs from Racemates", ACTA Facult. Pharm. Univ. Comenianae, 50:7-23 (2003).
International Search Report and Written Opinion for International Application No. PCT/US2015/011493 dated Mar. 6, 2015 (10 pages).
International Search Report and Written Opinion for PCT/US2014/014083 dated May 16, 2014 (12 pages).
International Search Report and Written Opinion for PCT/US2014/027943 dated Jul. 10, 2014 (15 pages).

Jamali et al., "Investigation of racemisation of the enantiomers of glitazone drug compounds at different pH using chiral HPLC and chiral CE", J. Pharm. and Biomed. Anal., 46:82-87 (2008).
Kaufman et al., "Deuterium Enrichment of Vitamin A at the C20 Position Slows the Formation of Detrimental Vitamin A Dimers in Wild-type Rodents", J. Biol. Chem., 286(10):7958-7965 (2011).
Kawaguchi et al., "Pioglitazone prevents hepatic steatosis, fibrosis, and enzyme-altered lesions in rat liver cirrhosis induced by a choline-deficient L-amino acid-defined diet," Biochemical and Biophysical Research Communications, (2004), vol. 315, pp. 187-195.
Kawai et al., "Hydrogen-Rich Water Prevents Progression of Nonalcoholic Steatohepatitis and Accompanying Hepatocarcinogenesis in Mice," Hepatology (2012), vol. 56, pp. 912-921.
Leclercq et al., "Intrahepatic insulin resistance in a murine model of steatohepatitis: effect of PPARγ agonist pioglitazone," Laboratory Investigation(2007), vol. 87, pp. 56-65.
Lin et al., "Dose effect of thiazolidinedione on cancer risk in type 2 diabetes mellitus patients: a six-year population-based cohort study," Journal of Clinical Pharmacy and Therapeutics (2014), vol. 39, pp. 354-360.
Lomonaco et al., "Nonalcoholic Fatty Liver Disease: Current Issues and Novel Treatment Approaches," Drugs, vol. 73, pp. 1-14 (2013).
Lutchman et al., "The Effects of Discontinuing Pioglitazone in Patients with Nonalcoholic Steatohepatitis," Hepatology (2007) vol. 46, pp. 424-429.
Maltais et al., "In Vitro and In Vivo Isotope Effects with Hepatitis C Protease Inhibitors: Enhanced Plasma Exposure of Deuterated Telaprevir versus Telaprevir in Rats", J. Med. Chem. (2009) vol. 52, pp. 7993-8001.
Mislow et al., "A Note on Steric Isotope Effects. Conformational Kinetic Isotope Effects in the Racemization of 9,10-Dihydro-4,5-Dimethylphenanthrene", J. Am. Chem. Soc. 85:1199-1200 (1963).
Motani et al., "INT131: A Selective Modulator of PPARγ", J. Mol. Biol., 386:1301-1311 (2009).
Nassar et al., "Improving the decision-making process in the structural modification of drug candidates: enhancing metabolic stability", Drug Discovery Today, 9(23):1020-1028 (2004).
Nelson et al., "The Use of Deuterium Isotope Effects to Probe the Active Site Properties, Mechanism of Cytochrome P450-Catalyzed Reactions, and Mechanisms of Metabolically Dependent Toxicity", Drug Metabolism and Disposition, 31(12):1481-1498 (2003).
Parks et al., "Differential Activity of Rosiglitazone Enantiomers at PPARγ", Bioorg. & Medicinal Chem. Letters, 8:3657-3658 (1998).
Pfutzner et al., "Pioglitazone: update on an oral antidiabetic drug with antiatherosclerotic effects", Expert Opin. Pharmacother., 8(12):1985-1998 (2007).
Pieniaszek, Jr., et al., "Moricizine Bioavailability via Simultaneous, Dual, Stable Isotope Administration: Bioequivalence Implications", J Clin Pharmacol, 39:817-825 (1999).
Promrat et al., "A Pilot Study of Pioglitazone Treatment for Nonalcoholic Steatohepatitis," Hepatology (2004), vol. 39, pp. 188-196.
Sanyal et al., "A Pilot Study of Vitamin E Versus Vitamin E and Pioglitazone for the Treatment of Nonalcoholic Steatohepatitis," Clinical Gastroenterology and Hepatology (2004), vol. 2, pp. 1107-1115.
Sanyal et al., "Pioglitazone, Vitamin E, or Placebo for Nonalcoholic Steatohepatitis," The New England Journal of Medicine, (2010) vol. 362, pp. 1675-1685.
Shao et al., "Derivatives of tramadol for increased duration of effect", Bioorg. Med. Chem. Lett. 16:691-694 (2006).
Smith et al., "Non-Alcoholic Fatty Liver Disease," Critical Reviews in Clinical Laboratory Sciences, vol. 48, pp. 97-113 (2011).
Sohda et al., "Studies on Antidiabetic Agents. XII.1) Synthesis and Activity of the metabolites of (±)-5-[p-[2-(5-Ethyl-2-pyridyl)ethoxy]benzyl]-2,4-thiazolidinedione (Pioglitazone)", Chem. Pharm. Bull., 43(12):2168-2172 (1995).
Uto et al., "The peroxisome proliferator-activated receptor-γ agonist, pioglitazone, inhibits fat accumulation and fibrosis in the livers of rats fed a choline-deficient, L-amino acid-defined diet," Hepatology Research (2005), vol. 32, pp. 235-242.
Van Wagner et al., "The role of insulin-sensitizing agents in the treatment of nonalcoholic steatohepatitis," Ther Adv Gastroenterol (2011) vol. 4, pp. 249-263.

(56) References Cited

OTHER PUBLICATIONS

Wiberg, K., "The Deuterium Isotope Effect", Chem. Rev., 55(4):713-743 (1955).

Yarnell, A., "Heavy-Hydrogen Drugs Turn Heads, Again", Chemical & Engineering News, 87(25):36-39 (2009).

Zhang et al., "Thiazolidinediones Improve Hepatic Fibrosis in Rats with Non-Alcoholic Steatohepatitis by Activating the Adenosine Monophosphate-Activated Protein Kinase Signalling Pathway," Clinical and Experimental Pharmacology and Physiology, vol. 39, pp. 1026-1033 (2012).

Zhu Y. et al., "Deuterated Clopidogrel Analogues as a New Generation of Antiplatelet Agents", ACS Med. Chem. Lett. 2013, vol. 4, Issue 3, pp. 349-352.

Dorwald, "Side Reactions in Organic Synthesis," Wiley, pp. IX of preface pp. 1-15 (2005).

Colca et al., "Identification of a Novel Mitochondrial Protein ("mitoNEET") Cross-linked Specifically by a Thiazolidinedione Photoprobe", Am J Physiol Endrocrinol Metab, (2004), 286(2):E252-60.

Divakaruni et al., "Thiazolidinediones are Acute, Specific Inhibitors of the Mitochondrial Pyruvate Carrier," Proc Natl Acad Sci USA, (2013), 110(14):5422-7.

Foster, "Deuterium Isotope Effects in Studies of Drug Metabolism," Trends Pharmacol Sci, (1984), 5:524-7.

Jaakkola et al., "Montelukast and Zafirlukast do not Affect the Pharmacokinetics of the CYP2C8 Substrate Pioglitazone," Eur J Clin Pharmacol, (2006), 62(7):503-9.

Jaakkola et al., "Pioglitazone is Metabolized by CYP2C8 and CYP3A4 in vitro. Potential for Interactions with CYP2C8 Inhibitors," Basic Clin Phamacol Toxicol, (2006), 99(1):44-51.

Stedman and Barclay, "Review Article: Comparison of the Pharmacokinetics, Acid Suppression and Efficacy of Proton Pump Inhibitors," Aliment Pharmacol Ther, (2000), 14(8):963-78.

Tilg and Moschen, "Evolving Therapies for Non-Alcoholic Steatohepatitis," Expert Opin Drug Discov, (2014), 9(6):687-96.

Haskins, N. J. "The Application of Stable Isotopes in Biomedical Research," *Biomedical Mass Spectrometry*, 9 (7), 1982, 269-277.

Kushner, D.J. et al. "Pharmacological Uses and Perspectives of Heavy Water and Deuterated Compounds," *Canadian Journal of Physiology and Pharmacology*, 1999, 77(2), 79-88.

Tonn et al. "Simultaneous Analysis of Diphenhydramine and a Stable Isotope Analog ($^2H_{10}$)Diphenydramine Using Capillary Gas Chromatography with Mass Selective Detection in Biological Fluids from Chronically Instrumented Pregnant Ewes," *Biological Mass Spectrometry*, 22 (11) 1993, 633-642.

Wolen, R. L. "The application of stable isotopes to studies of drug bioavailability and bioequivalence," *J. Clin. Pharm.* (1986) vol. 26, pp. 419-424.

Shao, L. & Hewitt, M.C. "The Kinetic Isotope Effect in the Search for Deuterated Drugs," *Drug News& Perspectives*, 2010, vol. 23, No. 6, pp. 398-404.

Yamamoto et al., "Synthesis and Configurational Stability of (S)- and (R)-Deuteriothalidomides", Chem. Pharm. Bull. 58(1):110-112 (2010).

Fisher et al., "The complexities inherent in attempts to decrease drug clearance by blocking sites of CYP-mediated metabolism", *Curr. Opin. Drug Disc. Dev.*, 9(1):101-109 (2006).

Wade, D., "Deuterium isotope effects on noncovalent interactions between molecules", *Chemico-Biological Interactions*, 117 p. 191-217 (1999).

Woo, H.Y, et al., "Rescue therapy with adefovir in decompensated liver cirrhosis patients with lamivudine-resistant hepatitis B virus", Clinical and Molecular Hepatology, 2014, vol. 20, pp. 168-176.

Peng, S., et al., "An Updated Meta-Analysis of Randomized Controlled Trials Assessing the Effect of Sorafenib in Advanced Hepatocellular Carcinoma", PLOS ONE, 2014, vol. 9, No. 12, pp. e112530.

Farlow, M. R., et al., "Comparing Clinical Profiles in Alzheimer's Disease and Parkinson's Disease Dementia", Dementia and Geriatric Cognitive Disorders Extra, 2013, vol. 3, pp. 281-290.

Griebeler, M.L., et al, "Pharmacologic interventions for painful diabetic neuropathy: An umbrella systematic review and comparative effectiveness network meta-analysis", Annals of Internal Medicine, 2014, vol. 161, No. 9, pp. 639-649.

Zhou, C. et al., "Discovery of 5-aryloxy-2,4-thiazolidinediones as potent GPR40 agonists", Bioorg. Med. Chem. Lett. 2010, vol. 20, No. 3, pp. 1298-1301.

Christiansen, E. et al., "Identification of a Potent and Selective Free Fatty Acid Receptor 1 (FFA1/GPR40) Agonist with Favorable Physicochemical and in Vitro ADME Properties", J. Med. Chem. (2011) vol. 54, No. 19, pp. 6691-6703.

Hardy, T. et al. "Nonalcoholic fatty liver disease: new treatments," *Curr. Opin. Gastroenterology* (2015) vol. 31, No. 3, pp. 175-183.

Chalasani et al., "The Diagnosis and Management of Non-Alcoholic Fatty Liver Disease: Practice Guideline by the American Gastroenterological Association, American Association for the Study of Liver Diseases, and American College of Gastroenterology," *Gastroenterology* (2012), vol. 142, No. 7, pp. 1592-1609.

U.S. Appl. No. 15/088,472, Deuterium-Enriched Pioglitazone, filed Apr. 1, 2016.

U.S. Appl. No. 15/109,533, Methods of Treating Neurological, Metabolic, and Other Disorders Using Enantiopure Deuterium-Enriched Pioglitazone, filed Oct. 7, 2016.

* cited by examiner

5-DEUTERO-2,4-THIAZOLIDINEDIONE DERIVATIVES AND COMPOSITIONS COMPRISING AND METHODS OF USING THE SAME

RELATED APPLICATIONS

This application is a continuation of U.S. patent application Ser. No. 14/616,317, filed Feb. 6, 2015, which is a continuation of U.S. patent application Ser. No. 14/211,905, filed Mar. 14, 2014, now U.S. Pat. No. 8,969,581, which claims the benefit of and priority to U.S. Provisional Patent Application Ser. No. 61/786,118, filed Mar. 14, 2013, the contents of each of which are hereby incorporated by reference.

BACKGROUND

Compounds such as 5-[4-[2-(5-ethyl-2-pyridyl)-2-oxoethoxy]benzyl]-2,4-thiazolidinedione (Formula A below) (mitoglitazone (MSDC-0160)) and 5-{4-[2-(3-methoxyphenyl)-2-oxoethoxy]benzyl}-1,3-thiazolidine-2,4-dione (Formula B below) are currently being studied for activity against diabetes, hypertension, inflammatory diseases, and other disorders.

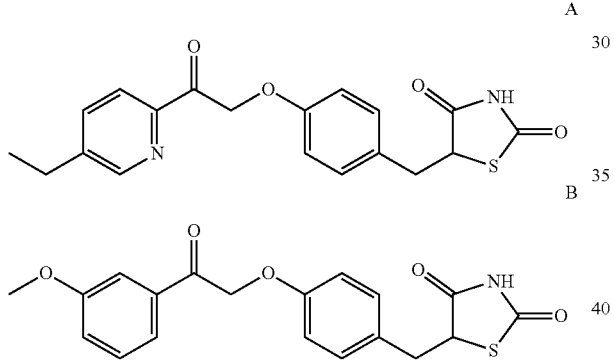

The above compounds are described in U.S. Pat. Nos. 5,441,971, 8,067,450, and 8,389,556 and International Patent Application Publication No. WO 2011/017244; the contents of which are hereby incorporated by reference.

The compounds of Formulae A and B, because of their asymmetric carbon atom in position 5 on the 2,4-thiazolidinedione ring, are a racemic mixture of R and S enantiomers. The hydrogen at the 5-position is acidic due to the presence of the adjacent carbonyl moiety, thereby making it difficult to prevent racemization of the two stereoisomers and difficult to determine if one of the stereoisomers is superior to the other.

Despite the clinical interest in mitoglitazone, there is still a need for agents with improved properties for treating medical disorders such as diabetes, hypertension, and inflammatory diseases. The invention provides new compounds that are resistant to racemization at their stereogenic center, and are useful in the treatment of various medical disorders.

SUMMARY

The invention provides deuterium-enriched 2,4-thiazolidinedione compounds, pharmaceutical compositions, and methods of treating medical disorders using the deuterium-enriched compounds and pharmaceutical compositions containing such deuterium-enriched compounds. The deuterium-enriched compounds contain deuterium enrichment at the chiral center of the thiazolidine-2,4-dione moiety and optionally in other locations in the compound. One aspect of the invention provides the deuterium-enriched compounds in enantiomerically pure form. The deuterium-enriched compounds described herein provide a better therapeutic agent than non-deuterated versions of these compounds.

Accordingly, one aspect of the invention provides 5-deuterium-enriched 2,4-thiazolidinediones (e.g., 5-[4-[2-(5-ethyl-2-pyridyl)-2-oxoethoxy]benzyl]-5-deutero-thiazolidine-2,4-dione) and stereoisomers and pharmaceutically acceptable salts thereof. The deuterium-enriched compounds are described by generic and specific chemical formulae. One aspect of the invention provides a deuterium-enriched compound represented by formula I:

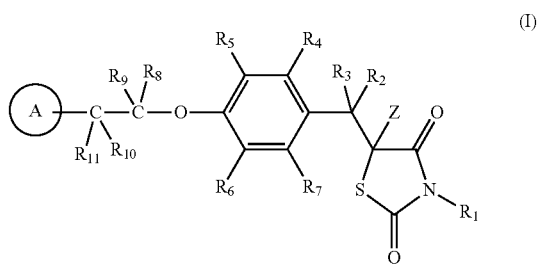

or a pharmaceutically acceptable salt or stereoisomer thereof; wherein the variables are as defined in the detailed description. A more specific embodiment of the invention provides a deuterium-enriched compound represented by formula XI:

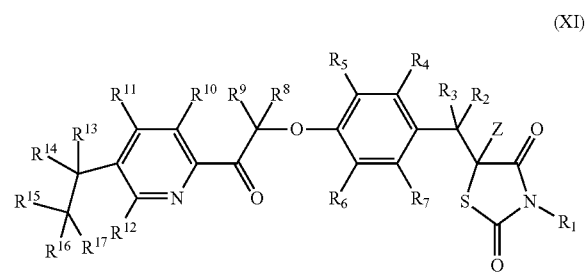

or a stereoisomer or pharmaceutically acceptable salt form thereof; wherein the variables are as defined in the detailed description. Another more specific embodiment of the invention provides a deuterium-enriched compound having the formula:

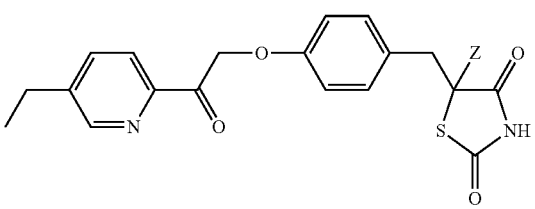

or a stereoisomer or pharmaceutically acceptable salt form thereof, wherein variable Z is as defined in the detailed description.

Yet another more specific embodiment of the invention, providing enantiomerically enriched compounds, is the compound

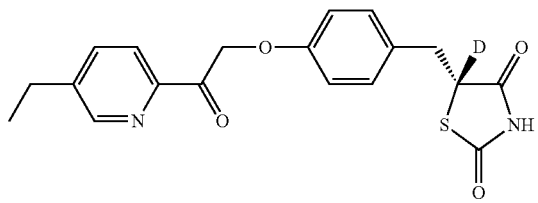

or a pharmaceutically acceptable salt form thereof, wherein the compound has an enantiomeric excess of at least 90%, or more preferably at least 95%.

Yet another more specific embodiment of the invention, providing enantiomerically enriched compounds, is the compound

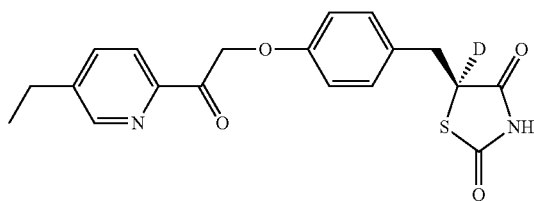

or a pharmaceutically acceptable salt form thereof, wherein the compound has an enantiomeric excess of at least 90%, or more preferably at least 95%.

Another aspect provided herein is a pharmaceutical composition comprising a pharmaceutically acceptable carrier and at least one of the deuterium-enriched compounds described herein.

Also provided herein are methods for treating medical disorders. Exemplary methods comprise administering to a patient in need thereof a therapeutically effective amount of a deuterium-enriched compound described herein to treat the medical disorder. Exemplary medical disorders include, for example, cancer, a neurological disorder, a respiratory disorder, a metabolic disorder, an inflammatory disorder, a cardiovascular disorder, and a dermatological disorder. The compounds are typically administered to a patient in the form of a pharmaceutical composition. Particularly preferred medical disorders include, for example, diabetes (e.g., Type II diabetes), Alzheimer's disease, Parkinson's disease, and other forms of cognitive impairment.

A more specific embodiment of the therapeutic methods involves treating diabetes (e.g., Type I diabetes, Type II diabetes, insulin resistance, and inadequate glucose tolerance) and other metabolic inflammation mediated diseases (e.g., insulin resistance associated with metabolic syndrome including dyslipidemia, and central obesity). Another more specific embodiment of the therapeutic methods involves treating other inflammatory diseases (e.g., rheumatoid arthritis, lupus, myasthenia gravis, vasculitis, Chronic Obstructive Pulmonary Disease (COPD), nonalcoholic fatty liver disease (NAFLD), nonalcoholic steatohepatitis (NASH), and inflammatory bowel disease) and neurodegenerative diseases (e.g., Alzheimer's disease, Parkinson's disease, and multiple sclerosis).

Another aspect provided herein is deuterium-enriched compounds for use in therapy. Still another aspect provided herein is the use of deuterium-enriched compounds for the manufacture of a medicament.

These and other aspects, which will become apparent during the following detailed description, have been achieved by the inventor's discovery of 5-deuterium-enriched 2,4-thiazolidinediones.

DETAILED DESCRIPTION

Figure 1:
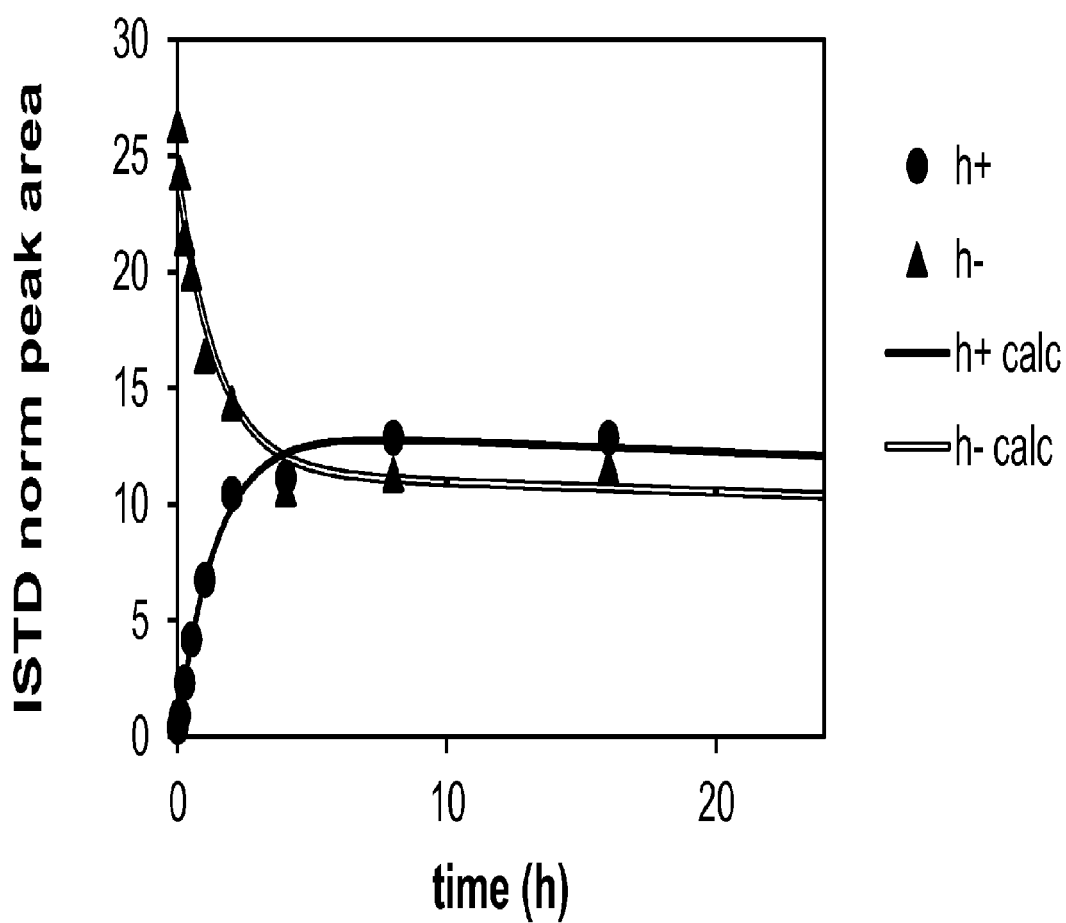
FIG. 1 is a graph showing in vitro stability data for (−)-5-({p-[2-(5-ethylpyridin-2-yl)-2-oxoethoxy]phenyl}methyl)-1,3-thiazolidine-2,4-dione (designated "h-") in human plasma, as described in Example 3, where the abbreviation "calc" indicates results from fitting experimental data to kinetic differential equations.

Deuterium (D or $^2$H) is a stable, non-radioactive isotope of hydrogen and has an atomic weight of 2.014. Hydrogen naturally occurs as a mixture of the isotopes $^1$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their non-enriched counterparts. Thus, the invention relates to a deuterium-enriched compound or compounds whose enrichment is greater than naturally occurring deuterated molecules.

All percentages given for the amount of deuterium present are mole percentages. Further, when a variable is not accompanied by a definition, the previous definition of the variable controls.

Unless indicated otherwise, when a D is specifically recited at a position or is shown in a formula, this D represents a mixture of hydrogen and deuterium where the amount of deuterium is about 100% (i.e., the abundance of deuterium is from 90% to 100%). In certain aspects, the abundance of deuterium is from 97% to 100%).

The 5-deuterium group (i.e., the Z group (or D)) in the present compounds means that the compounds have been isotopically enriched at the 5-position and are different and distinct from the corresponding non-enriched compounds.

Compound refers to a quantity of molecules that is sufficient to be weighed, tested for its structural identity, and to have a demonstrable use (e.g., a quantity that can be shown to be active in an assay, an in vitro test, or in vivo test, or a quantity that can be administered to a patient and provide a therapeutic benefit).

I. EXEMPLARY DEUTERIUM-ENRICHED COMPOUNDS

One aspect of the invention provides a deuterium-enriched compound of formula I or a stereoisomer or pharmaceutically acceptable salt form thereof:

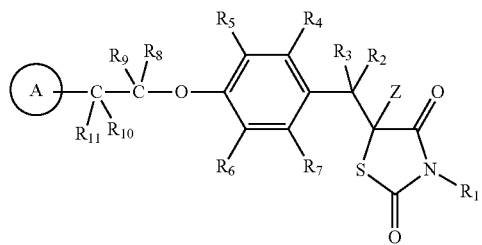

I wherein:

$R^1$, $R^2$, $R^3$, $R^4$, $R^7$, $R^6$, $R^7$, $R^8$, $R^9$, and $R^{10}$ are independently selected from H and D;

Z is H or D, provided that the abundance of deuterium in Z is at least 30%;

ring A is phenyl or a monocyclic heteroaryl having 1-3 heteroatoms selected from N, O, or S; and ring A is substituted with 1-2 $R^A$ $R^A$, at each occurrence, is independently selected from: H, D, halo, optionally substituted aliphatic, and optionally substituted alkoxy;

$R^{11}$ is selected from: H, D, halo, OH, OD, and optionally substituted aliphatic;

alternatively, $R^{10}$ and $R^{11}$ are taken together with the carbon to which they are attached to form a carbonyl;

alternatively, when $CR^{10}R^{11}$ is C(O) or $CH_2$, then ring A is substituted with 1 $R^B$;

$R^B$ is selected from: $CH_3C(O)$—, $CH_3CH(OR)$—, and —$CH_2CO_2H$;

R is selected from H, D, and $C_{1-8}$ acyl; and a hydrogen atom present anywhere in the compound of Formula I is optionally replaced by D.

In certain embodiments, $R^{11}$ is selected from: halo, OH, OD, and optionally substituted aliphatic; or alternatively, $R^{10}$ and $R^{11}$ are taken together with the carbon to which they are attached to form a carbonyl; or alternatively, when $CR^{10}R^{11}$ is C(O) or $CH_2$, then ring A is substituted with 1 $R^B$ In another aspect, the invention provides a deuterium-enriched compound of formula I or a stereoisomer or pharmaceutically acceptable salt form thereof:

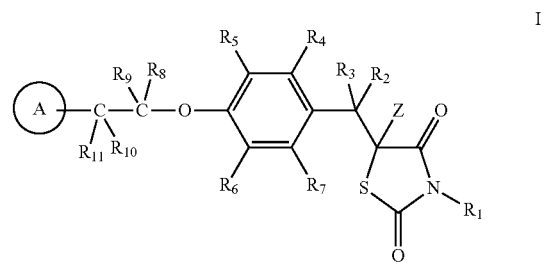

I wherein:

$R^1$, $R^2$, $R^3$, $R^4$, $R^5$, $R^6$, $R^7$, $R^8$, $R^9$, and $R^{10}$ are independently selected from H and D;

Z is H or D, provided that the abundance of deuterium in Z is at least 30%;

ring A is phenyl or a monocyclic heteroaryl having 1-3 heteroatoms selected from N, O, or S; and ring A is substituted with 1-2 $R^A$ $R^A$, at each occurrence, is independently selected from: H, D, halo, $C_{1-6}$ alkyl optionally substituted with 1-3 halo, and $C_{1-6}$ alkoxy optionally substituted with 1-3 halo;

$R^{11}$ is selected from: H, D, halo, OH, OD, and $C_{1-6}$ alkyl optionally substituted with 1-2 groups independently selected from OH, OD, and halo;

alternatively, $R^{10}$ and $R^{11}$ are taken together with the carbon to which they are attached to form a carbonyl;

alternatively, when $CR^{10}R^{11}$ is C(O) or $CH_2$, then ring A is substituted with 1 $R^B$;

$R^B$ is selected from: $CH_3C(O)$—, $CH_3CH(OR)$—, and —$CH_2CO_2H$;

R is selected from H, D, and $C_{1-8}$ acyl; and a hydrogen atom present anywhere in the compound of Formula I is optionally replaced by D.

In certain embodiments, $R^{11}$ is selected from: halo, OH, OD, and $C_{1-6}$ alkyl optionally substituted with 1-2 groups independently selected from OH, OD, and halo; or alternatively, $R^{10}$ and $R^{11}$ are taken together with the carbon to which they are attached to form a carbonyl; or alternatively, when $CR^{10}R^{11}$ is C(O) or $CH_2$, then ring A is substituted with 1 $R^B$ In certain embodiments, the deuterium-enriched compound is one of the generic formulae described herein wherein the abundance of deuterium in Z is selected from: (a) at least 40%, (b) at least 50%, (c) at least 60%, (d) at least 70%, (e) at least 80%, (f) at least 90%, (g) at least 95%, (h) at least 97%, and (i) about 100%. Additional examples of the abundance of deuterium in Z include 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100%.

Deuterium-enriched compounds characterized according to their stereochemical purity are provided. The stereochemical purity of compounds having one stereocenter can be characterized as enantiomeric excess (ee). Enantiomeric excess can be calculated using the formula:

$$ee(\%)=(R-S)/(R+S)*100$$

where R and S are the amounts of (R) and (S) enantiomers in the mixture.

For compounds having two or more stereocenters, the stereochemical purity (sp) refers to the percentage of 1 of the 4 or more possible stereoisomers being present. For a compound with two stereocenters, the stereomeric purity can be calculated using the formula:

$$sp(\%)=\% \text{ Isomer } 1-(\% \text{ Isomer } 2+\% \text{ Isomer } 3+\% \text{ Isomer } 4)$$

where % Isomer # is the weight (e.g., mole) % of one of the isomers in the mixture.

In another aspect, the invention provides a compound having an enantiomeric excess of at least 5%. Exantiomeric excess, with respect to the C—Z carbon (i.e., 5-carbon of the thiazolidinedione), refers only to the stereomeric purity around this carbon, regardless of whether or not additional stereocenters are present in the compound.

In another aspect, the invention provides deuterium-enriched compounds wherein the enantiomeric excess is selected from: (a) at least 10%, (b) at least 20%, (c) at least 30%, (d) at least 40%, (e) at least 50%, (f) at least 60%, (g) at least 70%, (h) at least 80%, (i) at least 90%, (j) at least 95%, (k) at least 97%, (l) at least 98%, and (m) at least 99%. Additional examples of the stereoisomeric purity include an enantiomeric excess of at least 10, 11, 12, 13, 14, 15, 16, 17 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

In another aspect, the invention provides a compound having stereomeric purity of at least 5%.

In another aspect, the invention provides deuterium-enriched compounds wherein the stereomeric purity is selected from: (a) at least 10%, (b) at least 20%, (c) at least 30%, (d) at least 40%, (e) at least 50%, (f) at least 60%, (g) at least 70%, (h) at least 80%, (i) at least 90%, (j) at least 95%, (k) at least 97%, (l) at least 98%, and (m) at least 99%. Additional examples of the stereoisomeric purity include at least 10, 11, 12, 13, 14, 15, 16, 17 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

In certain embodiments, the enantiomer present in abundance (i.e., present in a greater quantity than the other enantiomer) is the (−)-enantiomer. In certain embodiments, the enantiomer present in abundance is the (+)-enantiomer. In certain embodiments, the enantiomer present in abundance is the (R)-enantiomer. In certain embodiments, the enantiomer present in abundance is the (S)-enantiomer.

In another aspect, the invention provides a deuterium-enriched compound of formula Ia or Ib or a pharmaceutically acceptable salt form thereof:

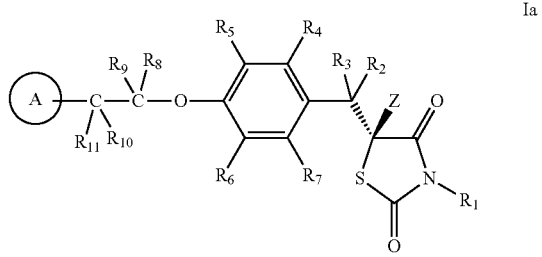

Ia

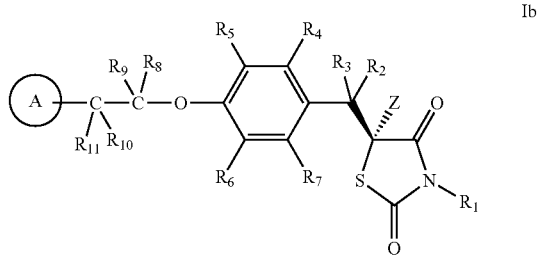

Ib wherein the variables are as defined above for formula I.

In another aspect, the invention provides a deuterium-enriched compound of formula Ia or Ib or a pharmaceutically acceptable salt form thereof:

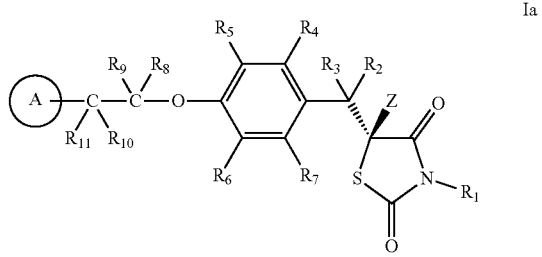

Ia

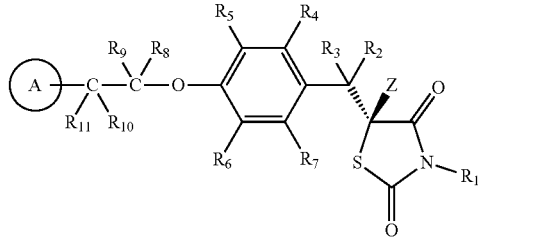

Ib wherein the variables are as defined above for formula I; and the compound of formula Ia or Ib has an enantiomeric excess, with respect to the C—Z carbon, of at least 5%.

In another aspect, $R^4$ is an optionally substituted $C_{1-6}$ aliphatic. Examples of this group include an optionally substituted straight or branched $C_{1-6}$ alkyl, an optionally substituted straight or branched $C_{2-6}$ alkenyl, and an optionally substituted straight or branched $C_{2-6}$ alkynyl. Other examples of $R^4$ include: H, methyl, ethyl, propyl, isopropyl, butyl, tert-butyl, pentyl, and hexyl.

In another aspect, $R^{11}$ is selected from H, halo, hydroxy, and an optionally substituted $C_{1-6}$ aliphatic. Examples of this group include an optionally substituted straight or branched $C_{1-6}$ alkyl, an optionally substituted straight or branched $C_{2-6}$ alkenyl, and an optionally substituted straight or branched $C_{2-6}$ alkynyl. Other examples include a $C_{1-6}$ aliphatic optionally substituted with 1-2 hydroxy or halo and a $C_{1-6}$ alkyl optionally substituted with hydroxy. Further examples of $R^{11}$ include a group selected from: methyl, ethyl, propyl, isopropyl, butyl, tert-butyl, pentyl, or hexyl, each of which is optionally substituted with hydroxy. Additional examples include a group selected from methyl and ethyl, each of which is substituted with hydroxy.

In another aspect, ring A is a monocyclic 5-6 membered heteroaryl having 1-3 heteroatoms selected from N, O, or S that is substituted with —$CH_2$—$R^A$. Examples of ring A include a ring selected from: furanyl, thiophenyl, pyrrolyl, pyridinyl, pyrazolyl, 1,3,4-thiadiazolyl, 1,3,5-triazinyl, pyrazinyl, pyrimidinyl, pyridazinyl, isoxazolyl, or isothiazolyl, each of which is substituted with $R^A$. In an additional example, ring A is a pyridinyl that is substituted with $R^A$.

In another aspect, the invention provides a deuterium-enriched compound of formula II or a stereoisomer or pharmaceutically acceptable salt form thereof:

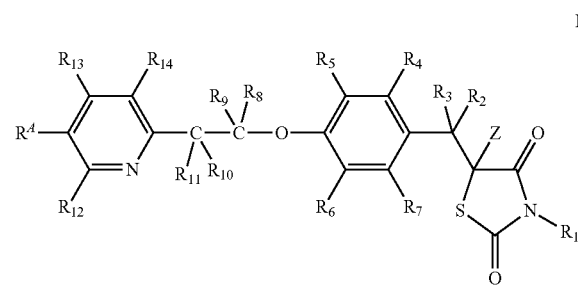

II wherein:
$R^1$, $R^2$, $R^3$, $R^4$, $R^5$, $R^6$, $R^7$, $R^8$, $R^9$, $R^{10}$, $R^{12}$, $R^{13}$, and $R^{14}$ are independently selected from H and D;
Z is H or D, provided that the abundance of deuterium in Z is at least 30%;
$R^A$ is selected from $CH_3$, and $C_{1-6}$ alkyl optionally substituted with 1-3 halo;
$R^{11}$ is selected from: H, D, halo, OH, OD, and $C_{1-6}$ alkyl optionally substituted with 1-2 groups independently selected from OH, OD, and halo;
alternatively, $R^{10}$ and $R^{11}$ are taken together with the carbon to which they are attached to form a carbonyl; and
a hydrogen atom present anywhere in the compound of Formula II is optionally replaced by D.

In certain embodiments, $R^{11}$ is selected from: halo, OH, OD, and $C_{1-6}$ alkyl optionally substituted with 1-2 groups independently selected from OH, OD, and halo; or alternatively, $R^{10}$ and $R^{11}$ are taken together with the carbon to which they are attached to form a carbonyl.

In another aspect, the invention provides a deuterium-enriched compound of formula IIIa or IIIb or a pharmaceutically acceptable salt form thereof:

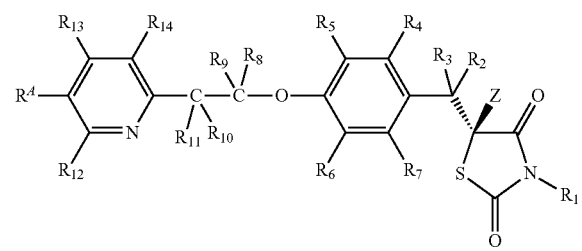

IIa

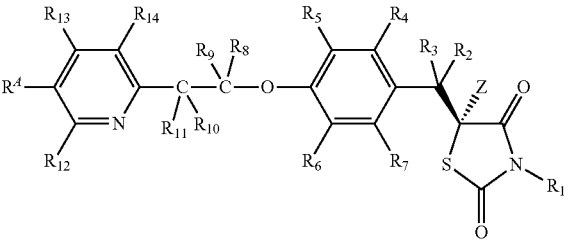

IIb wherein the variables are as defined above for formula II.

In another aspect, the invention provides a deuterium-enriched compound of formula IIIa or IIIb or a pharmaceutically acceptable salt form thereof:

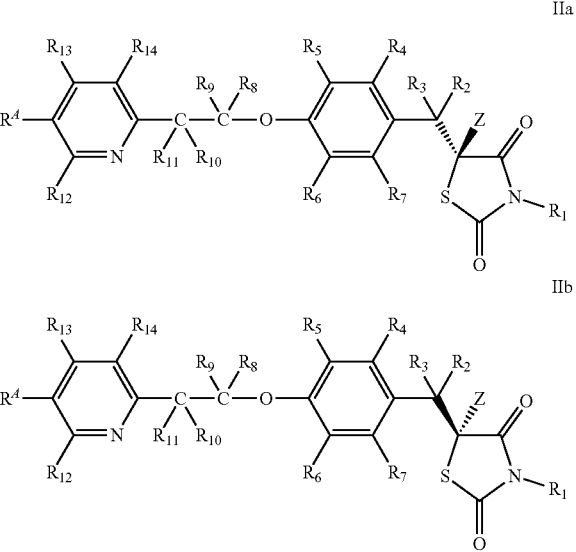

IIa

IIb wherein the variables are as defined above for formula II; and the compound of formula IIa or IIb has an enantiomeric excess, with respect to the C—Z carbon, of at least 5%.

In another aspect, the invention provides a deuterium-enriched compound of formula III or a stereoisomer or pharmaceutically acceptable salt form thereof:

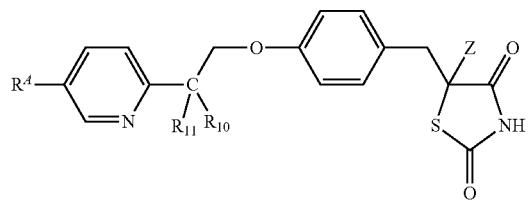

III wherein:
$R^{10}$ is H or D;
Z is H or D, provided that the abundance of deuterium in Z is at least 30%;
$R^A$ is $C_{1-4}$ alkyl optionally substituted with 1-3 halo;
$R^{11}$ is selected from: H, D, halo, OH, OD, and $C_{1-4}$ alkyl optionally substituted with 1-2 groups independently selected from OH, OD, and halo;

alternatively, $R^{10}$ and $R^{11}$ are taken together with the carbon to which they are attached to form a carbonyl; and a hydrogen atom present anywhere in the compound of Formula III is optionally replaced by D.

In certain embodiments, $R^{11}$ is selected from: halo, OH, OD, and $C_{1-4}$ alkyl optionally substituted with 1-2 groups independently selected from OH, OD, and halo; or alternatively, $R^{10}$ and $R^{11}$ are taken together with the carbon to which they are attached to form a carbonyl.

In another aspect, the invention provides a deuterium-enriched compound of formula IIIa or IIIb or a pharmaceutically acceptable salt form thereof:

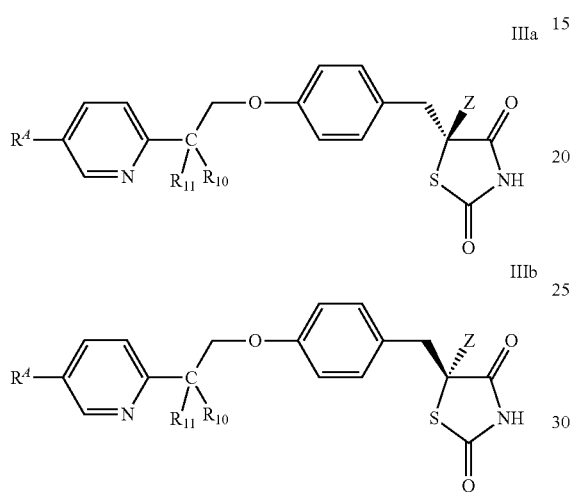

IIIa

IIIb wherein the variables are as defined above for formula III.

In another aspect, the invention provides a deuterium-enriched compound of formula IIIa or IIIb or a pharmaceutically acceptable salt form thereof:

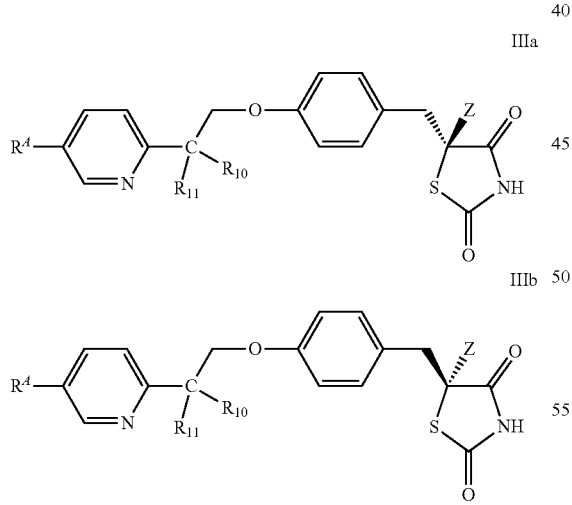

IIIa

IIIb wherein the variables are as defined above for formula III; and the compound of formula IIIa or IIIb has an enantiomeric excess, with respect to the C—Z carbon, of at least 5%.

In another aspect, the invention provides a deuterium-enriched compound of formula IIIc, IIId, IIIe, or IIIf or a pharmaceutically acceptable salt form thereof:

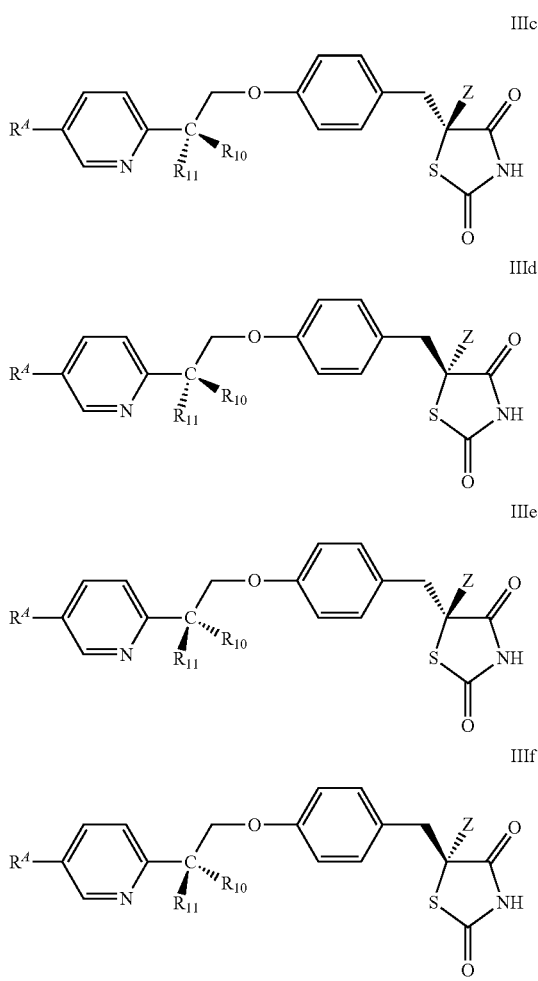

IIIc

IIId

IIIe

IIIf wherein:

$R^{10}$ is H or D;

Z is H or D, provided that the abundance of deuterium in Z is at least 30%;

$R^A$ is $C_{1-4}$ alkyl optionally substituted with 1 halo;

$R^{11}$ is selected from: OH, OD, and $C_{1-4}$ alkyl optionally substituted with 1-2 groups independently selected from OH, OD, and halo; and a hydrogen atom present anywhere in the compound of Formula IIIa-IIIf is optionally replaced by D.

In another aspect, the invention provides a deuterium-enriched compound of formula IIIc, IIId, IIIe, or IIIf or a pharmaceutically acceptable salt form thereof:

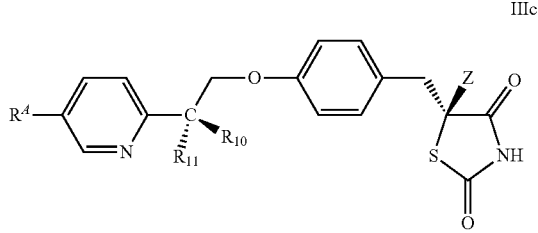

IIIc

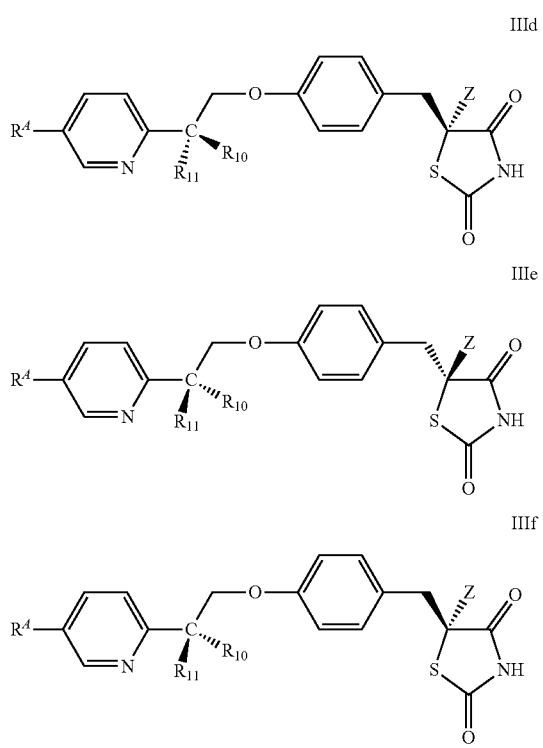

wherein:

R$^{10}$ is H or D;

Z is H or D, provided that the abundance of deuterium in Z is at least 30%;

R$^4$ is C$_{1-4}$ alkyl optionally substituted with 1 halo;

R$^{11}$ is selected from: OH, OD, and C$_{1-4}$ alkyl optionally substituted with 1-2 groups independently selected from OH, OD, and halo;

a hydrogen atom present anywhere in the compound of Formula IIIa-IIIf is optionally replaced by D; and, the compound of formula IIIc, IIId, IIIe, or IIIf has a stereomeric purity of at least 5%.

In another aspect, the invention provides a deuterium-enriched compound, selected from:

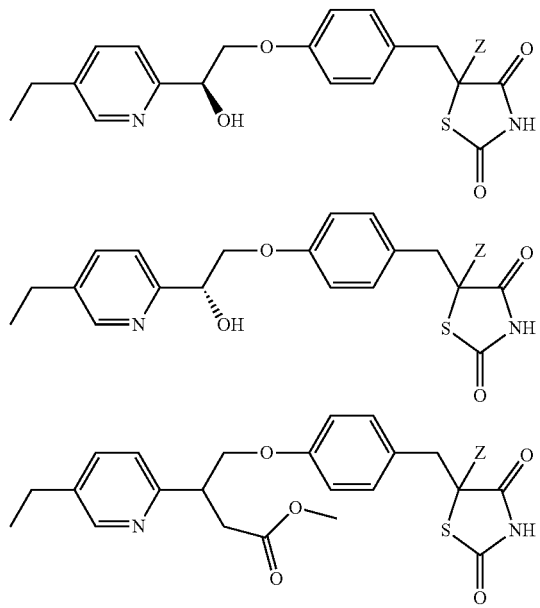

or a stereoisomer or pharmaceutically acceptable salt form thereof; wherein Z is as defined above for formula I. In certain embodiments, the compound is further selected from

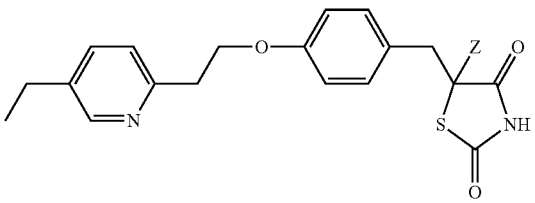

or a stereoisomer or pharmaceutically acceptable salt form thereof. In certain embodiments, the compound is further selected from:

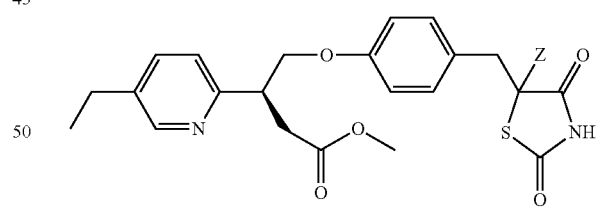

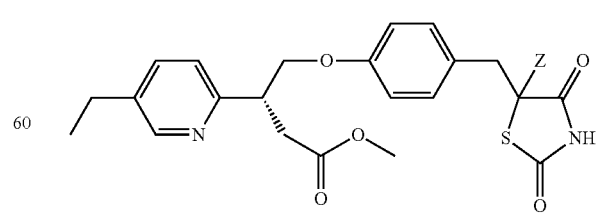

and stereoisomers and pharmaceutically acceptable salt forms thereof.

In another aspect, the invention provides a deuterium-enriched compound, selected from:

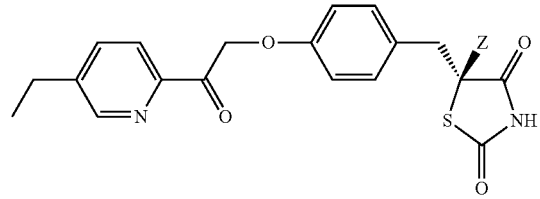 [SMILES: [2H][C@]1(Cc2ccc(OCC(=O)c3ccc(CC)cn3)cc2)SC(=O)NC1=O]

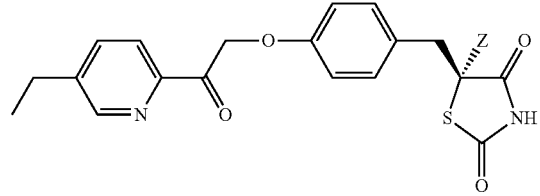

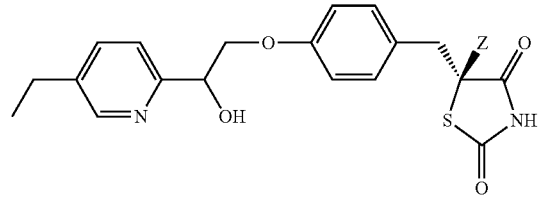

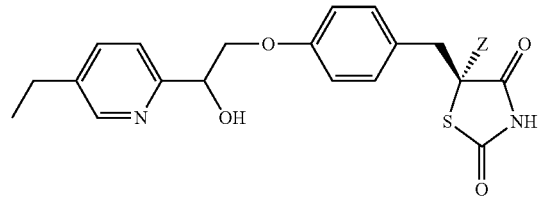

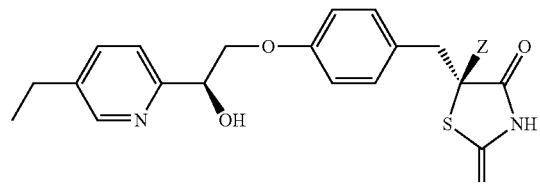

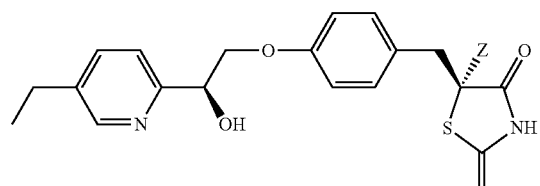

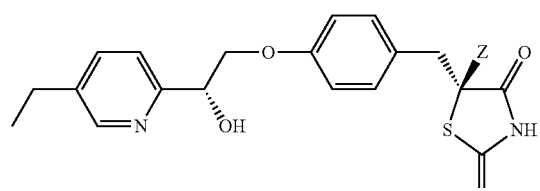

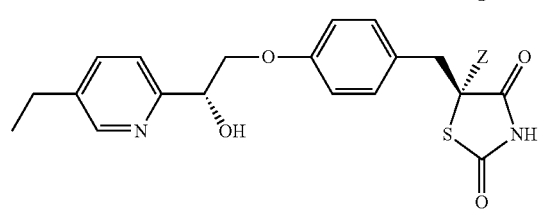

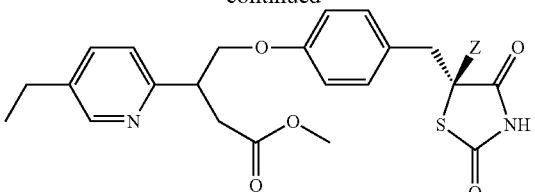

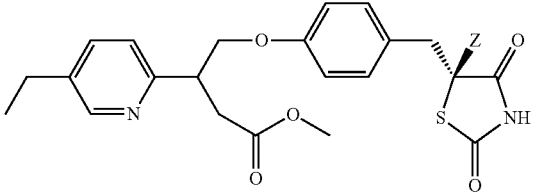

or a pharmaceutically acceptable salt form thereof; wherein Z is as defined above for formula I. In certain embodiments, the compound is further selected from

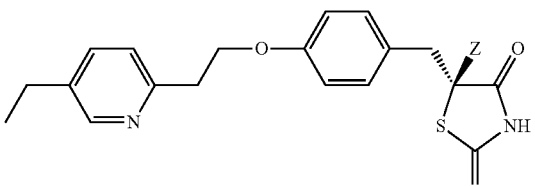

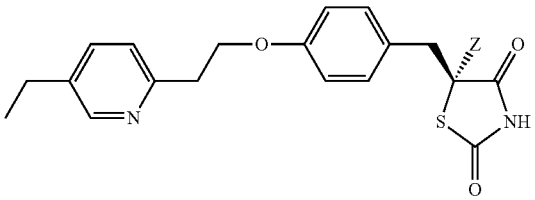

or a pharmaceutically acceptable salt form thereof.

In another aspect, the compounds above have an enantiomeric excess, with respect to the C—Z carbon, of at least 5%.

In another aspect, the invention provides a deuterium-enriched compound of formula IV or a stereoisomer or pharmaceutically acceptable salt form thereof:

IV

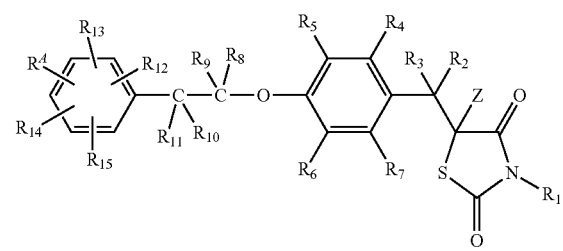

wherein:

$R^1, R^2, R^3, R^4, R^5, R^6, R^7, R^8, R^9, R^{10}, R^{12}, R^{13}, R^{14}$, and $R^{15}$ are independently selected from H and D;

Z is H or D, provided that the abundance of deuterium in Z is at least 30%;

$R^A$ is $C_{1-6}$ alkyl optionally substituted with 1-3 halo;

$R^1$ is selected from: H, D, halo, OH, OD, and $C_{1-6}$ alkyl optionally substituted with 1-2 groups independently selected from OH, OD, and halo;

alternatively, $R^{10}$ and $R^{11}$ are taken together with the carbon to which they are attached to form a carbonyl; and a hydrogen atom present anywhere in the compound of Formula IV is optionally replaced by D.

In another aspect, the invention provides a deuterium-enriched compound of formula IVa or IVb or a pharmaceutically acceptable salt form thereof:

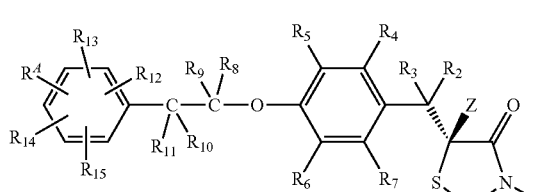

IVa

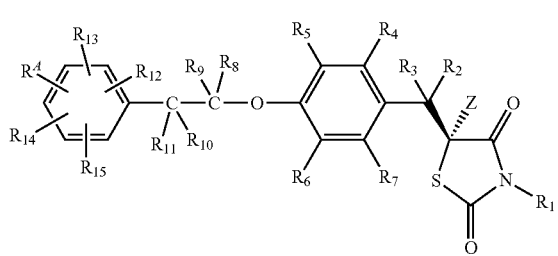

IVb wherein the variables are as defined above for formula IV.

In another aspect, the invention provides a deuterium-enriched compound of formula IVa or IVb or a pharmaceutically acceptable salt form thereof:

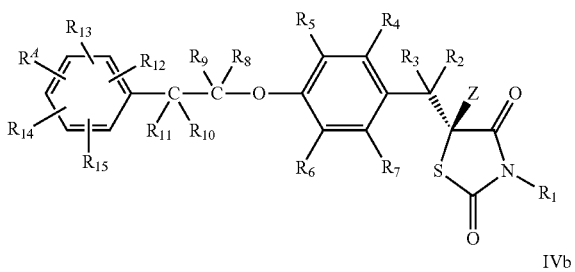

IVa

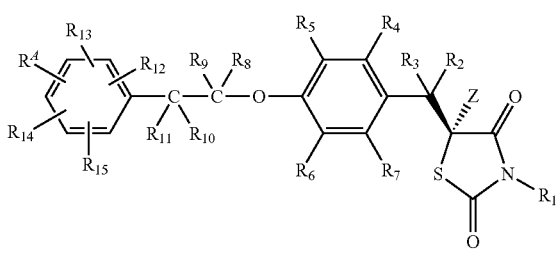

IVb wherein the variables are as defined above for formula IV; and, the compound of formula IVa or IVb has an enantiomeric excess, with respect to the C—Z carbon, of at least 5%.

In another aspect, $R^A$ is H. In another aspect, $R^A$ is halo, such as F or Cl. In another aspect, $R^A$ is an aliphatic optionally substituted with 1-3 halo. In another aspect, $R^A$ is alkoxy (e.g., methoxy, ethoxy, or —O-isopropyl). In another aspect, $R^A$ is alkoxy substituted with 1-3 halo (e.g., —OCHF$_2$ or —OCF$_3$). In another aspect, $R^A$ is independently selected from H, halo, aliphatic, and alkoxy, wherein the aliphatic and alkoxy are optionally substituted with 1-3 halo.

In another aspect, $R^{11}$ is selected from H, halo, hydroxy, and an optionally substituted $C_{1-6}$ aliphatic. Examples of this group include an optionally substituted straight or branched $C_{1-6}$ alkyl, an optionally substituted straight or branched $C_{2-6}$ alkenyl, and an optionally substituted straight or branched $C_{2-6}$ alkynyl. Other examples include a $C_{1-6}$ aliphatic optionally substituted with 1-2 hydroxy or halo and a $C_{1-6}$ alkyl optionally substituted with hydroxy. Further examples of $R^{11}$ include a group selected from: methyl, ethyl, propyl, isopropyl, butyl, tert-butyl, pentyl, or hexyl, each of which is optionally substituted with hydroxy. Additional examples include a group selected from methyl and ethyl, each of which is substituted with hydroxy.

In another aspect, the invention provides a deuterium-enriched compound of formula V or a stereoisomer or pharmaceutically acceptable salt form thereof:

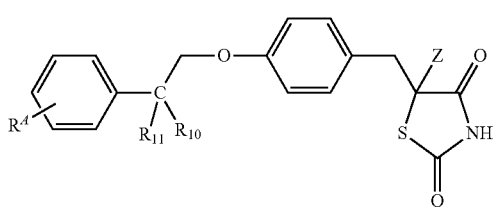

V wherein:

$R^{10}$ is H or D;

Z is H or D, provided that the abundance of deuterium in Z is at least 30%;

$R^A$ is selected from: H, D, halo, $C_{1-4}$ alkyl optionally substituted with 1 halo, and $C_{1-4}$ alkoxy optionally substituted with 1 halo;

$R^{11}$ is selected from: halo, OH, OD, and $C_{1-4}$ alkyl optionally substituted with 1-2 groups independently selected from OH, OD, and halo; and a hydrogen atom present anywhere in the compound of Formula V is optionally replaced by D.

In another aspect, the invention provides a deuterium-enriched compound of formula Va or Vb or a pharmaceutically acceptable salt form thereof:

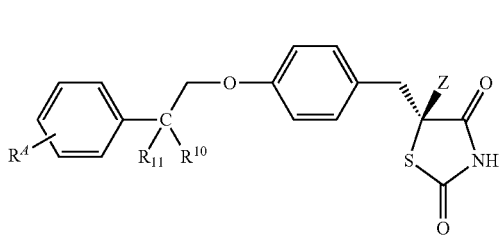

Va

Vb

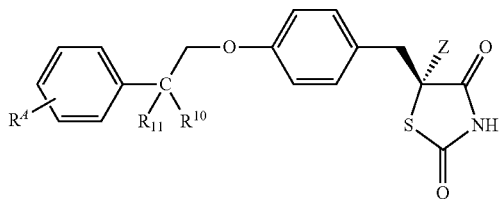

wherein the variables are as defined above for formula V.

In another aspect, the invention provides a deuterium-enriched compound of formula Va or Vb or a pharmaceutically acceptable salt form thereof:

Va

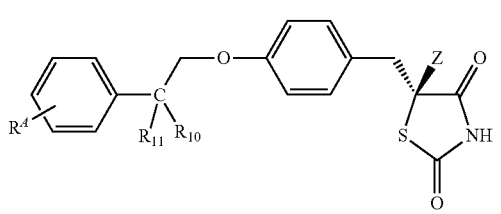

Vb

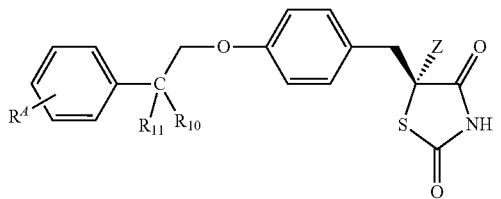

wherein the variables are as defined above for formula V; and, the compound of formula Va or Vb has an enantiomeric excess, with respect to the C—Z carbon, of at least 5%.

In another aspect, the invention provides a deuterium-enriched compound of formula Vc, Vd, Ve, or Vf or a pharmaceutically acceptable salt form thereof:

Vc

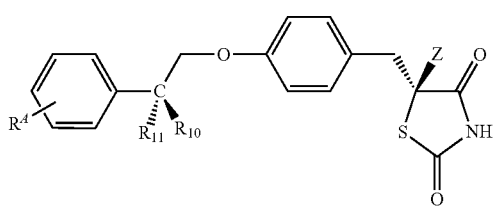

Vd

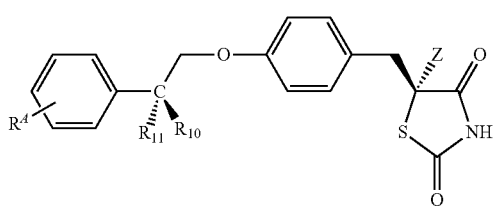

Ve

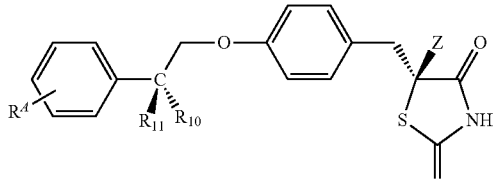

Vf

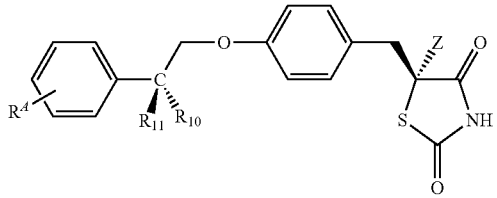

wherein the variables are as defined above for formula V.

In another aspect, the invention provides a deuterium-enriched compound of formula Vc, Vd, Ve, or Vf or a pharmaceutically acceptable salt form thereof:

Vc

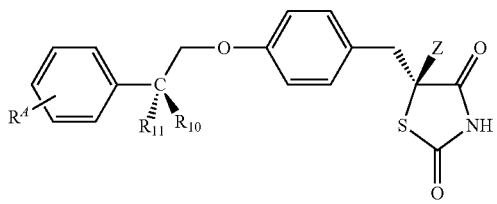

Vd

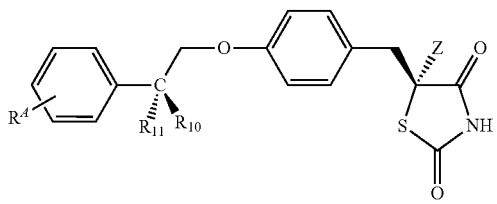

Ve

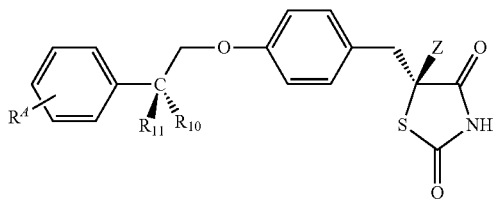

Vf

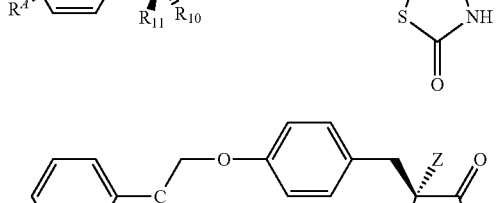

wherein the variables are as defined above for formula V; and the compound of formula Vc, Vd, Ve, or Vf has a stereomeric purity of at least 5%.

In another aspect, the invention provides a deuterium-enriched compound of formula VI or a stereoisomer or pharmaceutically acceptable salt form thereof:

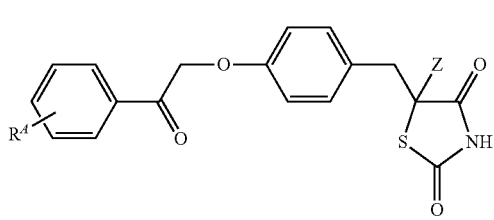

VI wherein:

Z is H or D, provided that the abundance of deuterium in Z is at least 30%;

$R^A$ is selected from: H, D, halo, $C_{1-4}$ alkyl optionally substituted with 1 halo, and $C_{1-4}$ alkoxy optionally substituted with 1 halo; and a hydrogen atom present anywhere in the compound of Formula VI is optionally replaced by D.

In another aspect, the invention provides a deuterium-enriched compound of formula VIa or VIb or a pharmaceutically acceptable salt form thereof:

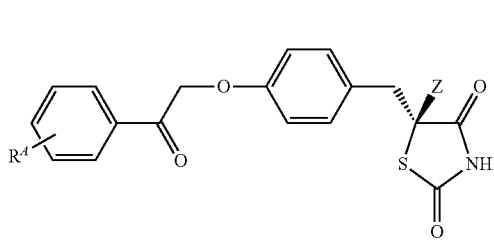

VIa

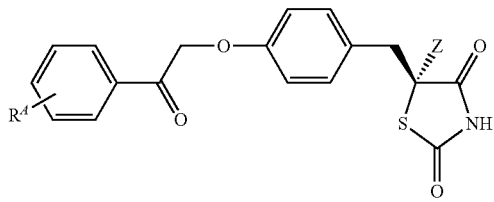

VIb wherein the variables are as defined above for formula VI.

In another aspect, the invention provides a deuterium-enriched compound of formula VIa or VIb or a pharmaceutically acceptable salt form thereof:

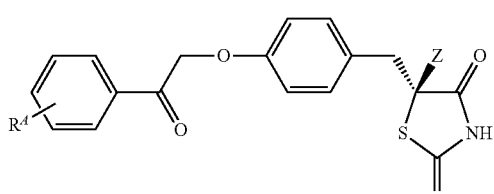

VIa

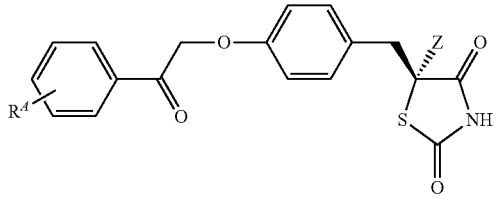

VIb wherein the variables are as defined above for formula VI; and the compound of formula VIa or VIb has an enantiomeric excess, with respect to the C—Z carbon, of at least 5%.

In another aspect, the invention provides a deuterium-enriched compound, selected from:

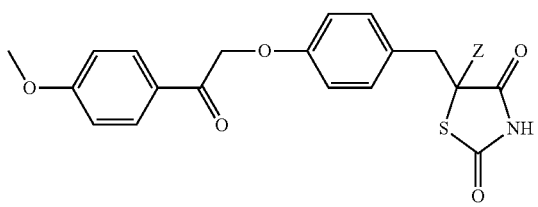

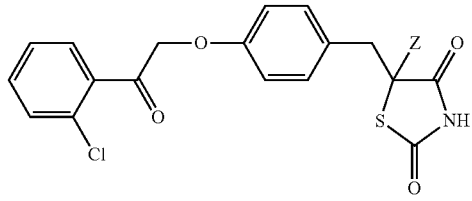

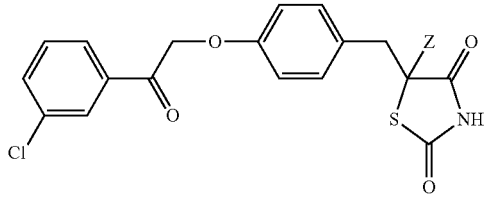

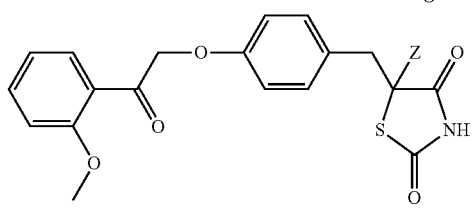

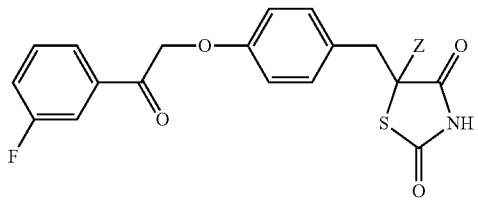

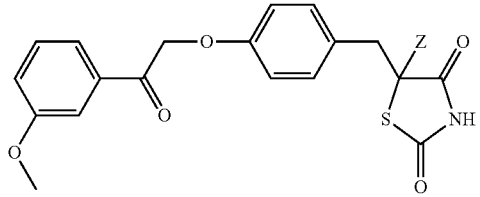

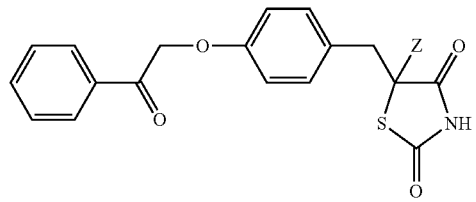
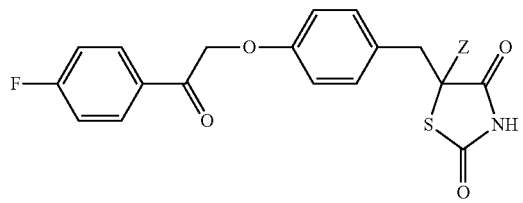
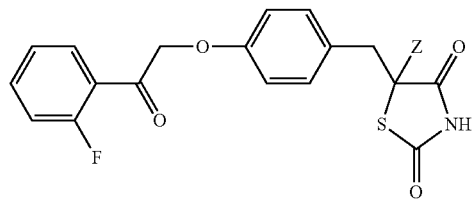
or a stereoisomer or pharmaceutically acceptable salt form thereof wherein Z is as defined above for formula I.
In another aspect, the invention provides a deuterium-enriched compound, selected from:
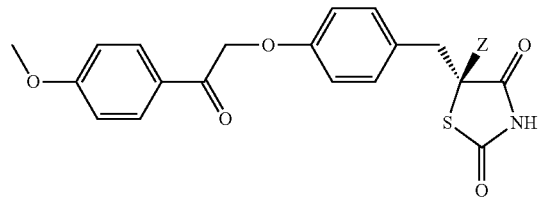
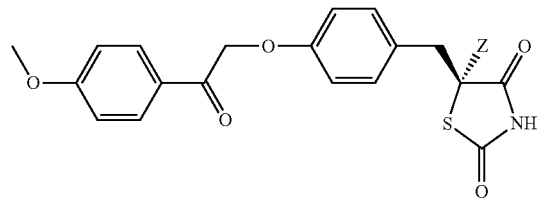
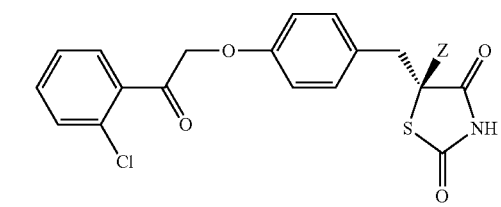
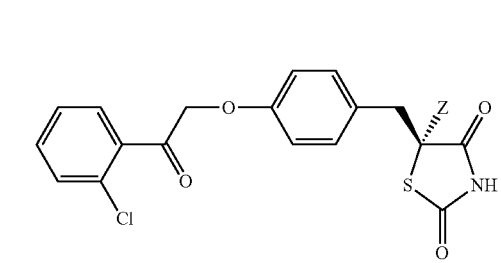
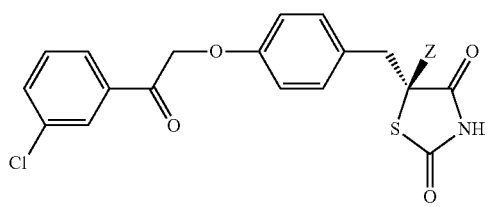
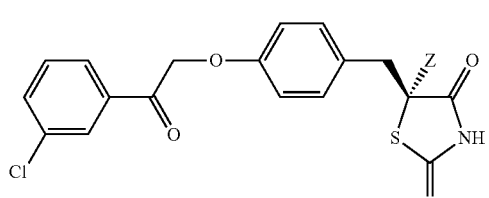
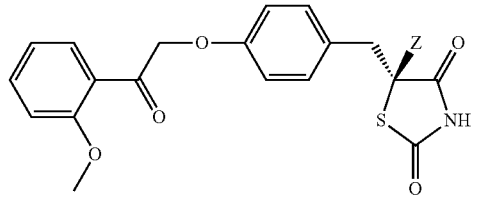
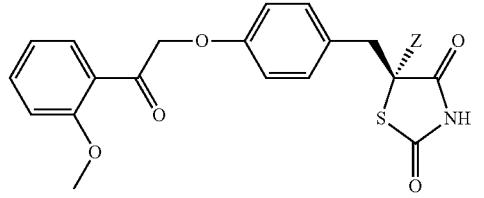
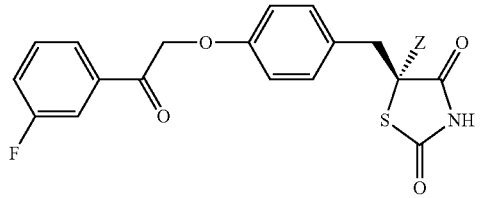
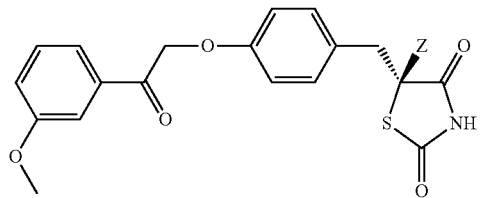
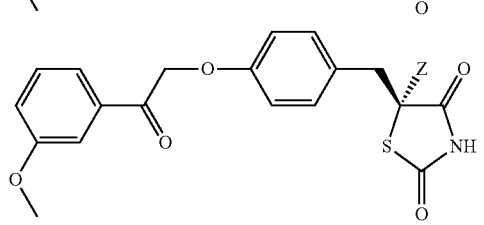

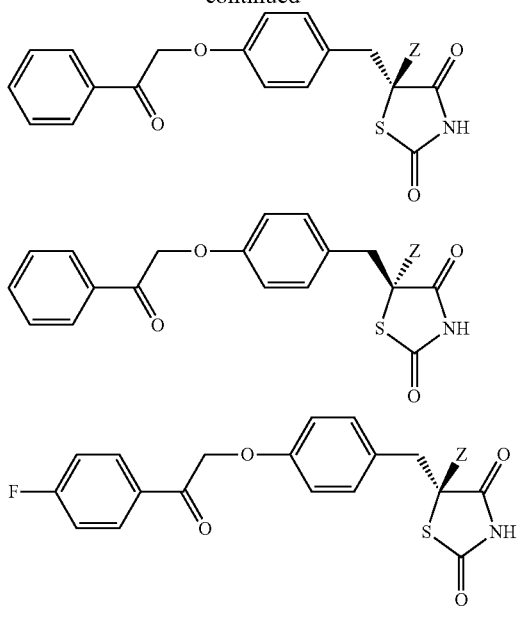

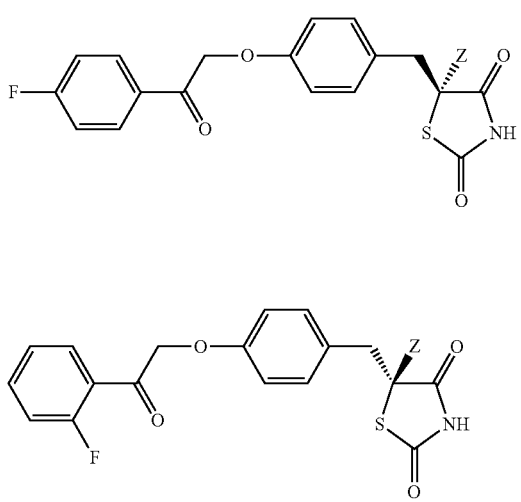

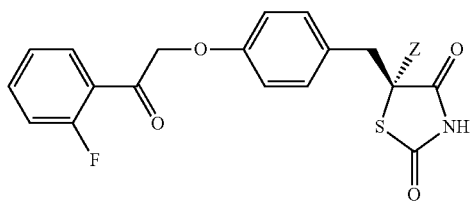

or a pharmaceutically acceptable salt form thereof; wherein Z is as defined above for formula I.

In another aspect, the compounds above have an enantiomeric excess, with respect to the C—Z carbon, of at least 5%.

In another aspect, the invention provides a deuterium-enriched compound of formula VII or a stereoisomer or pharmaceutically acceptable salt form thereof:

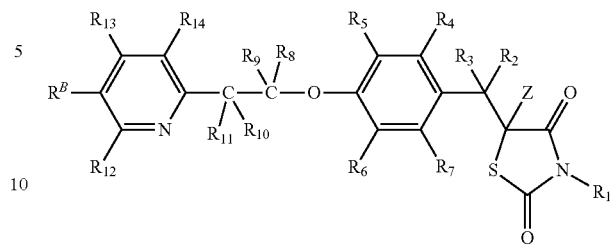

wherein:

$R^1, R^2, R^3, R^4, R^5, R^6, R^7, R^8, R^9, R^{10}, R^{12}, R^{13}$, and $R^{14}$ are independently selected from H and D;

Z is H or D, provided that the abundance of deuterium in Z is at least 30%;

$CR^{10}R^{11}$=C(O) or $CH_2$;

$R^B$ is selected from: $CH_3C(O)$—, $CH_3CH(OR)$—, and —$CH_2CO_2H$;

R is selected from H, D, and acyl; and a hydrogen atom present anywhere in the compound of Formula VII is optionally replaced by D.

In another aspect, the invention provides a deuterium-enriched compound of formula VIIa or VIIb or a pharmaceutically acceptable salt form thereof:

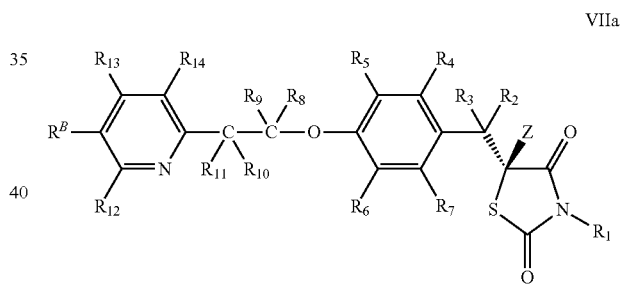

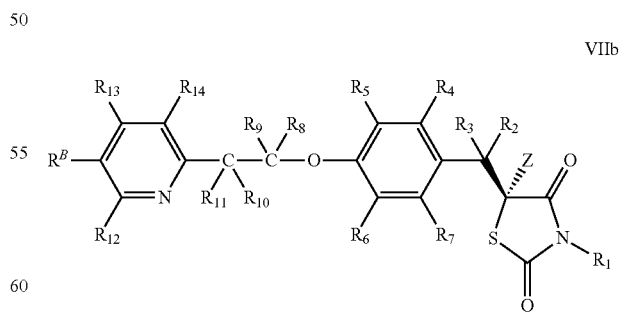

wherein the variables are as defined above for formula VII.

In another aspect, the invention provides a deuterium-enriched compound of formula VIIa or VIIb or a pharmaceutically acceptable salt form thereof:

VIIa

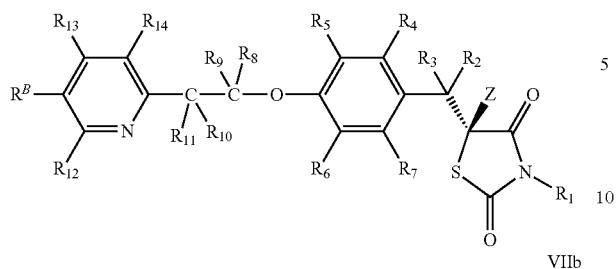

VIIb

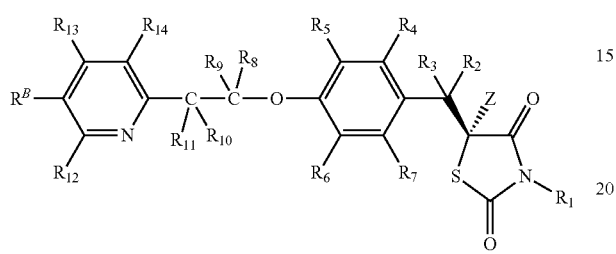

wherein the variables are as defined above for formula VII; and, the compound of formula VIIa or VIIb has an enantiomeric excess, with respect to the C—Z carbon, of at least 5%.

In an aspect, the invention provides a deuterium-enriched compound of formula VIII or a stereoisomer or pharmaceutically acceptable salt form thereof

VIII

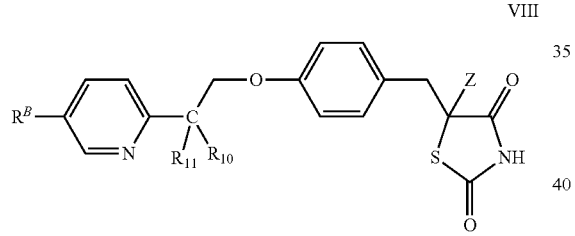

wherein:
Z is H or D, provided that the abundance of deuterium in Z is at least 30%;
$CR^{10}R^{11}$=C(O) or $CH_2$;
$R^B$ is selected from: $CH_3C(O)$—, $CH_3CH(OR)$—, and —$CH_2CO_2H$;
R is selected from H, D, and acyl; and
a hydrogen atom present anywhere in the compound of Formula VIII is optionally replaced by D.

In another aspect, the invention provides a deuterium-enriched compound of formula VIIIa or VIIIb or a pharmaceutically acceptable salt form thereof:

VIIIa

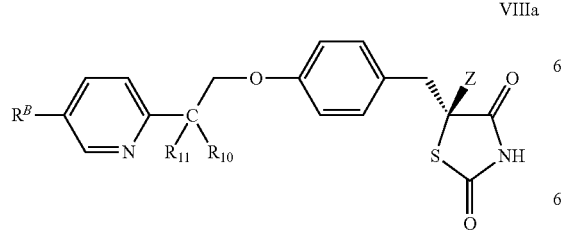

VIIIb

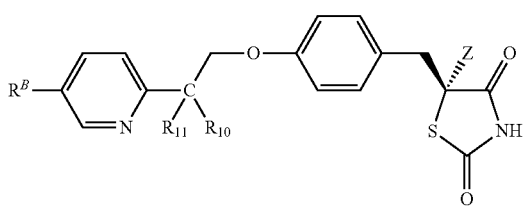

wherein the variables are as defined above for formula VIII.

In another aspect, the invention provides a deuterium-enriched compound of formula VIIIa or VIIIb or a pharmaceutically acceptable salt form thereof:

VIIIa

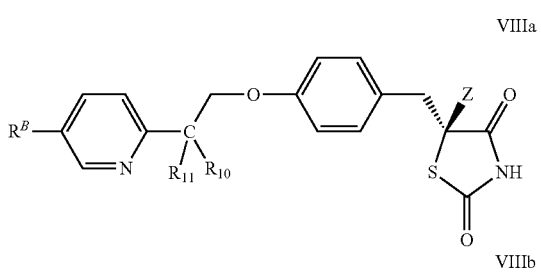

VIIIb

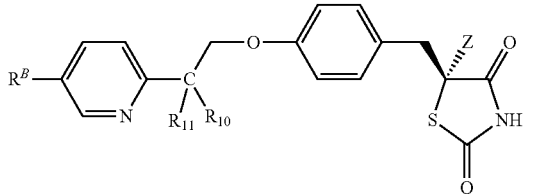

wherein the variables are as defined above for formula VIII; and the compound of formula VIIIa or VIIIb has an enantiomeric excess, with respect to the C—Z carbon, of at least 5%.

In another aspect, the invention provides a deuterium-enriched compound of formula IX or a stereoisomer or pharmaceutically acceptable salt form thereof:

IX

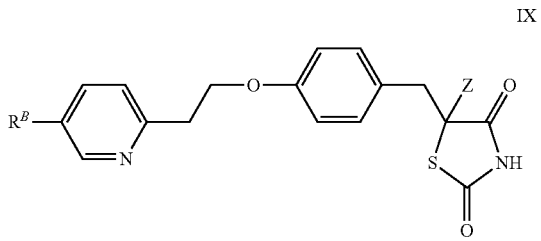

wherein:
Z is H or D, provided that the abundance of deuterium in Z is at least 30%;
$R^B$ is selected from: $CH_3C(O)$—, $CH_3CH(OR)$—, and —$CH_2CO_2H$;
R is selected from H, D, and acyl; and
a hydrogen atom present anywhere in the compound of Formula VIII is optionally replaced by D.

In another aspect, the invention provides a deuterium-enriched compound of formula IXa or IXb or pharmaceutically acceptable salt form thereof:

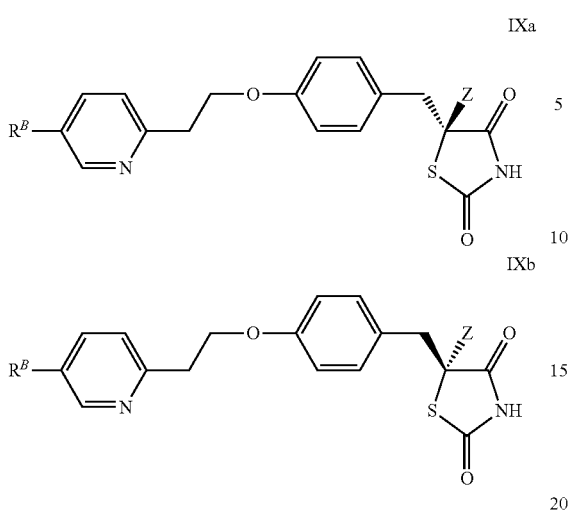

IXa

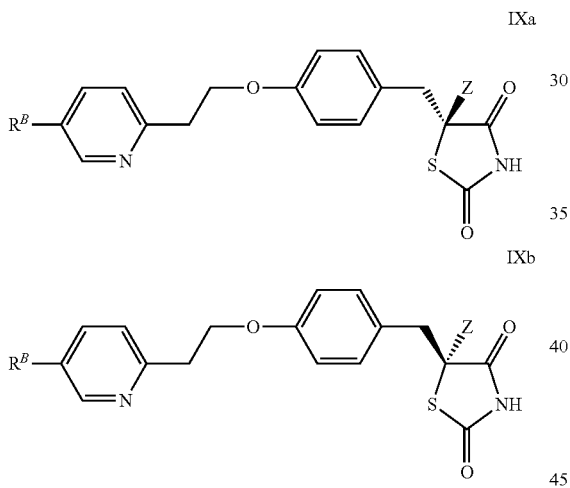

IXb wherein the variables are as defined above for formula IX.

In another aspect, the invention provides a deuterium-enriched compound of formula IXa or IXb or pharmaceutically acceptable salt form thereof:

IXa

IXb wherein the variables are as defined above for formula IX; and the compound of formula IXa or IXb has an enantiomeric excess, with respect to the C—Z carbon, of at least 5%.

In another aspect, the invention provides a deuterium-enriched compound of formula X or a stereoisomer or pharmaceutically acceptable salt form thereof:

X wherein the variables are as defined above for formula VIII.

In another aspect, the invention provides a deuterium-enriched compound of formula Xa or Xb or pharmaceutically acceptable salt form thereof:

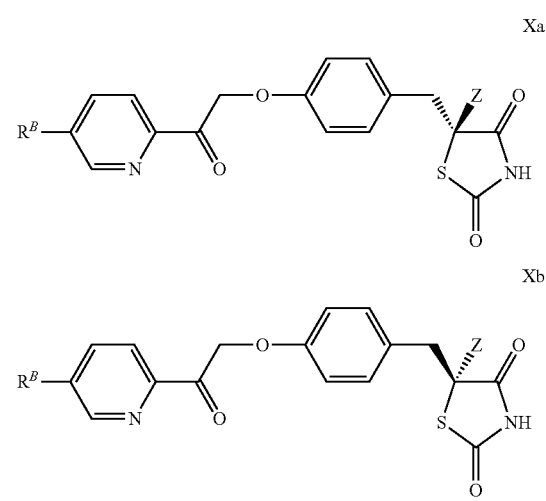

Xa

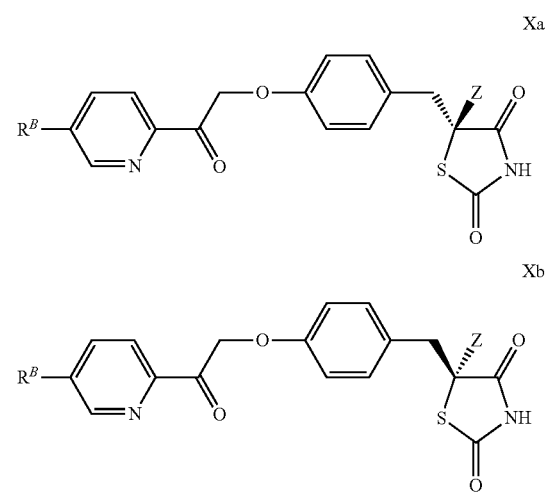

Xb wherein the variables are as defined above for formula VIII.

In another aspect, the invention provides a deuterium-enriched compound of formula Xa or Xb or pharmaceutically acceptable salt form thereof:

Xa

Xb wherein the variables are as defined above for formula VIII; and the compound of formula Xa or Xb has an enantiomeric excess, with respect to the C—Z carbon, of at least 5%.

In another aspect, the invention provides a deuterium-enriched compound, selected from:

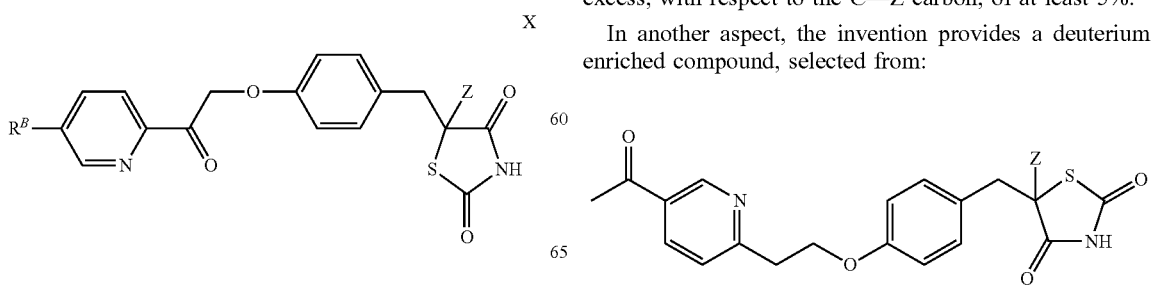

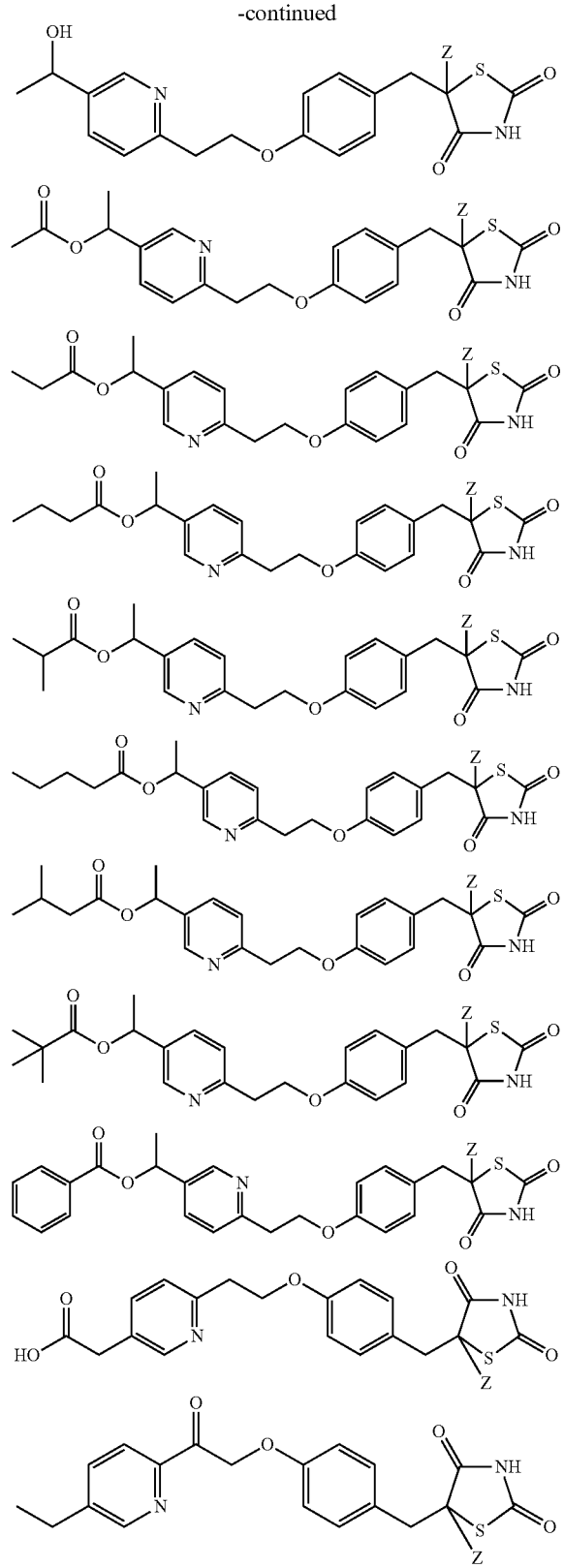
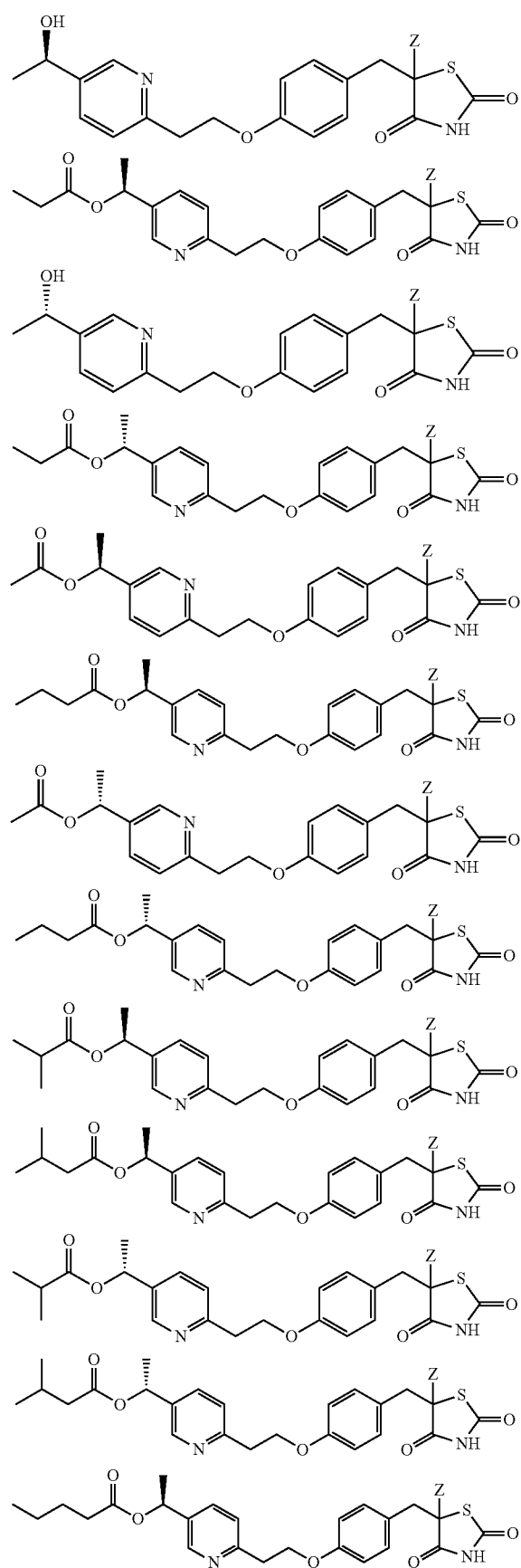
or a stereoisomer or pharmaceutically acceptable salt form thereof wherein Z is as defined above for formula I. In certain embodiments, the compound is further selected from:

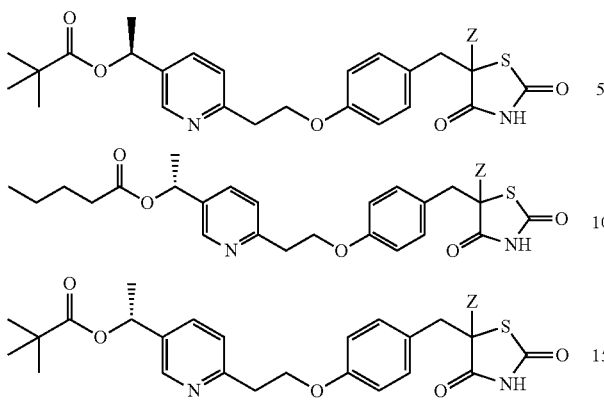
or a stereoisomer or pharmaceutically acceptable salt form thereof.
In another aspect, the invention provides a deuterium-enriched compound, selected from:
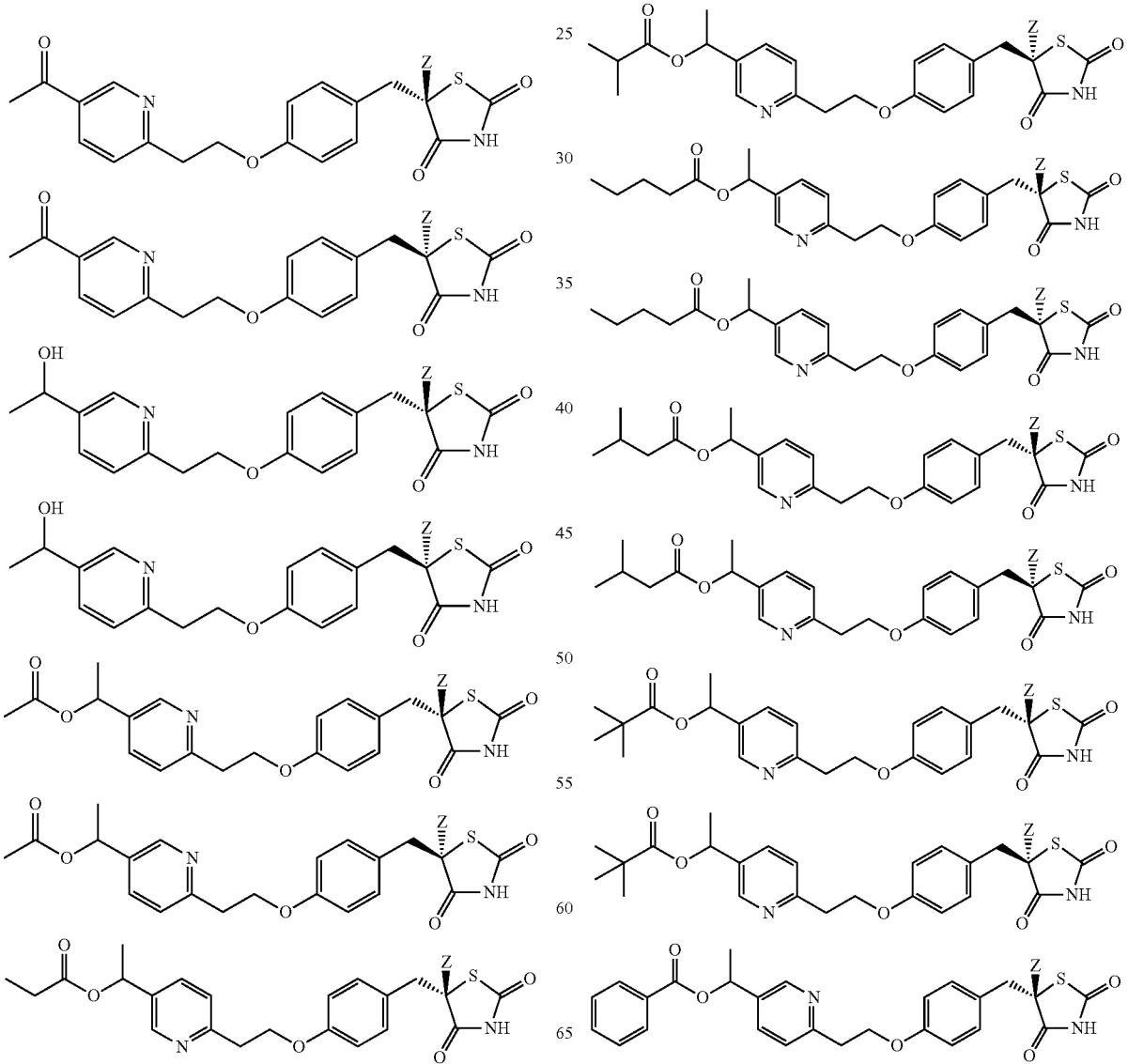
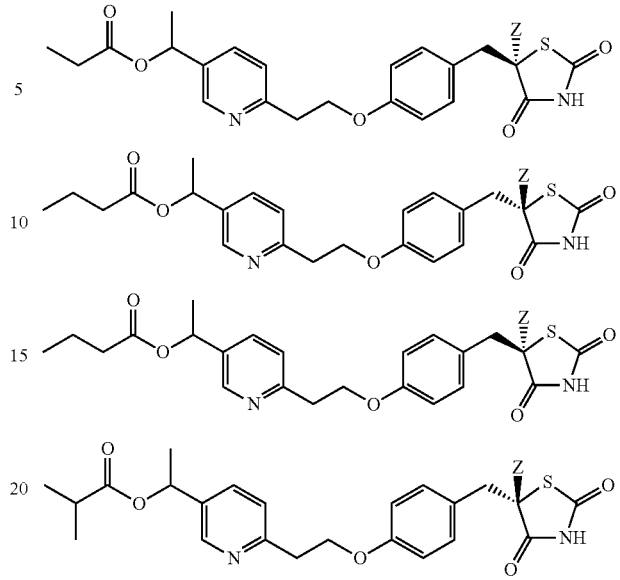

-continued

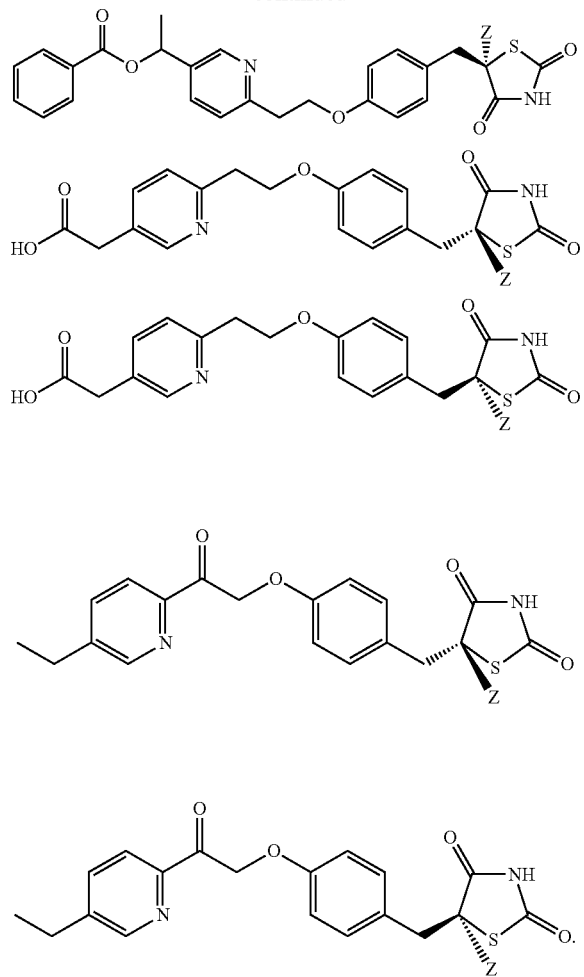

or a pharmaceutically acceptable salt form thereof; and, wherein Z is as defined above for formula I.

In another aspect, the compounds above have an enantiomeric excess, with respect to the C—Z carbon, of at least 5%. In yet other embodiments, the compounds above have an enantiomeric excess, with respect to the C—Z carbon, of at least 70%, 80%, 90%, 95%, 97%, 98%, or 99%.

A more specific embodiment of the invention provides a deuterium-enriched compound represented by Formula XI:

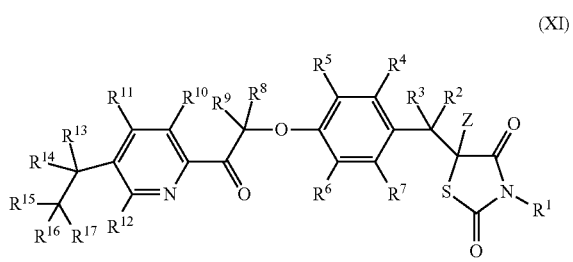

(XI)

or a stereoisomer or pharmaceutically acceptable salt form thereof; wherein $R^1$ through $R^{17}$ are independently hydrogen or D; and Z is hydrogen or D, provided that the abundance of deuterium in Z is at least 50%.

In certain embodiments, the compound is

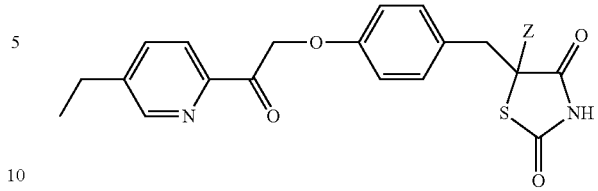

or a stereoisomer or pharmaceutically acceptable salt form thereof, wherein Z is H or D, provided that the abundance of deuterium in Z is at least 50%. In certain other embodiments, the compound is

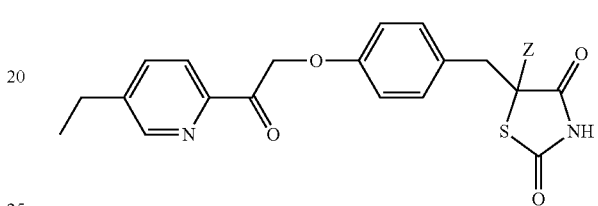

or a stereoisomer thereof, wherein Z is H or D, provided that the abundance of deuterium in Z is at least 50%.

In certain embodiments, the abundance of deuterium in Z is at least 80%. In certain other embodiments, the abundance of deuterium in Z is at least 90%. In yet other embodiments, the abundance of deuterium in Z is at least 95%.

In yet other embodiments, the compound is

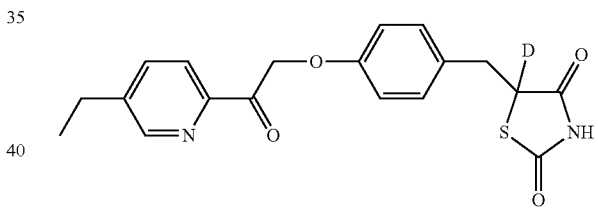

or a stereoisomer or pharmaceutically acceptable salt form thereof.

Another more specific embodiment of the invention provides a deuterium-enriched compound represented by Formula XIa:

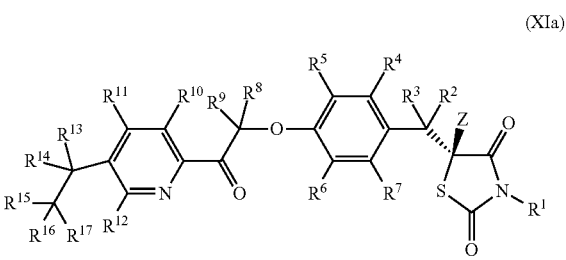

(XIa)

or a stereoisomer or pharmaceutically acceptable salt form thereof; wherein $R^1$ through $R^{17}$ are independently hydrogen or D; and Z is hydrogen or D, provided that the abundance of deuterium in Z is at least 50%, and the compound has an enantiomeric excess, with respect to the C—Z carbon, of at least 70%.

In certain embodiments, the compound is

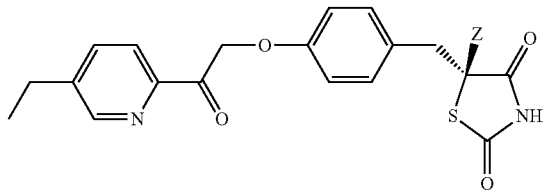

or a pharmaceutically acceptable salt form thereof, wherein the compound has an enantiomeric excess, with respect to the C—Z carbon, of at least 80%, wherein Z is H or D, provided that the abundance of deuterium in Z is at least 50%. In certain other embodiments, the compound is

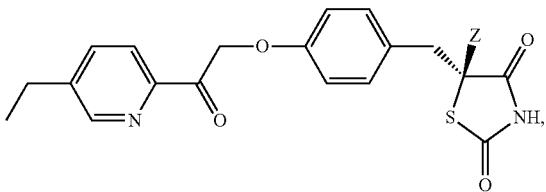

wherein the compound has an enantiomeric excess, with respect to the C—Z carbon, of at least 80%, wherein Z is H or D, provided that the abundance of deuterium in Z is at least 50%.

In certain embodiments, the abundance of deuterium in Z is at least 80%. In certain other embodiments, the abundance of deuterium in Z is at least 90%. In yet other embodiments, the abundance of deuterium in Z is at least 95%.

In certain embodiments, the compound has an enantiomeric excess, with respect to the C—Z carbon, of at least 90%. In certain other embodiments, the compound has an enantiomeric excess, with respect to the C—Z carbon, of at least 95%.

In yet other embodiments, the compound is

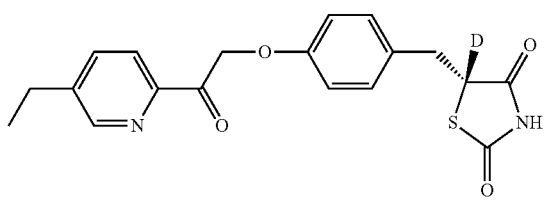 [SMILES: [2H][C@]1(Cc2ccc(OCC(=O)c3ccc(CC)cn3)cc2)SC(=O)NC1=O]

or a pharmaceutically acceptable salt form thereof, wherein the compound has an enantiomeric excess of at least 90%, or more preferably at least 95%.

A more specific embodiment of the invention provides a deuterium-enriched compound represented by Formula XIb:

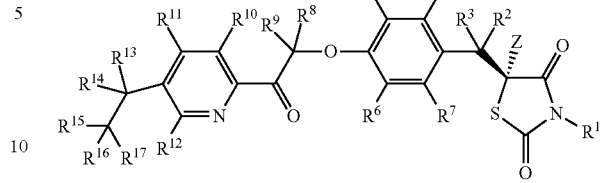

(XIb)

or a stereoisomer or pharmaceutically acceptable salt form thereof; wherein $R^1$ through $R^{17}$ are independently hydrogen or D; and Z is hydrogen or D, provided that the abundance of deuterium in Z is at least 50%, and the compound has an enantiomeric excess, with respect to the C—Z carbon, of at least 70%.

In certain embodiments, the compound is

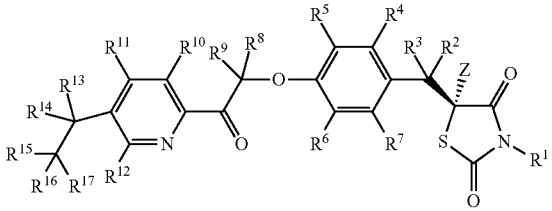

or a pharmaceutically acceptable salt form thereof, wherein the compound has an enantiomeric excess, with respect to the C—Z carbon, of at least 80%, wherein Z is H or D, provided that the abundance of deuterium in Z is at least 50%. In certain other embodiments, the compound is

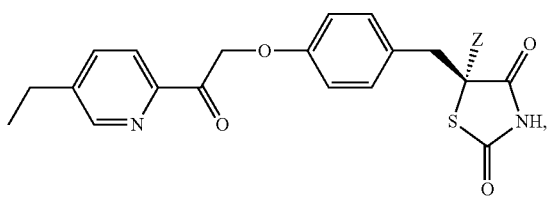

wherein the compound has an enantiomeric excess, with respect to the C—Z carbon, of at least 80%, wherein Z is H or D, provided that the abundance of deuterium in Z is at least 50%.

In certain embodiments, the abundance of deuterium in Z is at least 80%. In certain other embodiments, the abundance of deuterium in Z is at least 90%. In yet other embodiments, the abundance of deuterium in Z is at least 95%.

In certain embodiments, the compound has an enantiomeric excess, with respect to the C—Z carbon, of at least 90%. In certain other embodiments, the compound has an enantiomeric excess, with respect to the C—Z carbon, of at least 95%.

In yet other embodiments, the compound is

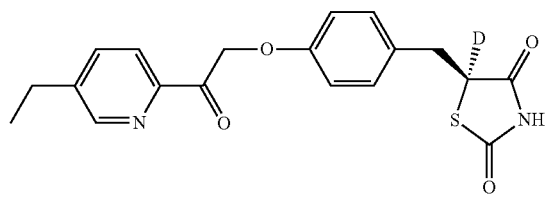 [SMILES: [2H][C@@]1(Cc2ccc(OCC(=O)c3ccc(CC)cn3)cc2)SC(=O)NC1=O]

or a pharmaceutically acceptable salt form thereof, wherein the compound has an enantiomeric excess of at least 90%, or more preferably at least 95%.

Another more specific embodiment of the invention provides a deuterium-enriched compound represented by Formula XII:

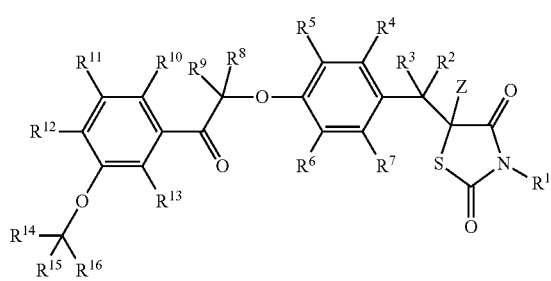

(XII)

or a stereoisomer or pharmaceutically acceptable salt form thereof; wherein $R^1$ through $R^{16}$ are independently hydrogen or D; and Z is hydrogen or D, provided that the abundance of deuterium in Z is at least 50%.

In certain embodiments, the compound is

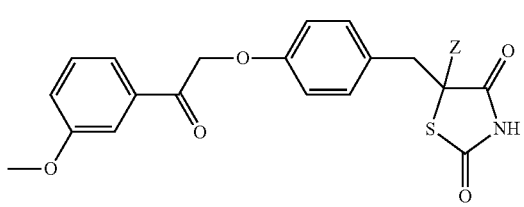

or a stereoisomer or pharmaceutically acceptable salt form thereof, wherein Z is H or D, provided that the abundance of deuterium in Z is at least 50%. In certain other embodiments, the compound is

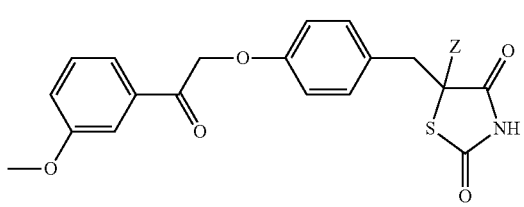

or a stereoisomer thereof, wherein Z is H or D, provided that the abundance of deuterium in Z is at least 50%.

In certain embodiments, the abundance of deuterium in Z is at least 80%. In certain other embodiments, the abundance of deuterium in Z is at least 90%. In yet other embodiments, the abundance of deuterium in Z is at least 95%.

In yet other embodiments, the compound is

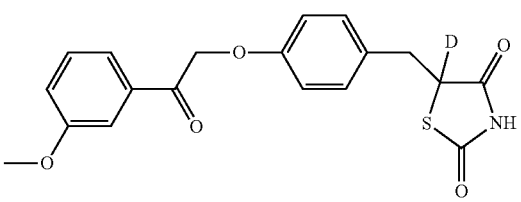

or a stereoisomer or pharmaceutically acceptable salt form thereof.

Another more specific embodiment of the invention provides a deuterium-enriched compound represented by Formula XIIa:

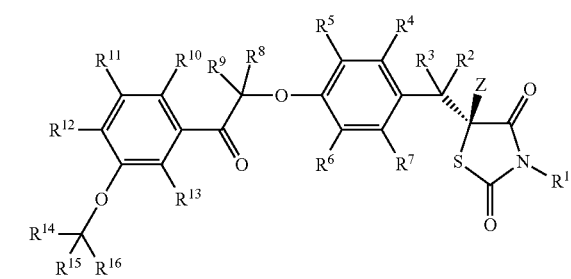

(XIIa)

or a stereoisomer or pharmaceutically acceptable salt form thereof; wherein $R^1$ through $R^{16}$ are independently hydrogen or D; and Z is hydrogen or D, provided that the abundance of deuterium in Z is at least 50%, and the compound has an enantiomeric excess, with respect to the C—Z carbon, of at least 70%.

In certain embodiments, the compound is

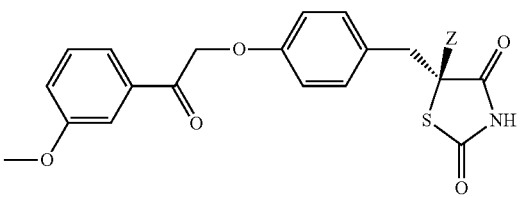

or a pharmaceutically acceptable salt form thereof, wherein the compound has an enantiomeric excess, with respect to the C—Z carbon, of at least 80%, wherein Z is H or D, provided that the abundance of deuterium in Z is at least 50%. In certain other embodiments, the compound is

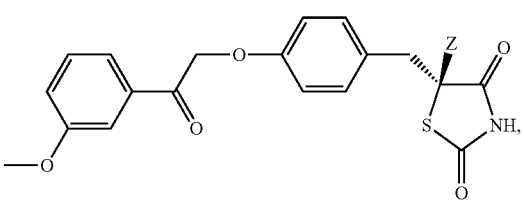

wherein the compound has an enantiomeric excess, with respect to the C—Z carbon, of at least 80%, wherein Z is H or D, provided that the abundance of deuterium in Z is at least 50%.

In certain embodiments, the abundance of deuterium in Z is at least 80%. In certain other embodiments, the abundance of deuterium in Z is at least 90%. In yet other embodiments, the abundance of deuterium in Z is at least 95%.

In certain embodiments, the compound has an enantiomeric excess, with respect to the C—Z carbon, of at least 90%. In certain other embodiments, the compound has an enantiomeric excess, with respect to the C—Z carbon, of at least 95%.

In yet other embodiments, the compound is

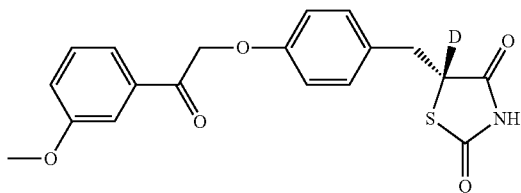 [SMILES: [2H][C@]1(Cc2ccc(OCC(=O)c3cccc(OC)c3)cc2)SC(=O)NC1=O]

or a pharmaceutically acceptable salt form thereof, wherein the compound has an enantiomeric excess of at least 90%, or more preferably at least 95%.

A more specific embodiment of the invention provides a deuterium-enriched compound represented by Formula XIIb:

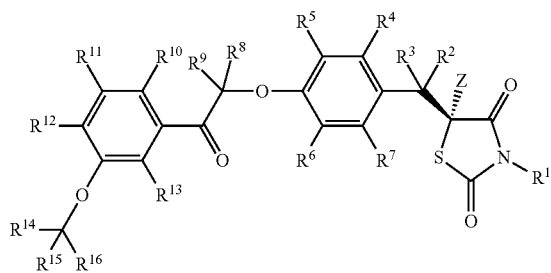

or a stereoisomer or pharmaceutically acceptable salt form thereof; wherein $R^1$ through $R^{16}$ are independently hydrogen or D; and Z is hydrogen or D, provided that the abundance of deuterium in Z is at least 50%, and the compound has an enantiomeric excess, with respect to the C—Z carbon, of at least 70%.

In certain embodiments, the compound is

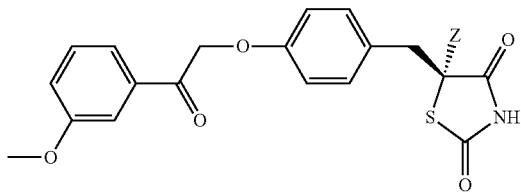

or a pharmaceutically acceptable salt form thereof, wherein the compound has an enantiomeric excess, with respect to the C—Z carbon, of at least 80%, wherein Z is H or D, provided that the abundance of deuterium in Z is at least 50%. In certain other embodiments, the compound is

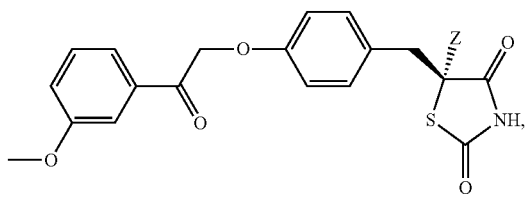

wherein the compound has an enantiomeric excess, with respect to the C—Z carbon, of at least 80%, wherein Z is H or D, provided that the abundance of deuterium in Z is at least 50%.

In certain embodiments, the abundance of deuterium in Z is at least 80%. In certain other embodiments, the abundance of deuterium in Z is at least 90%. In yet other embodiments, the abundance of deuterium in Z is at least 95%.

In certain embodiments, the compound has an enantiomeric excess, with respect to the C—Z carbon, of at least 90%. In certain other embodiments, the compound has an enantiomeric excess, with respect to the C—Z carbon, of at least 95%.

In yet other embodiments, the compound is

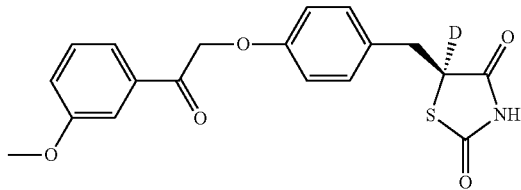 [SMILES: [2H][C@@]1(Cc2ccc(OCC(=O)c3cccc(OC)c3)cc2)SC(=O)NC1=O]

or a pharmaceutically acceptable salt form thereof, wherein the compound has an enantiomeric excess of at least 90%, or more preferably at least 95%.

Additional exemplary compounds are provided in the following tables, wherein variable Z is H or D, provided that the abundance of deuterium in Z is at least 30%.

TABLE 1

The R groups are as specified, and where not defined, are as defined above for Formula VII.

| Compound No. | Variable Definitions |
|---|---|
| 1 | $R^B$ = $CH_3CH_2$—<br>$R^1$, $R^2$, $R^3$, $R^4$, $R^5$, $R^6$, $R^7$, $R^8$,<br>$R^9$, $R^{12}$, $R^{13}$, and $R^{14}$ = H |
| 2 | $R^B$ = $CD_3CD_2$—<br>$R^1$, $R^2$, $R^3$, $R^4$, $R^5$, $R^6$, $R^7$, $R^8$,<br>$R^9$, $R^{12}$, $R^{13}$, and $R^{14}$ = D |

TABLE 1-continued

| | |
|---|---|
| 3 | $R^B$ = CH$_3$CH$_2$—<br>$R^2$ and $R^3$ = D |
| 4 | $R^B$ = CH$_3$CH$_2$—<br>$R^4$, $R^5$, $R^6$, and $R^7$ = D |
| 5 | $R^B$ = CH$_3$CH$_2$—<br>$R^8$ and $R^9$ = D |
| 6 | $R^B$ = CH$_3$CH$_2$—<br>$R^{12}$, $R^{13}$, and $R^{14}$ = D |

Table 2: The compounds corresponding to Table 1, wherein the abundance of deuterium in Z is at least 40%. Table 3: The compounds corresponding to Table 1, wherein the abundance of deuterium in Z is at least 50%. Table 4: The compounds corresponding to Table 1, wherein the abundance of deuterium in Z is at least 60%. Table 5: The compounds corresponding to Table 1, wherein the abundance of deuterium in Z is at least 70%. Table 6: The compounds corresponding to Table 1, wherein the abundance of deuterium in Z is at least 80%. Table 7: The compounds corresponding to Table 1, wherein the abundance of deuterium in Z is at least 90%. Table 8: The compounds corresponding to Table 1, wherein the abundance of deuterium in Z is at least 97%. Table 9: The compounds corresponding to Table 1, wherein the abundance of deuterium in Z is about 100%.

TABLE 10

The R groups are as specified, and where not defined, are as defined above for Formula VII.

[Chemical structure diagram with labels $R_{13}$, $R_{14}$, $R_9$, $R_8$, $R_5$, $R_4$, $R^B$, $R_{12}$, $R_3$, $R_2$, $R_6$, $R_7$, Z, N, S, O, $R_1$]

| Compound No. | Variable Definitions |
|---|---|
| 1 | $R^B$ = CH$_3$CH$_2$—<br>$R^1$, $R^2$, $R^3$, $R^4$, $R^5$, $R^6$, $R^7$, $R^8$, $R^9$, $R^{12}$, $R^{13}$, and $R^{14}$ = H |
| 2 | $R^B$ = CD$_3$CD$_2$—<br>$R^1$, $R^2$, $R^3$, $R^4$, $R^5$, $R^6$, $R^7$, $R^8$, $R^9$, $R^{12}$, $R^{13}$, and $R^{14}$ = D |
| 3 | $R^B$ = CH$_3$CH$_2$—<br>$R^2$ and $R^3$ = D |
| 4 | $R^B$ = CH$_3$CH$_2$—<br>$R^4$, $R^5$, $R^6$, and $R^7$ = D |
| 5 | $R^B$ = CH$_3$CH$_2$—<br>$R^8$ and $R^9$ = D |
| 6 | $R^B$ = CH$_3$CH$_2$—<br>$R^{12}$, $R^{13}$, and $R^{14}$ = D | wherein the compounds of Table 10 have an enantiomeric excess, with respect to the C—Z carbon, of at least 5%.

Table 11: The compounds corresponding to Table 10, wherein the abundance of deuterium in Z is at least 40% and the compounds of Table 11 have an enantiomeric excess, with respect to the C—Z carbon, of at least 5%. Table 12: The compounds corresponding to Table 10, wherein the abundance of deuterium in Z is at least 50% and the compounds of Table 12 have an enantiomeric excess, with respect to the C—Z carbon, of at least 5%. Table 13: The compounds corresponding to Table 10, wherein the abundance of deuterium in Z is at least 60% and the compounds of Table 13 have an enantiomeric excess, with respect to the C—Z carbon, of at least 5%. Table 14: The compounds corresponding to Table 10, wherein the abundance of deuterium in Z is at least 70% and the compounds of Table 14 have an enantiomeric excess, with respect to the C—Z carbon, of at least 5%. Table 15: The compounds corresponding to Table 10, wherein the abundance of deuterium in Z is at least 80% and the compounds of Table 15 have an enantiomeric excess, with respect to the C—Z carbon, of at least 5%. Table 16: The compounds corresponding to Table 10, wherein the abundance of deuterium in Z is at least 90% and the compounds of Table 16 have an enantiomeric excess, with respect to the C—Z carbon, of at least 5%. Table 17: The compounds corresponding to Table 10, wherein the abundance of deuterium in Z is at least 97% and the compounds of Table 17 have an enantiomeric excess, with respect to the C—Z carbon, of at least 5%. Table 18: The compounds corresponding to Table 10, wherein the abundance of deuterium in Z is about 100% and the compounds of Table 18 have an enantiomeric excess, with respect to the C—Z carbon, of at least 5%.

TABLE 19

The R groups are as specified, and where not defined, are as defined above for Formula VII.

[Chemical structure diagram with labels $R_{13}$, $R_{14}$, $R_9$, $R_8$, $R_5$, $R_4$, $R^B$, $R_{12}$, $R_3$, $R_2$, $R_6$, $R_7$, Z, N, S, O, $R_1$]

| Compound No. | Variable Definitions |
|---|---|
| 1 | $R^B$ = CH$_3$CH$_2$—<br>$R^1$, $R^2$, $R^3$, $R^4$, $R^5$, $R^6$, $R^7$, $R^8$, $R^9$, $R^{12}$, $R^{13}$, and $R^{14}$ = H |
| 2 | $R^B$ = CD$_3$CD$_2$—<br>$R^1$, $R^2$, $R^3$, $R^4$, $R^5$, $R^6$, $R^7$, $R^8$, $R^9$, $R^{12}$, $R^{13}$, and $R^{14}$ = D |
| 3 | $R^B$ = CH$_3$CH$_2$—<br>$R^2$ and $R^3$ = D |
| 4 | $R^B$ = CH$_3$CH$_2$—<br>$R^4$, $R^5$, $R^6$, and $R^7$ = D |
| 5 | $R^B$ = CH$_3$CH$_2$—<br>$R^8$ and $R^9$ = D |
| 6 | $R^B$ = CH$_3$CH$_2$—<br>$R^{12}$, $R^{13}$, and $R^{14}$ = D | wherein the compounds of Table 19 have an enantiomeric excess, with respect to the C—Z carbon, of at least 5%.

Table 20: The compounds corresponding to Table 19, wherein the abundance of deuterium in Z is at least 40% and the compounds of Table 20 have an enantiomeric excess, with respect to the C—Z carbon, of at least 5%. Table 21: The compounds corresponding to Table 19, wherein the abundance of deuterium in Z is at least 50% and the compounds of Table 21 have an enantiomeric excess, with respect to the C—Z carbon, of at least 5%. Table 22: The compounds corresponding to Table 19, wherein the abundance of deuterium in Z is at least 60% and the compounds of Table 22 have an enantiomeric excess, with respect to the C—Z carbon, of at least 5%. Table 23: The compounds corresponding to Table 19, wherein the abundance of deuterium in Z is at least 70% and the compounds of Table 23 have an enantiomeric excess, with respect to the C—Z carbon, of at least 5%. Table 24: The compounds corresponding to Table 19, wherein the abundance of deuterium in Z is at least 80% and the compounds of Table 24 have an enantiomeric excess, with respect to the C—Z carbon, of at least 5%. Table 25: The compounds corresponding to Table 19, wherein the abundance of deuterium in Z is at least 90% and the compounds of Table 25 have an enantiomeric excess, with respect to the C—Z carbon, of at least 5%. Table 26: The compounds corresponding to Table 19, wherein the abundance of deuterium in Z is at least 97% and the compounds of Table 26 have an enantiomeric excess, with respect to the C—Z carbon, of at least 5%. Table 27: The compounds corresponding to Table 19, wherein the abundance of deuterium in Z is about 100% and the compounds of Table 27 have an enantiomeric excess, with respect to the C—Z carbon, of at least 5%.

TABLE 28

The R groups are as specified, and where not defined, are as defined above for Formula IV.

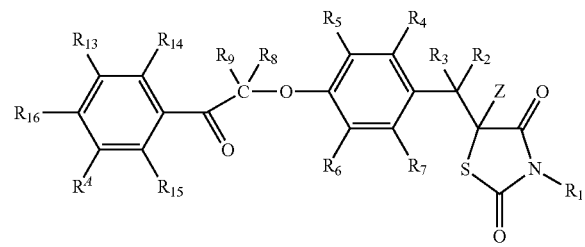

| Compound No. | Variable Definitions |
|---|---|
| 1 | $R^4 = -OCH_3$<br>$R^1, R^2, R^3, R^4, R^5, R^6, R^7, R^8,$<br>$R^9, R^{12}, R^{13},$ and $R^{14} = H$ |
| 2 | $R^4 = -OCD_3$<br>$R^1, R^2, R^3, R^4, R^5, R^6, R^7, R^8,$<br>$R^9, R^{12}, R^{13},$ and $R^{14} = D$ |
| 3 | $R^4 = -OCH_3$<br>$R^2$ and $R^3 = D$ |
| 4 | $R^4 = -OCH_3$<br>$R^4, R^5, R^6,$ and $R^7 = D$ |
| 5 | $R^4 = -OCH_3$<br>$R^8$ and $R^9 = D$ |
| 6 | $R^4 = -OCH_3$<br>$R^{12}, R^{13},$ and $R^{14} = D$ |

Table 29: The compounds corresponding to Table 28, wherein the abundance of deuterium in Z is at least 40%. Table 30: The compounds corresponding to Table 28, wherein the abundance of deuterium in Z is at least 50%. Table 31: The compounds corresponding to Table 28, wherein the abundance of deuterium in Z is at least 60%. Table 32: The compounds corresponding to Table 28, wherein the abundance of deuterium in Z is at least 70%. Table 33: The compounds corresponding to Table 28, wherein the abundance of deuterium in Z is at least 80%. Table 34: The compounds corresponding to Table 28, wherein the abundance of deuterium in Z is at least 90%. Table 35: The compounds corresponding to Table 28, wherein the abundance of deuterium in Z is at least 97%. Table 36: The compounds corresponding to Table 28, wherein the abundance of deuterium in Z is about 100%.

TABLE 37

The R groups are as specified, and where not defined, are as defined above for Formula IV.

| Compound No. | Variable Definitions |
|---|---|
| 1 | $R^4 = -OCH_3$<br>$R^1, R^2, R^3, R^4, R^5, R^6, R^7, R^8,$<br>$R^9, R^{12}, R^{13},$ and $R^{14} = H$ |
| 2 | $R^4 = -OCD_3$<br>$R^1, R^2, R^3, R^4, R^5, R^6, R^7, R^8,$<br>$R^9, R^{12}, R^{13},$ and $R^{14} = D$ |
| 3 | $R^4 = -OCH_3$<br>$R^2$ and $R^3 = D$ |
| 4 | $R^4 = -OCH_3$<br>$R^4, R^5, R^6,$ and $R^7 = D$ |
| 5 | $R^4 = -OCH_3$<br>$R^8$ and $R^9 = D$ |
| 6 | $R^4 = -OCH_3$<br>$R^{12}, R^{13},$ and $R^{14} = D$ | wherein the compounds of Table 37 have an enantiomeric excess, with respect to the C—Z carbon, of at least 5%.

Table 38: The compounds corresponding to Table 37, wherein the abundance of deuterium in Z is at least 40% and the compounds have an enantiomeric excess, with respect to the C—Z carbon, of at least 5%. Table 39: The compounds corresponding to Table 37, wherein the abundance of deuterium in Z is at least 50% and the compounds have an enantiomeric excess, with respect to the C—Z carbon, of at least 5%. Table 40: The compounds corresponding to Table 37, wherein the abundance of deuterium in Z is at least 60% and the compounds have an enantiomeric excess, with respect to the C—Z carbon, of at least 5%. Table 41: The compounds corresponding to Table 37, wherein the abundance of deuterium in Z is at least 70% and the compounds have an enantiomeric excess, with respect to the C—Z carbon, of at least 5%. Table 42: The compounds corresponding to Table 37, wherein the abundance of deuterium in Z is at least 80% and the compounds have an enantiomeric excess, with respect to the C—Z carbon, of at least 5%. Table 43: The compounds corresponding to Table 37, wherein the abundance of deuterium in Z is at least 90% and the compounds have an enantiomeric excess, with respect to the C—Z carbon, of at least 5%. Table 44: The compounds corresponding to Table 37, wherein the abundance of deuterium in Z is at least 97% and the compounds have an enantiomeric excess, with respect to the C—Z carbon, of at least 5%. Table 45: The compounds corresponding to Table 37, wherein the abundance of deuterium in Z is about 100% and the compounds have an enantiomeric excess, with respect to the C—Z carbon, of at least 5%.

TABLE 46

The R groups are as specified, and where not
defined, are as defined above for Formula IV.

[Chemical structure showing a compound with substituents $R_1$ through $R_{16}$, including a phenyl ring with $R_{13}$, $R_{14}$, $R_{16}$, $R^4$, $R_{15}$; a $R_9R_8C$—O linkage; another phenyl ring with $R_5$, $R_4$, $R_3$, $R_2$, $R_6$, $R_7$; and a thiazolidinedione ring with $Z$ and $R_1$]

| Compound No. | Variable Definitions |
|---|---|
| 1 | $R^4$ = —OCH$_3$<br>$R^1$, $R^2$, $R^3$, $R^4$, $R^5$, $R^6$, $R^7$, $R^8$, $R^9$, $R^{12}$, $R^{13}$, and $R^{14}$ = H |
| 2 | $R^4$ = —OCD$_3$<br>$R^1$, $R^2$, $R^3$, $R^4$, $R^5$, $R^6$, $R^7$, $R^8$, $R^9$, $R^{12}$, $R^{13}$, and $R^{14}$ = D |
| 3 | $R^4$ = —OCH$_3$<br>$R^2$ and $R^3$ = D |
| 4 | $R^4$ = —OCH$_3$<br>$R^4$, $R^5$, $R^6$, and $R^7$ = D |
| 5 | $R^4$ = —OCH$_3$<br>$R^8$ and $R^9$ = D |
| 6 | $R^4$ = —OCH$_3$<br>$R^{12}$, $R^{13}$, and $R^{14}$ = D | wherein the compounds of Table 46 have an enantiomeric excess, with respect to the C—Z carbon, of at least 5%.

Table 47: The compounds corresponding to Table 46, wherein the abundance of deuterium in Z is at least 40% and the compounds have an enantiomeric excess, with respect to the C—Z carbon, of at least 5%. Table 48: The compounds corresponding to Table 46, wherein the abundance of deuterium in Z is at least 50% and the compounds have an enantiomeric excess, with respect to the C—Z carbon, of at least 5%. Table 49: The compounds corresponding to Table 46, wherein the abundance of deuterium in Z is at least 60% and the compounds have an enantiomeric excess, with respect to the C—Z carbon, of at least 5%. Table 50: The compounds corresponding to Table 46, wherein the abundance of deuterium in Z is at least 70% and the compounds have an enantiomeric excess, with respect to the C—Z carbon, of at least 5%. Table 51: The compounds corresponding to Table 46, wherein the abundance of deuterium in Z is at least 80% and the compounds have an enantiomeric excess, with respect to the C—Z carbon, of at least 5%. Table 52: The compounds corresponding to Table 46, wherein the abundance of deuterium in Z is at least 90% and the compounds have an enantiomeric excess, with respect to the C—Z carbon, of at least 5%. Table 53: The compounds corresponding to Table 46, wherein the abundance of deuterium in Z is at least 97% and the compounds have an enantiomeric excess, with respect to the C—Z carbon, of at least 5%. Table 54: The compounds corresponding to Table 46, wherein the abundance of deuterium in Z is about 100% and the compounds have an enantiomeric excess, with respect to the C—Z carbon, of at least 5%.

Another aspect of the invention provides a deuterium-enriched compound, said compound being a compound described herein where a hydrogen atom present in said compound is optionally replaced by D (e.g., the position is enriched as described for variable Z).

The invention is based, in part, on stabilizing 2,4-thiazolidinediones and via deuteration at the 5-position. The C-D bond at the 5-position is stronger than the naturally occurring C—H bond. The 5-deuterium is expected to slow the racemization of the stereogenic center at the 5-position.

Hydrogen atoms are present in the deuterium-enriched compounds of the invention. As such, the present deuterium-enriched compounds can be further enriched beyond the 5-position. For example, in formula I the $R^1$-$R^{11}$ can either be substituted with D (e.g., the phenyl ring) or fully replaced by D (e.g., $R^{11}$). Additional enrichment of the compounds of the invention can include enrichment at one additional position or multiple positions. Examples of this enrichment include (a) at least 10%, (b) at least 20%, (c) at least 30%, (d) at least 40%, (e) at least 50%, (f) at least 60%, (g) at least 70%, (h) at least 80%, (i) at least 90%, (j) at least 95%, (k) at least 97%, and (l) about 100%. The percentage enriched can correspond to one single position (e.g., 10% of $R^2$=D) or a group of positions (e.g., 10% of the $R^2$ and $R^3$ positions=D).

For other compounds of the invention, enrichment beyond the 5-position includes the presence of at least one additional deuterium. For example, enrichment can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc., up to the total number of hydrogen atoms present and depending on the number of hydrogens present.

In another aspect, the invention provides isolated or purified compounds. The isolated or purified compound is a group of molecules (e.g., an isolated compound) whose deuterium levels are above the naturally occurring levels. The isolated or purified compounds of the invention can be obtained by techniques known to those of skill in the art.

Isolated means that the non-naturally occurring compound is purified (e.g., from the reaction solution in which it was prepared). Examples of the purity of the isolated compound (could be more than one type of compound) include, but are not limited to, at least 50%, 55%, 60%, 65%, 70%, 75%, 80%, 85%, 90%, 95%, to 100% with respect to non-deuterium-enriched components being present.

In another aspect, the invention provides a mixture of compounds, which means that more than one type of deuterated compound is being claimed.

In another aspect, the invention provides compositions comprising deuterium-enriched compounds of the invention. The compositions require the presence of a compound of the invention that is greater than its natural abundance. For example, the compositions of the invention can comprise (a) a μg of a compound of the invention; (b) from 1-10 μg; (c) a mg; (d) from 1-10 mg; (e) a gram; (f) from 1-10 grams; (g) from 1-100 grams; and, (h) a kg.

In another aspect, the invention provides an amount of a novel compound of the invention. Examples of amounts include, but are not limited to (a) at least 0.01, 0.02, 0.03, 0.04, 0.05, 0.1, 0.2, 0.3, 0.4, 0.5, to 1 mole, (b) at least 0.1 moles, and (c) at least 1 mole of the compound. The present amounts also cover lab-scale (e.g., gram scale including 1, 2, 3, 4, 5 g, etc.), kilo-lab scale (e.g., kilogram scale including 1, 2, 3, 4, 5 kg, etc.), and industrial or commercial scale (e.g., multi-kilogram or above scale including 100, 200, 300, 400, 500 kg, etc.) quantities as these will be more useful in the actual manufacture of a pharmaceutical. Industrial/commercial scale refers to the amount of product that would be produced in a batch that was designed for clinical testing, formulation, sale/distribution to the public, etc.

In another aspect, the invention provides pharmaceutical compositions, comprising: a pharmaceutically acceptable carrier and a therapeutically effective amount of a deuterium-enriched compound described herein.

In another aspect, the invention provides pharmaceutical compositions, comprising: a pharmaceutically acceptable carrier and a deuterium-enriched compound described herein.

II. EXEMPLARY GENERAL PROCEDURES FOR SYNTHESIS OF DEUTERIUM-ENRICHED COMPOUNDS

Hydrogens present on the 5-deuterium-enriched 2,4-thiazolidinediones of the invention have different capacities for exchange with deuterium. For example, the hydrogen atom for Z is exchangeable under basic conditions (e.g., NaOD) in the presence of $D_2O$. Amino hydrogen atom, $R^1$, is exchangeable in $H_2O/D_2O$. The remaining non-hydroxy and non-amino hydrogen atoms are not easily exchangeable for deuterium atoms, though some may be depending on the specific moieties selected (e.g., hydrogens adjacent to carbonyl groups are expected to be base exchangeable). Deuterium atoms may be incorporated into non-exchangeable positions by the use of deuterated starting materials or intermediates via the known synthetic methods for the synthesis of 2,4-thiazolidinediones (e.g., 5-[4-[2-(5-ethyl-2-pyridyl)-2-oxoethoxy]benzyl]-5-deutero-thiazolidine-2,4-dione and 5-{4-[2-(3-methoxyphenyl)-2-oxoethoxy]benzyl}-1,3-thiazolidine-2,4-dione), as described in U.S. Pat. Nos. 5,441,971, 8,067,450, and 8,389,556, the contents of which are incorporated in their entirety herein by reference. Alternatively, deuterium is expected to be incorporated at the exchangeable and acidic positions of the final compound (e.g., 5-position).

Scheme 1 below provides an exemplary synthetic route for preparing deuterium-enriched compounds of the invention.

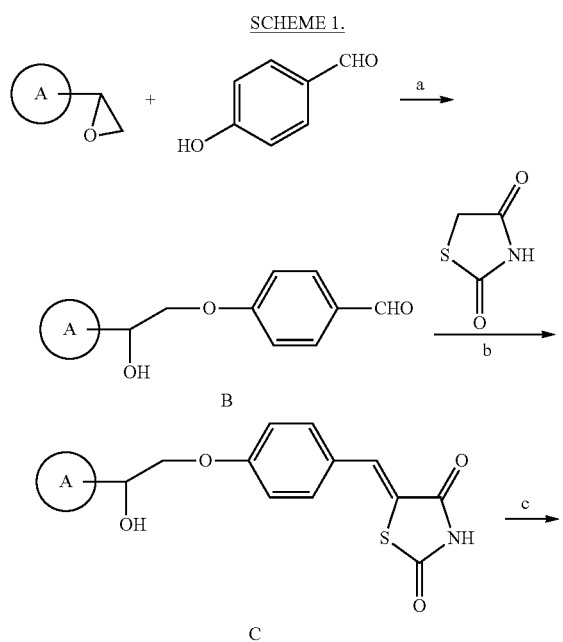

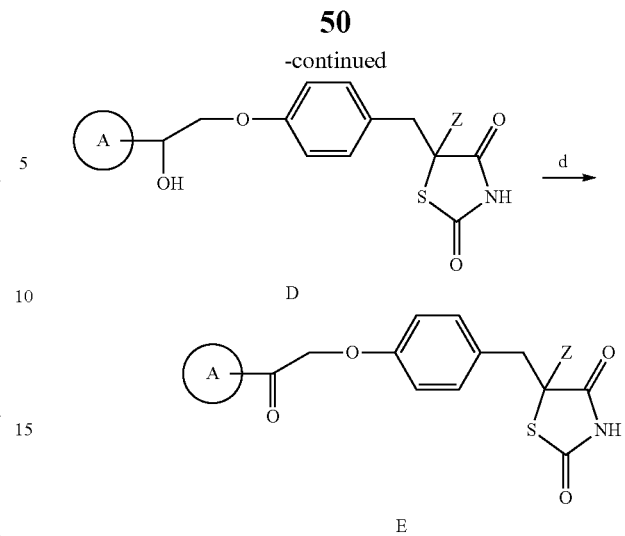

The compounds of the invention can be obtained by starting with a coupling of an epoxy-substituted ring A with 4-hydroxy-benzaldehyde under basic conditions (e.g., aq. NaOH) to provide intermediate B. Starting with deuterium-enriched epoxy-substituted ring A and/or 4-hydroxy-benzaldehyde (e.g., a deuterated aldehyde group CDO allows for $R^2$=D) provides an entry point to some of the deuterated compounds of the invention. Intermediate B can be reacted with 2,4-thiazolidinedione in the presence of a base (e.g., pyrrolidine) to provide alkenyl-intermediate C. Reduction of the alkenyl moiety (e.g., $NaBH_4/CoCl_2$) provides compound D, which can be a final product. Deuterium can be introduced at methylene and Z by reduction with a deuterating agent (e.g., $NaBD_4$). Alternatively, if the Z group of compound D is H, it can be exchangeable under basic conditions (e.g., NaOD) in the presence of $D_2O$ to provide Z=D. If a carbonyl group for $CR^{10}R^{11}$ is desired, then compound D can be oxidized (e.g., $P_2O_5$) to provide compound E. Once again, if Z=H, it can be exchangeable under basic conditions (e.g., NaOD) in the presence of $D_2O$ to provide Z=D.

Scheme 2 provides an alternative route to prepare pyridyl-containing deuterium-enriched compounds of the invention.

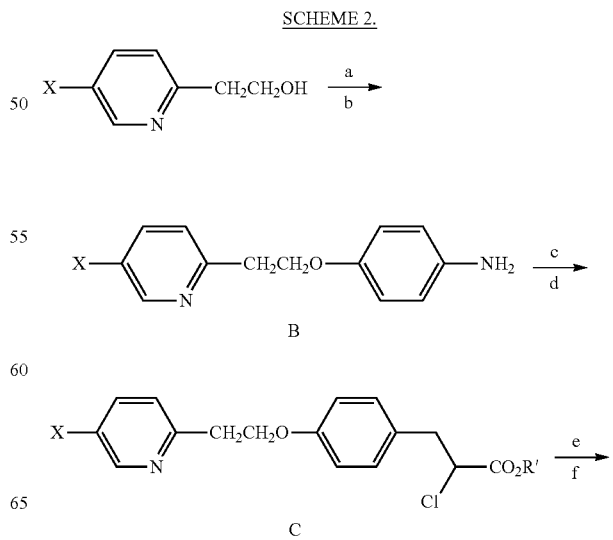

-continued

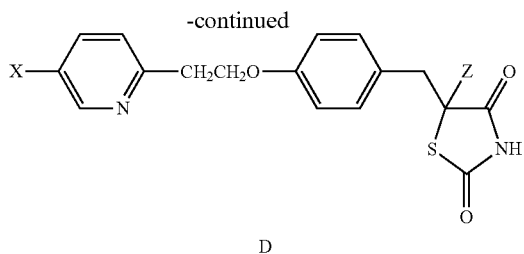

D

In Scheme 2, the starting pyridyl group can be prepared by reacting an appropriately substituted 2-methyl pyridine with formalin. The X group can be a protected hydroxylmethyl group (e.g., $CH_3OCH_2OCH_2$-prepared by reaction with chloromethyl methyl ether). X can also be a protected 1-hydroxy-ethyl group (e.g., $CH_3(CH_3OCH_2O)CH$-prepared by reaction with chloromethyl methyl ether). Intermediate B is formed by first reacting the starting pyridine with 4-fluoro-nitrobenzene in the presence of a base (e.g., NaH)(reaction a), followed by catalytic reduction (e.g., $H_2$ and Pd/C)(reaction b). Halo-ester C can be formed by first subjecting B to diazotization in the presence of HCl (or other halide)(reaction c), followed by the Meerwein arylation with an acrylic acid or ester (reaction d). The thiazolidinedione can be formed by reacting C with thiourea (reaction e), followed by acid hydrolysis (reaction f). The acid hydrolysis will typically remove the protecting group from X to yield the hydroxy-methyl or 1-hydroxy-ethyl moieties. If an acyl group is desired, the 1-hydroxy-ethyl group can be oxidized. If an acid group is desired, the starting hydroxyl-methyl group can be converted to a cyano through its corresponding chloromethyl moiety. The cyano group should then be converted to a carboxyl group when the above acid hydrolysis is performed. If the Z group of compound D is H, it can be exchangeable under basic conditions (e.g., NaOD) in the presence of $D_2O$ to provide Z=D.

Scheme 2 provides numerous entry points for deuteration. The starting pyridine (and optionally its substituents) can be deuterium-enriched, as can be the formalin used to chain lengthen the pyridine. In reaction a, the 4-fluoro-nitrobenzene ring can be deuterium-enriched. The acrylic acid/ester of reaction d can be deuterated.

If a racemic starting material (e.g., Z=D) is used or if stereospecificity is lost during a reaction, the resulting deuterated racemic mixture should be separable using known isolation techniques (e.g., chiral chromatography or crystallization).

III. THERAPEUTIC APPLICATIONS

The invention provides methods of using deuterium-enriched compounds described herein to treat medical disorders. The deuterium-enriched compound can be, for example, a compound of formula I or one of the other deuterium-enriched compounds described in Section I above. The therapeutic method comprises administering to a patient in need thereof a therapeutically effective amount of a deuterium-enriched compound described herein to treat the disorder. Various aspects of the invention pertaining to treating medical disorders is described below.

Treating Neurological Disorders

Accordingly, one aspect of the invention provides a method of treating a neurological disorder selected from the group consisting of Alzheimer's disease, Parkinson's disease, amyotrophic lateral sclerosis, Friedreich's ataxia, autism spectrum disorder, depression, mild cognitive impairment, neurodegeneration, adrenoleukodystrophy, Huntington's disease, stroke, traumatic brain injury, substance abuse, spinal cord injury, neuronal injury, and major depression or bipolar disorder comorbid with metabolic syndrome. The method comprises administering to a patient in need thereof a therapeutically effective amount of a deuterium-enriched compound described herein, such as a compound of Formula I or Formula II, to treat the disorder. In certain embodiments, the neurological disorder is selected from the group consisting of Alzheimer's disease, Parkinson's disease, amyotrophic lateral sclerosis, Friedreich's ataxia, depression, mild cognitive impairment, neurodegeneration, adrenoleukodystrophy, and Huntington's disease. In certain other embodiments, the neurological disorder is Alzheimer's disease. In certain embodiments, the neurological disorder is Parkinson's disease. In certain other embodiments, the neurological disorder is neurodegeneration resulting from mitochondrial dysfunction.

In certain other embodiments, the neurological disorder is a cognitive disorder, such as cognitive impairment and/or memory impairment. The cognitive impairment may be, for example, cognitive impairment associated with Alzheimer's disease.

In certain embodiments, the substance abuse is one or more of alcohol craving, heroin dependence, and nicotine dependence.

Treating Cancer

Another aspect of the invention provides a method of treating cancer. The method comprises administering to a patient in need thereof a therapeutically effective amount of a deuterium-enriched compound described herein, such as a compound of Formula I or Formula II, to treat the cancer.

In certain embodiments, the cancer is lung cancer, hepatocellular carcinoma, astrocytoma, glioma, glioblastoma, meningioma, liver cancer, lymphoma, melanoma, multiple myeloma, pancreatic cancer, colorectal cancer, pituitary cancer, thyroid cancer, esophageal cancer, or prostate cancer. In certain embodiments, the cancer is non-small cell lung cancer or hepatocellular carcinoma.

In certain other embodiments, the cancer is brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, or uterine cancer. In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, biliary tract cancer, thyroid cancer, acral lentiginous melanoma, actinic keratosis, acute lymphocytic leukemia, acute myeloid leukemia, adenoid cystic carcinoma, adenoma, adenosarcoma, adenosquamous carcinoma, anal canal cancer, anal cancer, anorectal cancer, astrocytic tumor, Bartholin's gland carcinoma, basal cell carcinoma, biliary cancer, bone cancer, bone marrow cancer, bronchial cancer, bronchial gland carcinoma, carcinoid, cholangiocarcinoma, chorioid plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangioblastoma, hemangioendothelioma, hemangioma, hepatic adenoma, hepatic adenomatosis, hepatobiliary cancer, hepatocellular carcinoma, Hodgkin's disease, ileum cancer, insulinoma, intraepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanoma, lymphoma, male genital cancer, malignant melanoma, malignant mesothelial tumor, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma, nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumor, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T-cell leukemia, tongue cancer, undifferentiated carcinoma, ureter cancer, urethral cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

In certain other embodiments, the cancer is non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

Treating Respiratory Disorders

Another aspect of the invention provides a method of treating a respiratory disorder. The method comprises administering to a patient in need thereof a therapeutically effective amount of a deuterium-enriched compound described herein, such as a compound of Formula I or Formula II, to treat the disorder. In certain embodiments, the deuterium-enriched compound is a compound described herein having the (S)-stereochemical configuration at the stereocenter of the thiazolidine-2,4-dione ring. In certain embodiments, the deuterium-enriched compound is a compound of Formula I. In certain other embodiments, the deuterium-enriched compound is a compound of Formula II.

In certain embodiments, the deuterium-enriched compound is administered by pulmonary administration. In a more specific embodiment, the deuterium-enriched compound is a compound described herein having the (S)-stereochemical configuration at the stereocenter of the thiazolidine-2,4-dione ring, and said compound is administered by pulmonary administration. In another more specific embodiment, the deuterium-enriched compound is a compound of Formula I and said compound is administered by pulmonary administration.

In certain embodiments, the deuterium-enriched compound is administered by routes other than pulmonary administration. In certain embodiments, the deuterium-enriched compound is administered by oral administration, sublingual administration, sublabial administration, rectal administration, injection, or transdermal administration. In certain embodiments, the deuterium-enriched compound is administered by intranasal administration. In certain embodiments, the deuterium-enriched compound is a compound of Formula I. In certain other embodiments, the deuterium-enriched compound is a compound of Formula II.

In certain embodiments, the respiratory disorder is chronic obstructive pulmonary disease, asthma, bronchitis, cystic fibrosis, pulmonary edema, pulmonary embolism, pulmonary arterial hypertension, pneumonia, pulmonary sarcoidosis, silicosis, pulmonary fibrosis, respiratory failure, acute respiratory distress syndrome, emphysema, chronic bronchitis, tuberculosis, lung cancer, or a chronic respiratory condition. In certain embodiments, the respiratory disorder is chronic obstructive pulmonary disease, asthma, or a chronic respiratory condition. In certain other embodiments, the respiratory disorder is chronic obstructive pulmonary disease. In yet other embodiments, the respiratory disorder is bronchitis, cystic fibrosis, pulmonary edema, pulmonary embolism, pneumonia, pulmonary sarcoidosis, silicosis, pulmonary fibrosis, respiratory failure, acute respiratory distress syndrome, emphysema, chronic bronchitis, tuberculosis, or lung cancer. In certain embodiments, the asthma is mild asthma, moderate asthma, severe asthma, or steroid-resistant asthma. In certain other embodiments, the respiratory disorder is chronic rhinosinusitis.

Treating Metabolic Disorders

Another aspect of the invention provides a method of treating a metabolic disorder selected from the group consisting of non-alcoholic fatty liver disease, diabetic retinopathy, diabetic neuropathy, diabetic nephropathy, beta cell depletion insulin resistance in a patient with congenital adrenal hyperplasia treated with a glucocorticoid, dysmetabolism in peritoneal dialysis patients, reduced insulin secretion, improper distribution of brown fat cells and white fat cells, obesity, or improper modulation of leptin levels. The method comprises administering to a patient in need thereof a therapeutically effective amount of a deuterium-enriched compound described herein, such as a compound of Formula I or Formula II, to treat the disorder. In certain embodiments, the deuterium-enriched compound is a compound of Formula I. In certain other embodiments, the deuterium-enriched compound is a compound of Formula II. In certain embodiments, the metabolic disorder is further selected from a complication of diabetes. In certain embodiments, the metabolic disorder is non-alcoholic fatty liver disease, diabetic retinopathy, diabetic neuropathy, diabetic nephropathy, beta cell depletion, reduced insulin secretion, improper distribution of brown fat cells and white fat cells, obesity, or improper modulation of leptin levels. In certain other embodiments, the metabolic disorder is non-alcoholic fatty liver disease. In certain other embodiments, the metabolic disorder is beta cell loss treatable by B-cell regeneration. In yet other embodiments, the metabolic disorder is Prader Willi syndrome.

Treating a Symptom of Hepatitis

Another aspect of the invention provides a method of treating a symptom of hepatitis. The method comprises administering to a patient in need thereof a therapeutically effective amount of a deuterium-enriched compound described herein, such as a compound of Formula I or Formula II, to treat a symptom of hepatitis. In certain embodiments, the deuterium-enriched compound is a compound of Formula I. In certain other embodiments, the deuterium-enriched compound is a compound of Formula II Treating Cardiovascular Disease Another aspect of the invention provides a method of treating a cardiovascular disease. The method comprises administering to a patient in need thereof a therapeutically effective amount of a deuterium-enriched compound described herein, such as a compound of Formula I or Formula II, to treat the cardiovascular disease. In certain embodiments, the deuterium-enriched compound is a compound of Formula I. In certain other embodiments, the deuterium-enriched compound is a compound of Formula II. In certain embodiments, the cardiovascular disease is hypertension, hyperlipidemia, atherosclerosis, improper vascular function, dyslipidemia, stenosis, restenosis, myocardial infarction, stroke, intracranial hemorrhage, acute coronary syndrome, stable angina pectoris, or unstable angina pectoris. In certain other embodiments, the cardiovascular disorder is intracranial hemorrhage, acute coronary syndrome, stable angina pectoris, or unstable angina pectoris.

In another aspect, the invention provides a method for preventing stroke in a patient. The method comprises administering to a patient in need thereof a therapeutically effective amount of a deuterium-enriched compound described herein, such as a compound of Formula I or Formula II, to prevent said stroke.

The method of treatment or the method of prevention may involve a patient at risk for central nervous system ischemic stroke, or may involve a patient at risk for stroke due to cardiovascular disease.

Reducing the Amount of a Triglyceride or Low-Density Lipoprotein

Another aspect of the invention provides a method of reducing the amount of a triglyceride or low-density lipoprotein (LDL) in a patient. The method comprises administering to a patient in need thereof an effective amount of a deuterium-enriched compound described herein, such as a compound of Formula I or Formula II, to reduce the amount of a triglyceride or LDL in the patient. In certain embodiments, the deuterium-enriched compound is a compound of Formula I. In certain other embodiments, the deuterium-enriched compound is a compound of Formula II.

In certain embodiments, the method provides a reduction of at least 1%, 5%, 10%, or 25% in the amount of a triglyceride or low-density lipoprotein (LDL) in the patient.

Increasing the Amount of High-Density Lipoprotein

Another aspect of the invention provides a method of increasing the amount of high-density lipoprotein (HDL) in a patient. The method comprises administering to a patient in need thereof a therapeutically effective amount of a deuterium-enriched compound described herein, such as a compound of Formula I or Formula II, to increase the amount of HDL in the patient. In certain embodiments, the deuterium-enriched compound is a compound of Formula I. In certain other embodiments, the deuterium-enriched compound is a compound of Formula II.

In certain embodiments, the method provides an increase of at least 1%, 5%, 10%, or 25% in the amount of high-density lipoprotein (HDL) in a patient.

Treating an Inflammatory or Immune-Mediated Disorder

Another aspect of the invention provides a method of treating an inflammatory or immune-mediated disorder selected from the group consisting of chronic kidney disease, arthritis, a primary cicatricial alopecia, lung fibrosis, multiple sclerosis, endotoxemia, sepsis, septic shock, laminitis, inflammatory bowel disease, colitis, Crohn's disease, rheumatoid arthritis, lupus, myasthenia gravis, vasculitis, chronic pancreatitis, a hyperproliferative skin disorder, an inflammatory skin disorder, and a dermatological condition. The method comprises administering to a patient in need thereof a therapeutically effective amount of a deuterium-enriched compound described herein, such as a compound of Formula I or Formula II, to treat the disorder. In certain embodiments, the deuterium-enriched compound is a compound of Formula I. In certain other embodiments, the deuterium-enriched compound is a compound of Formula II. In certain embodiments, the inflammatory or immune-mediated disorder is selected from the group consisting of chronic kidney disease, arthritis, a primary cicatricial alopecia, lung fibrosis, multiple sclerosis, endotoxemia, sepsis, septic shock, laminitis, inflammatory bowel disease, colitis, Crohn's disease, rheumatoid arthritis, lupus, myasthenia gravis, vasculitis, chronic pancreatitis, a hyperproliferative skin disorder, an inflammatory skin disorder, and a dermatological condition. In certain embodiments, the chronic kidney disease may be, for example, polycystic kidney disease (such as autosomal dominant or autosomal recessive). In certain other embodiments, the invention provides a method of treating an inflammatory disorder. In certain embodiments, the inflammatory disorder is polycystic kidney disease. In certain embodiments, the inflammatory disorder is chronic rhinosinusitis.

Treating a Dermatological Disorder

Another aspect of the invention provides a method of treating a dermatological disorder selected from the group consisting of psoriasis, atopic dermatitis, acne, leukoplakia, scleroderma, and a skin malignancy. The method comprises administering to a patient in need thereof a therapeutically effective amount of a deuterium-enriched compound described herein, such as a compound of Formula I or Formula II, to treat the disorder. In certain embodiments, the deuterium-enriched compound is a compound of Formula I. In certain other embodiments, the deuterium-enriched compound is a compound of Formula II.

Modulating Expression of Pro-Inflammatory Cytokines

Another aspect of the invention provides a method of modulating expression of a pro-inflammatory cytokine (e.g., TNF-$\alpha$, IL-1$\beta$, or IL-6) in a patient suffering from an inflammatory disorder. The method comprises administering to a patient in need thereof an effective amount of a deuterium-enriched compound described herein, such as a compound of Formula I or Formula II, to modulate expression of the pro-inflammatory cytokine. In certain embodiments, the pro-inflammatory cytokine is TNF-$\alpha$. In certain embodiments, the deuterium-enriched compound is a compound of Formula I. In certain other embodiments, the deuterium-enriched compound is a compound of Formula II.

Another aspect of the invention provides a method of modulating expression of an anti-inflammatory cytokine in a patient suffering from an inflammatory disorder. The method comprises administering to a patient in need thereof an effective amount of a deuterium-enriched compound described herein, such as a compound of Formula I or Formula II, to modulate expression of the anti-inflammatory cytokine. In certain embodiments, the deuterium-enriched compound is a compound of Formula I. In certain other embodiments, the deuterium-enriched compound is a compound of Formula II.

Modulating Macrophage Function

Another aspect of the invention provides a method of modulating macrophage function in a patient suffering from an infection. The method comprises administering to a patient in need thereof an effective amount of a deuterium-enriched compound described herein, such as a compound of Formula I or Formula II, to modulate macrophage function. In certain embodiments, the deuterium-enriched compound is a compound of Formula I. In certain other embodiments, the deuterium-enriched compound is a compound of Formula II.

Method of Promoting Wound Healing

Another aspect of the invention provides a method of promoting wound healing. The method comprises administering to a patient in need thereof a therapeutically effective amount of a deuterium-enriched compound described herein, such as a compound of Formula I or Formula II, to promote wound healing. In certain embodiments, the deuterium-enriched compound is a compound of Formula I. In certain other embodiments, the deuterium-enriched compound is a compound of Formula II.

Treating Skin Defects

Another aspect of the invention provides a method of treating skin defects caused by exposure to ultraviolet radiation. The method comprises administering to a patient in need thereof a therapeutically effective amount of a deuterium-enriched compound described herein, such as a compound of Formula I or Formula II, to treat skin defects caused by exposure to ultraviolet radiation. In certain embodiments, the deuterium-enriched compound is a compound of Formula I. In certain other embodiments, the deuterium-enriched compound is a compound of Formula II.

Method of Modulating Stem Cell Differentiation

Another aspect of the invention provides a method of modulating stem cell differentiation, such as in a patient. The method comprises exposing a stem cell to a deuterium-enriched compound described herein, such as a compound of Formula I or Formula II, is a compound of Formula I. In certain other embodiments, the deuterium-enriched compound is a compound of Formula II. In certain embodiments, the method modulates stem cell differentiation in a patient by administering to the patient an effective amount of a compound herein, such as a compound of Formula I or Formula II.

Preventing Medical Disorders

Also provided are methods of preventing a medical disorder in a patient. The method comprises administering to a patient in need thereof an effective amount of a deuterium-enriched compound described herein, such as a compound of Formula I or Formula II, to prevent the medical disorder. The medical disorder may be one or more of the medical disorders recited above, such as a neurological disorder (e.g., Alzheimer's disease or Parkinson's disease), cancer (e.g., non-small cell lung cancer or hepatocellular carcinoma), a metabolic disorder, a cardiovascular disorder (e.g. in-stent renarrowing in diabetes patients, reinfarction in diabetes patients, or cardiac allograft vasculopathy after heart transplant), or a respiratory disorder (e.g., chronic obstructive pulmonary disease).

Additional Medical Uses

Also provided are methods of using compounds herein for therapy comprising regenerative medicine. Also provided are methods of treating veterinary disorders, such as laminitis, using a compound described herein, such as a compound of Formula I or Formula II, to treat the veterinary disorder.

Manufacture of Medicaments

Another aspect of the invention provides for the use of a deuterium-enriched compound described herein in the manufacture of a medicament. The medicament may be for treating one or more of the medical disorders described herein, such as treating a neurological disorder (e.g., Alzheimer's disease or Parkinson's disease), cancer (e.g., non-small cell lung cancer or hepatocellular carcinoma), a metabolic disorder, or a respiratory disorder (e.g., chronic obstructive pulmonary disease).

Further Aspects of Medical Therapy

In another aspect, the invention provides a pharmaceutical composition useful for treating metabolic mediated disease, comprising: a deuterium-enriched compound of the invention or a pharmaceutically acceptable salt or stereoisomer thereof and one or more agents having antidiabetic activity and a pharmaceutically acceptable carrier. Examples of agents include metformin, DPP-4 inhibitors, or combinations thereof.

In another aspect, the invention provides a pharmaceutical composition useful for treating metabolic mediated disease, comprising a deuterium-enriched compound of the invention or a pharmaceutically acceptable salt or stereoisomer thereof, an second agent, and a pharmaceutically acceptable carrier, wherein the second agent is selected from: metformin; dipeptidyl peptidase IV (DPP-4) inhibitors (e.g., sitagliptin, and vildagliptin); statins (HMG-CoA reductase inhibitor)(e.g., atorvastatin, cerivastatin, fluvastatin, lovastatin, mevastatin, simvastatin, rosuvastatin, pravastatin, and combinations thereof); GLP-1 and -2 agonists including liraglutide and lixisenatide; SGLT2 inhibitors or combinations thereof; and anti-obesity drugs including Qsymia, Lorcaserin, Orlistat, Opioid receptor antagonists, Bupropion, Contrave, or combinations thereof.

In another aspect, the invention provides a pharmaceutical composition further comprising a diuretic selected from hydrochlorothiazide, chlorothaladone, chlorothiazide, or any combination thereof; a statin selected from atorvastatin, cerivastatin, fluvastatin, lovastatin, mevastatin, simvastatin, rosuvastatin, pravastatin, or any combination thereof; an angiotensin II receptor blocker selected from losartan, olmesartan, telmisartan, or any combination thereof; an ACE inhibitor selected from ramipril, captopril, enalapril, or any combination thereof; calcium channel blocker selected from amlodipine; or combination thereof.

In another aspect, the invention provides a pharmaceutical composition, further comprising: a diuretic selected from hydrochlorothiazide, chlorothaladone, chlorothiazide, or any combination thereof.

In another aspect, the invention provides a pharmaceutical composition, further comprising: a statin selected from atorvastatin, cerivastatin, fluvastatin, lovastatin, mevastatin, simvastatin, rosuvastatin, pravastatin, or any combination thereof.

In another aspect, the invention provides a pharmaceutical composition, further comprising: an angiotensin II receptor blocker selected from losartan, olmesartan, telmisartan, or any combination thereof.

In another aspect, the invention provides a pharmaceutical composition, further comprising: an ACE inhibitor selected from ramipril, captopril, enalapril, or any combination thereof; calcium channel blocker selected from amlodipine; or combination thereof.

In another aspect, the invention provides a pharmaceutical composition, further comprising: a glucocorticoid agonist selected from cortisone, hydrocortisone, prednisone, prednisolone, methylprednisolone, betamethasone, triamcinolone, or any combination thereof.

In another aspect, the invention provides an amount of a deuterium-enriched compound of the invention as described above for use in therapy.

In another aspect, the invention provides the use of an amount of a deuterium-enriched compound of the invention for the manufacture of a medicament.

In another aspect, the invention provides methods of treating various diseases or disorders using a deuterium-enriched compound provided herein, or a pharmaceutically acceptable salt or stereoisomer thereof.

Without being limited by a particular theory, in general, the invention relates to insulin sensitizers that have reduced binding to and activation of the nuclear transcription factor PPARγ. Traditional insulin sensitizers activate PPARγ and stimulate the transcription of genes that favor sodium re-absorption. The insulin sensitizers of this invention have reduced binding and activation of the nuclear transcription factor PPARγ and therefore produce reduced sodium re-absorption and fewer dose-limiting side effects. Thus, these compounds are substantially more effective to treat and prevent diabetes and other metabolic inflammation mediated diseases including all aspects of insulin resistance associated with metabolic syndrome including dyslipidemia, and central obesity. These compounds are also useful for treating other inflammatory diseases such as rheumatoid arthritis, lupus, myasthenia gravis, vasculitis, Chronic Obstructive Pulmonary Disease (COPD), nonalcoholic fatty liver disease (NAFLD), nonalcoholic steatohepatitis (NASH), and inflammatory bowel disease as well as neurodegenerative diseases such as Alzheimer's disease, Parkinson's disease, and multiple sclerosis. In certain embodiments, the inflammatory disease is chronic rhinosinusitis.

In another aspect, the invention provides methods of treating, a metabolic inflammation mediated disease, comprising: administering a therapeutically effective amount of a deuterium-enriched compound provided herein, or a pharmaceutically acceptable salt or stereoisomer thereof.

In another aspect, the invention provides methods of treating a metabolic inflammation mediated disease, comprising: administering a therapeutically effective amount of a deuterium-enriched compound provided herein, or a pharmaceutically acceptable salt or stereoisomer thereof, wherein the disease is selected from diabetes (e.g., Type I diabetes, Type II diabetes, insulin resistance, and inadequate glucose tolerance) and other metabolic inflammation mediated diseases (e.g., insulin resistance associated with metabolic syndrome including dyslipidemia, and central obesity).

In another aspect, the invention provides methods of treating a metabolic inflammation mediated disease, comprising: administering a therapeutically effective amount of a deuterium-enriched compound provided herein, or a pharmaceutically acceptable salt or stereoisomer thereof, wherein the disease is selected from inflammatory diseases (e.g., rheumatoid arthritis, lupus, myasthenia gravis, vasculitis, Chronic Obstructive Pulmonary Disease (COPD), nonalcoholic fatty liver disease (NAFLD), nonalcoholic steatohepatitis (NASH), and inflammatory bowel disease) and neurodegenerative diseases (e.g., Alzheimer's disease, Parkinson's disease, and multiple sclerosis).

In another aspect, the invention provides a method of treating hypertension, comprising: administering a therapeutically effective amount of a deuterium-enriched compound provided herein, or a pharmaceutically acceptable salt or stereoisomer thereof, in combination with one or more antihypertensive agents including diuretics (e.g., hydrochlorothiazide, chlorothaladone, chlorothiazide, and combinations thereof), angiotensive converting enzyme inhibitors (ACE inhibitors)(e.g., ramipril, captopril, enalapril, and combinations thereof); angiotensin II receptor blockers (ARBs)(e.g., losartan, olmesartan, telmisartan, and combinations thereof); renin inhibitors; β-adrenergic receptor blockers; statins (e.g., atorvastatin, cerivastatin, fluvastatin, lovastatin, mevastatin, simvastatin, rosuvastatin, pravastatin, and combinations thereof); calcium channel blockers (e.g., amlodipine); and, combinations thereof.

In another aspect, the invention provides a method of lowering lipids, comprising: administering a therapeutically effective amount of a deuterium-enriched compound provided herein, or a pharmaceutically acceptable salt or stereoisomer thereof, in combination with one or more statins (e.g., atorvastatin, cerivastatin, fluvastatin, lovastatin, mevastatin, simvastatin, rosuvastatin, pravastatin, combinations thereof).

The invention may be embodied in other specific forms without departing from the spirit or essential attributes thereof. This invention encompasses all combinations of preferred aspects of the invention noted herein. It is understood that any and all aspects of the invention may be taken in conjunction with any other aspect or aspects to describe additional aspects. It is also to be understood that each individual element of the aspects is intended to be taken individually as its own independent aspect. Furthermore, any element of an aspect is meant to be combined with any and all other elements from any aspect to describe an additional aspect.

IV. DOSAGES, COMBINATION THERAPY, AND FORMULATIONS

Dosages of a compound provided herein, or stereoisomer or pharmaceutically acceptable salt thereof, vary depending on factors such as: specific indication to be treated and/or managed; age and condition of a patient; and amount of second active agent used, if any. Generally, a compound provided herein, or stereoisomer or pharmaceutically acceptable salt thereof, may be used in an amount of from about 0.1 mg to about 500 mg per day, and can be adjusted in a conventional fashion {e.g., the same amount administered each day of the treatment and/or management period), in cycles {e.g., one week on, one week off), or in an amount that increases or decreases over the course of treatment and/or management. In other aspects, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg.

Combination Therapy

A compound provided herein, or a pharmaceutically acceptable salt thereof, can be combined with other pharmacologically active compounds ("second active agents") in methods and compositions provided herein. Certain combinations may work synergistically in the treatment of particular types of diseases or disorders, and conditions and symptoms associated with such diseases or disorders. A compound provided herein, or a pharmaceutically acceptable salt thereof, can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

In certain embodiments, the combination therapy comprises a deuterium-enriched compound described herein and a second therapeutic agent for treating a metabolic disorder, such as metformin, a dipeptidyl peptidase IV inhibitor (e.g., sitagliptin, vildagliptin, or the like), a statin (e.g., a HMG-CoA reductase inhibitor, such as atorvastatin, cerivastatin, fluvastatin, lovastatin, mevastatin, simvastatin, rosuvastatin, pravastatin, or combination thereof), a GLP-1 agonist, a GLP-2 agonist, or an SGLT2 inhibitor. As appreciated, the combination therapy may comprising more than two therapeutic agents, such as where a combination of a deuterium-enriched compound described herein and at least two of the aforementioned agents for treating a metabolic disorder are administered to the patient.

In certain other embodiments, the combination therapy comprises a deuterium-enriched compound described herein and a diuretic agent, such as hydrochlorothiazide.

In certain other embodiments, the combination therapy comprises a deuterium-enriched compound described herein and a second therapeutic agent for treating hypertension, diabetes, or an inflammatory disorder. The second therapeutic agent may be one that limits the activity of the renin-angiotensin system, such as an angiotensin converting enzyme inhibitor (e.g., an ACE inhibitor, such as ramipril, captopril, enalapril, or the like), an angiotensin receptor blocker (e.g., candesartan, losartan, olmesartan, or the like), or a renin inhibitor. Alternatively, the second therapeutic agent may limit hypertension by alternate means, such as a beta-adrenergic receptor blocker or calcium channel blocker (e.g., amlodipine).

In certain other embodiments, the combination therapy comprises a deuterium-enriched compound described herein and a glucocorticoid agonist. Such combination therapy may be particularly useful for treating an inflammatory disorder, such as therapy for suppressing an immune response, preventing transplant rejection, and treating autoimmune disease. Exemplary disorders include, for example, rheumatoid arthritis, lupus, myasthenia gravis, muscular dystrophy vasculitis, multiple sclerosis, chronic obstructive pulmonary disease (COPD), inflammatory bowel disease, treatment of acute allergic reactions, and transplant rejection. In certain other embodiments, the combination therapy comprises a deuterium-enriched compound described herein and a second therapeutic agent for treating a kidney disease. Exemplary such second therapeutic agents include those that increase cAMP or comprise a beta-adrenergic agonist. Exemplary beta-adrenergic agonists include, for example, a beta-1-adrenergic agonist, a beta-2-adrenergic agonist, a beta-3-adrenergic agonist, or a combination thereof. In certain embodiments, the second therapeutic agent is noradrenaline, isoprenaline, dobutamine, salbutamol, levosalbutamol, terbutaline, pirbuterol, procaterol, metaproterenol, fenoterol, bitolterol mesylate, salmeterol, formoterol, bambuterol, clenbuterol, indacaterol, L-796568, amibegron, solabegron, isoproterenol, albuterol, metaproterenol, arbutamine, befunolol, bromoacetylalprenololmenthane, broxaterol, cimaterol, cirazoline, denopamine, dopexamine, epinephrine, etilefrine, hexoprenaline, higenamine, isoetharine, isoxsuprine, mabuterol, methoxyphenamine, nylidrin, oxyfedrine, prenalterol, ractopamine, reproterol, rimiterol, ritodrine, tretoquinol, tulobuterol, xamoterol, zilpaterol, zinterol, or a pharmaceutically acceptable salt thereof; or a combination of any of the foregoing.

In certain other embodiments, the combination therapy comprises a deuterium-enriched compound described herein and a second therapeutic agent for treating cancer. Exemplary second therapeutic agents for treating cancer include, for example, an alkylating agent, an anti-metabolite (i.e., a molecule that impedes DNA and/or RNA synthesis), an anti-microtubule agent, a topoisomerase inhibitor, a cytotoxic antibiotic, a tyrosine kinase inhibitor, an inhibitor of tumor necrosis factor alpha, anti-neoplastic radiation therapy, or a Programmed Death protein-1 (PD-1) modulator (e.g., an inhibitor). In certain embodiments, the second therapeutic agent for treating cancer is azacitidine, azathioprine, bleomycin, carboplatin, capecitabine, carmustine, cisplatin, chlorambucil, cyclophosphamide, cytarabine, dacarbazine, daunorubicin, docetaxel, doxifluridine, doxorubicin, epirubicin, epothilone, etoposide, fluorouracil, fulvestrant, gemcitabine, hydroxyurea, idarubicin, imatinib, lomustine, mechlorethamine, mercaptopurine, methotrexate, mitoxantrone, oxaliplatin, paclitaxel, pemetrexed, procarbazine, raloxifene, teniposide, temozolomide, tamoxifen, toremifene, valrubicin, vinblastine, vincristine, vindesine, vinorelbine, or a pharmaceutically acceptable salt thereof.

In yet other embodiments, the second therapeutic agent for treating cancer is abraxane; acivicin; aclarubicin; acodazole hydrochloride; acronine; adozelesin; aldesleukin; altretamine; albomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate: bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol: celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; portiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; a stem cell treatment; streptonigrin; streptozotocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; or zorubicin hydrochloride.

Formulations

Pharmaceutical compositions can be used in the preparation of individual, single unit dosage forms. Pharmaceutical compositions and dosage forms provided herein comprise a compound provided herein, or a pharmaceutically acceptable salt, solvate, or stereoisomer thereof. Pharmaceutical compositions and dosage forms can further comprise one or more excipients.

Pharmaceutical compositions and dosage forms provided herein can comprise one or more additional active ingredients. Examples of optional second, or additional, active ingredients are described above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., Remington's Pharmaceutical Sciences, 18th ed., Mack Publishing, Easton Pa. (1990).

In another aspect, the invention the pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In another aspect, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in another aspect, packaged using materials known to prevent exposure to water such that they can be included in suitable formulary kits. Examples of suitable packaging include, but are not limited to, hermetically sealed foils, plastics, dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In another aspect, dosage forms comprise a compound provided herein in an amount of from about 0.10 to about 500 mg. Examples of dosages include, but are not limited to, 0.1, 1, 2, 5, 7.5, 10, 12.5, 15, 17.5, 20, 25, 50, 100, 150, 200, 250, 300, 350, 400, 450, or 500 mg.

In another aspect, dosage forms comprise the second active ingredient in an amount of 1-about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In another aspect, the invention provides oral dosage forms that are tablets or capsules, in which case solid excipients are employed. In another aspect, the tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in another aspect, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In another aspect, pharmaceutical compositions comprise from about 0.5 to about 15 weight percent of disintegrant, or from about 1-about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a Syloid® silica gel (AEROSIL200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In another aspect, the invention provides a solid oral dosage form comprising a compound provided herein, anhydrous lactose, microcrystalline cellulose, polyvinylpyrrolidone, stearic acid, colloidal anhydrous silica, and gelatin.

Active ingredients provided herein can also be administered by controlled release means or by delivery devices that are well known to those of ordinary skill in the art. Examples include, but are not limited to, those described in U.S. Pat. Nos. 3,845,770; 3,916,899; 3,536,809; 3,598,123; and U.S. Pat. Nos. 4,008,719, 5,674,533, 5,059,595, 5,591,767, 5,120,548, 5,073,543, 5,639,476, 5,354,556, and 5,733,566, each of which is incorporated in its entirety herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In another aspect, the invention procies single unit dosage forms suitable for oral administration such as, but not limited to, tablets, capsules, gelcaps, and caplets that are adapted for controlled-release.

Controlled-release pharmaceutical products improve drug therapy over that achieved by their non-controlled counterparts. In another aspect, the invention provides the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another aspect, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In another aspect, in order to maintain a constant level of drug in the body, the drug can be released from the dosage form at a rate that will replace the amount of drug being metabolized and excreted from the body. Controller release of an active ingredient can be stimulated by various conditions including, but not limited to, pH, temperature, enzymes, water, or other physiological conditions or compounds.

Parenteral dosage forms can be administered to patients by various routes including, but not limited to, subcutaneous, intravenous (including bolus injection), intramuscular, and intraarterial. Administration of a parenteral dosage form bypasses patients' natural defenses against contaminants, and thus, in these aspects, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and nonaqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated in its entirety herein by reference.

Topical and mucosal dosage forms provided herein include, but are not limited to, sprays, aerosols, solutions, emulsions, suspensions, eye drops or other ophthalmic preparations, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In another aspect, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are nontoxic and pharmaceutically acceptable. Moisturizers or humectants can also be added to pharmaceutical compositions and dosage forms. Examples of additional ingredients are well known in the art. See, e.g., Remington's Pharmaceutical Sciences, 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other aspects, stearates can serve as a lipid vehicle for the formulation, as an emulsifying agent or surfactant, or as a delivery-enhancing or penetration-enhancing agent. In other aspects, salts, solvates, prodrugs, or stereoisomers of the active ingredients can be used to further adjust the properties of the resulting composition.

In another aspect, the active ingredients provided herein are not administered to a patient at the same time or by the same route of administration. In another aspect, provided are kits which can simplify the administration of appropriate amounts of active ingredients.

In another aspect, the invention provides a kit comprising a dosage form of a compound provided herein. Kits can further comprise additional active ingredients such as oblimersen (Genasense), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL-1β, Ara-C, vinorelbine, isotretinoin, 13-cis-retinoic acid, or a pharmacologically active mutant or derivative thereof, or a combination thereof. Examples of the additional active ingredients include, but are not limited to, those disclosed herein.

In other aspects, the kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

V. DEFINITIONS

The examples provided in the definitions section as well as the remainder of this application are non-inclusive unless otherwise stated. They include but are not limited to the recited examples.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the invention. Specifically, cis and trans geometric isomers of the compounds of the invention may also exist and may be isolated as a mixture of isomers or as separated isomeric forms. All processes used to prepare compounds of the invention and intermediates made therein are considered to be part of the invention. All tautomers of shown or described compounds are also considered to be part of the invention.

"Acyl" refers to formyl, alkylcarbonyl having 2 to 6 carbon atoms (e.g., acetyl, propionyl, isobutyryl, pentanoyl, isopentanoyl, and hexanoyl,), aralkylcarbonyl having 8 to 9 carbon atoms (e.g., phenylacetyl and phenylpropionyl), and arylcarbonyl having 7 to 8 carbon atoms (e.g., benzoyl and p-toluoyl). The aralkylcarbonyl and arylcarbonyl may have one or more substituents such as halogen (fluorine, chlorine, and bromine), lower alkoxy having 1 to 4 carbon atoms (methoxy and ethoxy), and trifluoromethyl.

The term "aliphatic" encompasses the terms alkyl, alkenyl, alkynyl, each of which being optionally substituted as set forth below.

An "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl) carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO$_2$-amino)alkyl), aminoalkyl, amidoalkyl, (cycloaliphatic)alkyl, or haloalkyl.

An "alkenyl" group refers to an aliphatic carbon group that contains 2-8 (e.g., 2-8, 2-6, or 2-4) carbon atoms and at least one double bond. Like an alkyl group, an alkenyl group can be straight or branched. Examples of an alkenyl group include, but are not limited to allyl, isoprenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic) carbonyl, (cycloaliphatic)carbonyl, or (heterocycloaliphatic) carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl) carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-SO$_2$—, cycloaliphatic-SO$_2$—, or aryl-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-SO$_2$-amino)alkenyl), aminoalkenyl, amidoalkenyl, (cycloaliphatic)alkenyl, or haloalkenyl.

An "alkynyl" group refers to an aliphatic carbon group that contains 2-8 (e.g., 2-8, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-SO$_2$—, aliphaticamino-SO$_2$—, or cycloaliphatic-SO$_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

An "amido" encompasses both "aminocarbonyl" and "carbonylamino". These terms when used alone or in connection with another group refer to an amido group such as —N($R^X$)—C(O)—$R^Y$ or —C(O)—N($R^X$)$_2$, when used terminally, and —C(O)—N($R^X$)— or —N($R^X$)—C(O)— when used internally, wherein $R^X$ and $R^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

An "amino" group refers to —NR$^X$R$^Y$ wherein each of R$^X$ and R$^Y$ is independently hydrogen, aliphatic, cycloaliphatic, (cycloaliphatic)aliphatic, aryl, aralphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—. R$^X$ has the same meaning as defined above.

An "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{3-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-SO$_2$— or amino-SO$_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl) aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

An "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

An "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, norbornyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, or bicyclo[2.2.2] octyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as phosphor, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-SO$_2$— and aryl-SO$_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholinyl, octahydrobenzofuryl, octahydrochromenyl, octahydrothiochromenyl, octahydroindolyl, octahydropyrindinyl, decahydroquinolinyl, octahydrobenzo[b]thiophenyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phosphor, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are pyridyl, 1H-indazolyl, furyl, pyrrolyl, thienyl, thiazolyl, oxazolyl, imidazolyl, tetrazolyl, benzofuryl, isoquinolinyl, benzothiazolyl, xanthenyl, thioxanthenyl, phenothiazinyl, dihydroindolyl, benzo[1,3]dioxolyl, benzo[b]furyl, benzo[b]thiophenyl, indazolyl, benzimidazolyl, purinyl, cinnolyl, quinolyl, quinazolyl, phthalazyl, quinazolyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thiazolyl, imidazolyl, pyrazolyl, isoxazolyl, isothiazolyl, 1,3,4-thiadiazolyl, 2H-pyranyl, 4H-pyranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, indazolyl, benzimidazolyl, benzothiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl)heteroaryl]; (sulfonyl)heteroaryl [e.g., (alkylsulfonyl)heteroaryl]; (hydroxyalkyl)heteroaryl; (alkoxyalkyl)heteroaryl; (hydroxy)heteroaryl; ((carboxy)alkyl)heteroaryl; (((dialkyl)amino)alkyl]heteroaryl; (heterocycloaliphatic)heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl)heteroaryl [e.g., (alkylcarbonyl)heteroaryl]; (alkyl)heteroaryl, and (haloalkyl)heteroaryl [e.g., trihaloalkylheteroaryl].

A "heteroaraliphatic (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, norbomanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, and 3-azabicyclo[3.2.1]octyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

An "aroyl" or "heteroaroyl" refers to an aryl-C(O)— or a heteroaryl-C(O)—. The aryl and heteroaryl portion of the aroyl or heteroaroyl is optionally substituted as previously defined.

An "alkoxy" group refers to an alkyl-O— group where "alkyl" has been defined previously.

As used herein, a "carbamoyl" group refers to a group having the structure —O—CO—$NR^XR^Y$ or —$NR^X$—CO—O—$R^Z$, wherein $R^X$ and $R^Y$ have been defined above and $R^Z$ can be aliphatic, aryl, aralphatic, heterocycloaliphatic, heteroaryl, or heteroaraliphatic.

As used herein, a "carboxy" group refers to —COOH, —$COOR^X$, —OC(O)H, —OC(O)$R^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —$CF_3$.

As used herein, a "mercapto" group refers to —SH.

As used herein, a "sulfo" group refers to —$SO_3H$ or —$SO_3R^X$ when used terminally or —$S(O)_3$— when used internally.

As used herein, a "sulfamide" group refers to the structure —$NR^X$—$S(O)_2$—$NR^YR^Z$ when used terminally and —$NR^X$—$S(O)_2$—$NR^Y$— when used internally, wherein $R^X$, $R^Y$, and $R^Z$ have been defined above.

As used herein, a "sulfonamide" group refers to the structure —$S(O)_2$—$NR^XR^Y$ or —$NR^X$—$S(O)_2$—$R^Z$ when used terminally; or —$S(O)_2$—$NR^X$— or —$NR^X$—$S(O)_2$— when used internally, wherein $R^X$, $R^Y$, and $R^Z$ are defined above.

As used herein a "sulfanyl" group refers to —S—$R^X$ when used terminally and —S— when used internally, wherein $R^X$ has been defined above. Examples of sulfanyls include aliphatic-S—, cycloaliphatic-S—, aryl-S—, or the like.

As used herein a "sulfinyl" group refers to —S(O)—$R^X$ when used terminally and —S(O)— when used internally, wherein $R^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —$S(O)_2$—$R^X$ when used terminally and —$S(O)_2$— when used internally, wherein $R^X$ has been defined above. Exemplary sulfonyl groups include aliphatic-$S(O)_2$—, aryl-$S(O)_2$—, (cycloaliphatic(aliphatic))-$S(O)_2$—, cycloaliphatic-$S(O)_2$—, heterocycloaliphatic-$S(O)_2$—, heteroaryl-$S(O)_2$—, (cycloaliphatic(amido(aliphatic)))-$S(O)_2$— or the like.

As used herein, a "sulfoxy" group refers to —O—SO—$R^X$ or —SO—O—$R^X$, when used terminally and —O—S(O)— or —S(O)—O— when used internally, where $R^X$ has been defined above.

As used herein, a "halogen" or "halo" group refers to fluorine, chlorine, bromine or iodine.

An "alkoxycarbonyl," which is encompassed by the term carboxy, used alone or in connection with another group refers to a group such as alkyl-O—C(O)—.

An "alkoxyalkyl" refers to an alkyl group such as alkyl-O-alkyl-, wherein alkyl has been defined above.

"Host" or "patient" typically refers to a human. It also includes other mammals including the equine, porcine, bovine, feline, and canine families.

"Therapeutically effective amount" includes an amount of a compound of the invention that is effective when administered alone or in combination to treat the desired condition or disorder. "Therapeutically effective amount" includes an amount of the combination of compounds claimed that is effective to treat the desired condition or disorder. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antiviral effect, or some other beneficial effect of the combination compared with the individual components.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. For example, such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, bisulfonic, carbonic, citric, edetic, ethanedisulfonic, ethanesulfonic, fumaric, glucoheptonic, gluconic, glutamic, glycolic, glycollyarsanilic, hexylresorcinic, hydrobromic, hydrochloric, hydroiodic, hydroxymaleic, hydroxynaphthoic, isethionic, lactic, lactobionic, lauric, laurylsulfonic, maleic, malic, mandelic, methanesulfonic, napsylic, naphthylic, nitric, oleic, oxalic, palmitic, pamoic, pantothenic, phenylacetic, phosphoric, polygalacturonic, propionic, salicylic, stearic, succinic, sulfamic, sulfanilic, sulfuric, tannic, tartaric, toluenesulfonic, and valeric. (See, for example, Berge et al. (1977) "Pharmaceutical Salts", J. Pharm. Sci. 66:1-19.)

When a compound of the invention is left in air or is recrystallized, it may absorb water or may have water attached on the surface and sometimes becomes a hydrate. In addition, compounds of the invention may absorb other solvents and form their solvates. Such solvates (including hydrates) are embraced in the invention and are included when reference is made to a compound or a pharmaceutically acceptable salt thereof.

"Treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder.

"Prevent," "preventing" and "prevention" refer to the prevention of the onset, recurrence or spread of a disease or disorder, or of one or more symptoms thereof.

"Manage," "managing" and "management" refer to preventing or slowing the progression, spread or worsening of a disease or disorder, or of one or more symptoms thereof. In certain cases, the beneficial effects that a subject derives from a prophylactic or therapeutic agent do not result in a cure of the disease or disorder.

"Prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, if a variable is not accompanied by a definition, then the previous definition of the variable controls.

EXAMPLES

The invention now being generally described, will be more readily understood by reference to the following examples, which are included merely for purposes of illustration of certain aspects and embodiments of the present invention, and are not intended to limit the invention.

Example 1

Preparation of racemic deuterated mitoglitazone, rac-5-({p-[2-(5-ethyl-2-pyridyl)-2-oxoethoxy]phenyl}methyl)-(5-$^2$H)-1,3-thiazolidine-2,4-dione Racemic deuterated mitoglitazone was prepared from racemic pioglitazone (i.e., rac-5-({p-[2-(5-ethyl-2-pyridyl)ethoxy]phenyl}methyl)-1,3-thiazolidine-2,4-dione) by oxidation of the ethoxy side chain to the alcohol. This intermediate was deuterated, and deuterated mitoglitazone was obtained by further oxidation of the alcohol to the ketone.

Step 1—Preparation of rac-2-(2-{4-[(2,4-dioxothiazolidin-5-yl)methyl]phenoxy}ethyl)-5-ethylpyridine-1-oxide

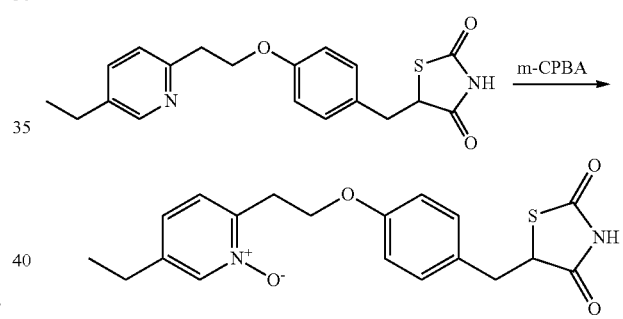

The hydrochloric acid salt of pioglitazone (3 g, 7.64 mmol) was dissolved in N,N-dimethylformamide (DMF, 50 mL) and neutralized by addition of an aqueous solution of sodium bicarbonate (NaHCO$_3$, 0.641 g, 7.64 mmol in 6 mL water). The reaction mixture was diluted with water and the white solid was filtered off. It was rinsed with water and dried under vacuum. The resulting solid was resuspended in dichloromethane (CH$_2$Cl$_2$), and meta-chloroperbenzoic acid (m-CPBA, 50% by weight, 2.64 g, 7.64 mmol) was added to the mixture while maintaining the temperature at about 10° C. The reaction mixture was stirred at room temperature for 2 days, and then one more equivalent of m-CPBA (2.64 g, 7.64 mmol) was added. The reaction mixture was stirred for 2 h, then diluted with CH$_2$Cl$_2$ (50 mL). The organic layer was washed with 10% Na$_2$S$_2$O$_3$ in water/water (2:1 v:v), then with 1:1 v:v 10% NaHCO$_3$ in water/water (1:1 v:v). The resulting organic mixture was dried over sodium sulfate, filtered and solvent evaporated to give the crude N-oxide, which was further purified by flash chromatography on silica gel (gradient elution: CH$_2$Cl$_2$/10% MeOH in CH$_2$Cl$_2$ from 9:1 to 1:1). Fractions containing the pure N-oxide were pooled and evaporated to give the title compound (1.313 g, 3.53 mmol, 46.2% yield). LC/MS: 373 (M+1)

Step 2—Synthesis of 5-({p-[2-(5-ethylpyridin-2-yl)-2-hydroxyethoxy]phenyl}methyl)-1,3-thiazolidine-2,4-dione

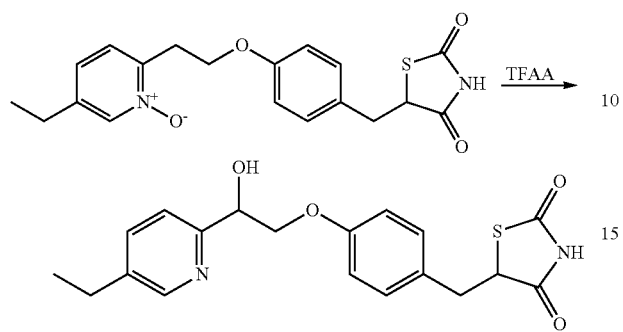

The N-oxide of racemic pioglitazone (935 mg, 2.54 mmol) was suspended in 12 mL CH$_2$Cl$_2$, then trifluoroacetic anhydride (TFAA, 1.49 mL, 12.69 mmol., 5 equiv.) was added and the reaction mixture was shaken at 50° C. After 24 h, an additional equivalent of TFAA was added and the vial was shaken for another 24 h. After the solvent and excess TFAA were evaporated, the resulting light yellow residue (1.922 g) was dissolved in 5 mL tetrahydrofuran (THF), and next a saturated NaHCO$_3$ aqueous solution was added until gas evolution stopped (4 mL). The resulting solution was diluted with water (10 mL) and the mixture extracted with ethyl acetate (EtOAc, 3×20 mL). The combined organic layers were dried over Na$_2$SO$_4$, filtered and evaporated to provide the alcohol in crude form. The crude alcohol was purified by preparative HPLC (0.1% TFA water/acetonitrile gradient). Fractions containing the pure product were neutralized by addition of triethylamine, combined, and evaporated to provide a residue. The residue was redissolved in EtOAc and the organic layer was washed with brine then dried over Na$_2$SO$_4$. Evaporation of the solvent gave pure 5-({p-[2-(5-ethylpyridin-2-yl)-2-hydroxyethoxy]phenyl}methyl)-1,3-thiazolidine-2,4-dione as a white foam (434.8 mg, 1.17 mmol, 46% yield). LC-MS: 373 (M+1).

Step 3—Synthesis of 5-({p-[2-(5-ethylpyridin-2-yl)-2-hydroxyethoxy]phenyl}methyl)-(5-2H)-1,3-thiazolidine-2,4-dione

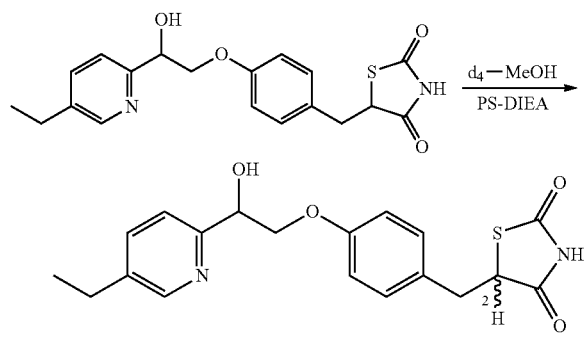

5-({p-[2-(5-Ethylpyridin-2-yl)-2-hydroxyethoxy]phenyl}methyl)-1,3-thiazolidine-2,4-dione (434.8 mg, 1.17 mmol) was dissolved in perdeuterated methanol (d$^4$-MeOH, 14.2 mL). Diethylisopropylamine on polystyrene resin (PS-DIEA, 3.68 mmol/g, 1.585 g, 5.835 mmol, 5 equiv.) was added, and the reaction mixture was shaken at room temperature for 72 h. The resin was filtered off and rinsed with d$^4$-MeOH (3×2 mL). After evaporation of the solvent, CH$_2$Cl$_2$ (3×2 mL) was added to eliminate the last traces of d$^4$-MeOH by co-evaporation. The mono-deuterated alcohol was obtained as a white solid after drying under vacuum (298 mg, 0.798 mmol, 68% yield, % D=98.7). LC-MS: 374 (M+1).

Step 4—Synthesis of 5-({p-[2-(5-ethylpyridin-2-yl)-2-oxoethoxy]phenyl}methyl)-(5-2H)-1,3-thiazolidine-2,4-dione

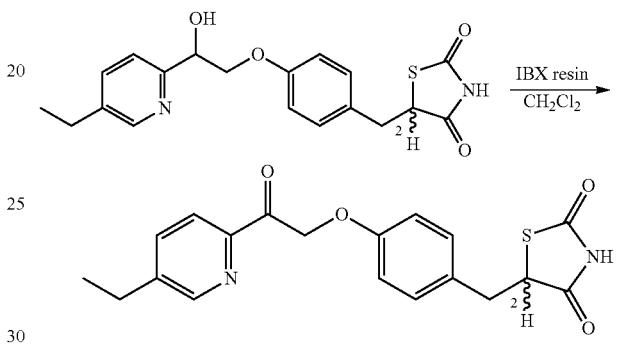

Mono-deuterated alcohol 5-({p-[2-(5-ethylpyridin-2-yl)-2-hydroxyethoxy]phenyl}methyl)-(5-$^2$H)-1,3-thiazolidine-2,4-dione (246.8 mg, 0.66 mmol) was suspended in 5 mL CH$_2$Cl$_2$, then added to a suspension of IBX-Resin (1.20 mmol/g, 2.203 g, 2.644 mmol, 4 equiv.) in 10 mL CH$_2$Cl$_2$. After shaking the reaction mixture at room temperature for 23 h, the resin was filtered and rinsed with CH$_2$Cl$_2$ (3×5 mL). After evaporation of the filtrate, the crude desired product was purified by flash chromatography on silica gel (Hexanes/EtOAc 95:5 to 1:1 v/v). 5-({p-[2-(5-Ethylpyridin-2-yl)-2-oxoethoxy]phenyl}methyl)-(5-$^2$H)-1,3-thiazolidine-2,4-dione was isolated as a white solid after evaporation of the pure fractions (166.5 mg, 0.448 mmol, 68% yield, % D=98.3). $^1$H NMR (300 MHz, DMSO-d$_6$) δ 12.02 (s, 0.69H), 8.62 (s, 1H), 7.90 (s, 2H), 7.14 (d, J=8.5 Hz), 6.87 (d, J=8.5 Hz), 5.65 (s, 2H), 3.30 (d, J=14.3 Hz), 3.03 (d, J=14.3 Hz), 2.73 (q, J=7.5 Hz), 1.22 (t, J=7.4 Hz), ~4.8 (m, residual proton at deuterium site, <0.1H); MS: [M+1]+=372

Example 2

Separation of (+)- and (−)-enantiomers of rac-5-({p-[2-(5-ethylpyridin-2-yl)-2-oxoethoxy]phenyl}methyl)-1,3-thiazolidine-2,4-dione rac-5-({p-[2-(5-Ethylpyridin-2-yl)-2-oxoethoxy]phenyl}methyl)-1,3-thiazolidine-2,4-dione (100.7 mg, 0.272 mmol) was dissolved in 25 mL of methanol. The enantiomers (2 mL per run) were separated by supercritical fluid chromatography using a ChiralCel OJ column (20×250 mm) and a mobile phase of 40% 2-propanol in carbon dioxide (CO$_2$). Peaks were detected by their UV signal at 254 nm. The fractions containing each enantiomer were pooled and evaporated. Purity and enantiomeric excess (% ee) were determined by supercritical fluid chromatography using an analytical ChiralCel OJ-H column (4.6×100 mm)

and the same mobile phase. Overall yield: 78.1 mg (0.211 mmol, 78%). Each enantiomer was characterized by measurement of its purity (UV, 254 nm), enantiomeric excess (% ee), optical rotation, and $^1$H NMR spectrum.

(+)-5-({p-[2-(5-Ethylpyridin-2-yl)-2-oxoethoxy]phenyl}methyl)-1,3-thiazolidine-2,4-dione 39.4 mg (0.106 mmol), 99.1% purity (UV, 254 nm), 98.2% ee; $^1$H NMR (300 MHz, $d_6$-DMSO) δ (ppm): 12.02 (s, 0.61H), 8.63 (s, 1H), 7.91 (s, 2H), 7.14 (d, 2H, J=8.8 Hz), 6.87 (d, 2H, J=8.8 Hz), 5.66 (s, 2H), 4.87 (dd, 1H, J=9.3 and 4.4 Hz), 3.31 (dd, 1H, J=15 and 4.4 Hz), 3.04 (dd, 1H, J=14 and 9.2 Hz), 2.74 (q, 2H, J=7.6 Hz), 1.23 (t, 3H, J=7.5 Hz); optical rotation $[α]_D$=+112.94 (c=0.5, acetonitrile, 21.7° C.).

(−)-5-({p-[2-(5-Ethylpyridin-2-yl)-2-oxoethoxy]phenyl}methyl)-1,3-thiazolidine-2,4-dione 38.7 mg (0.104 mmol), 99.7% purity (UV, 254 nm), 99.4% ee); $^1$H NMR (300 MHz, $d_6$-DMSO) δ (ppm): 12.02 (s, 0.6H), 8.63 (s, 1H), 7.91 (s, 2H), 7.14 (d, 2H, J=8.5 Hz), 6.87 (d, 2H, J=8.5 Hz), 5.66 (s, 2H), 4.87 (dd, 1H, J=9.3 and 4.4 Hz), 3.31 (dd, 1H, J=14.8 and 4.4 Hz), 3.04 (dd, 1H, J=14.1 and 9.2 Hz), 2.74 (q, 2H, J=7.6 Hz), 1.23 (t, 3H, J=7.5 Hz); optical rotation $[α]_D$=−117.15 (c=0.5, acetonitrile, 21.7° C.).

Example 3

Mouse and human plasma stability of (+)-(−)-5-({p-[2-(5-ethylpyridin-2-yl)-2-oxoethoxy]phenyl}methyl)-1,3-thiazolidine-2,4-dione, (−)-5-({p-[2-(5-ethylpyridin-2-yl)-2-oxoethoxy]phenyl}methyl)-1,3-thiazolidine-2,4-dione, and rac-5-({p-[2-(5-ethylpyridin-2-yl)-2-oxoethoxy]phenyl}methyl)-(5-$^2$H)-1,3-thiazolidine-2,4-dione (+)-5-({p-[2-(5-ethylpyridin-2-yl)-2-oxoethoxy]phenyl}methyl)-1,3-thiazolidine-2,4-dione, (−)-5-({p-[2-(5-ethylpyridin-2-yl)-2-oxoethoxy]phenyl}methyl)-1,3-thiazolidine-2,4-dione, rac-5-({p-[2-(5-ethylpyridin-2-yl)-2-oxoethoxy]phenyl}methyl)-(5-$^2$H))-1,3-thiazolidine-2,4-dione (>98% deuterium at C-5 of the 1,3-thiazolidine-2,4-dione moiety; 50:50 racemic mixture of (+)- and (−)- deuterated enantiomers) were incubated in CD-1 mouse plasma ($K_3$EDTA as anticoagulant) or human plasma ($K_3$EDTA as anticoagulant) at 37° C. in duplicates. Aliquots (50 µL) were removed at t=0, 0.0833, 0.25, 0.5, 1, 2, 4, 8, and 16 hours and added to micro centrifuge tubes containing 10 µL of 5% w/v zinc sulfate heptahydrate in water. Samples were frozen and stored until the study was complete. After thawing on ice, 10 µL of internal standard (ISTD) spiking solution ($d_4$-pioglitazone in acetonitrile/water 1:1) were added followed by 250 µL of methyl t-butyl ether (MTBE). A 100 µL aliquot of the organic layer was evaporated after homogeneization and reconstituted in 100 µL of 95:5 acetonitrile/0.1% formic acid in water (v/v).

The samples were analyzed semi-quantitatively by LC/MS-MS with elution on a chiral column (Daicel Chiral-Pak ID-3) for the separation of enantiomers (isocratic method of 5:95 v/v 0.1% formic acid in water and acetonitrile). Peak areas for the protonated and deuterated enantiomers were calculated and normalized to the area of the ISTD. Peak areas for the deuterated enantiomers (+)-5-({p-[2-(5-ethylpyridin-2-yl)-2-oxoethoxy]phenyl}methyl)-(5-2H)-1,3-thiazolidine-2,4-dione and (−)-5-({p-[2-(5-eth-ylpyridin-2-yl)-2-oxoethoxy]phenyl}methyl)-(5-$^2$H)-1,3-thiazolidine-2,4-dione were further corrected for the isotopic peak of the corresponding protonated enantiomer, (+)- and (−)-5-({p-[2-(5-ethylpyridin-2-yl)-2-oxoethoxy]phenyl}methyl)-1,3-thiazolidine-2,4-dione respectively, if present. Corrected data were analyzed and plotted using Microsoft Excel 2013 (Microsoft Corp, Redmond, Wash.) and the Excel Solver.

Scheme 3 illustrates the possible reactions in a solution of a deuterated racemate. The deuterium at the chiral center of both enantiomers, d+ and d−, can be depleted by D/H exchange to give both protonated enantiomers, h+ and h− with rate constants $k_{D++}$, $k_{D+−}$, $k_{D−+}$, $k_{D−−}$. At the same time, the protonated enantiomers h+ and h−, can exchange, with enantiomerization rate constants $k_{+−}$ and $k_{−+}$. All four compounds can also degrade with potentially different degradation rate constants $k_{h+d}$, $k_{h−d}$, $k_{d+d}$, $k_{d−d}$ for enantiomers h+, h−, d+, and d−, respectively.

SCHEME 3: Illustration of possible reactions and corresponding rate constants in a solution of rac-5-({p-[2-(5-ethylpyridin-2-yl)-2-oxoethoxy]phenyl}methyl)-(5-$^2$H)-1,3-thiazolidine-2,4-dione where d+, d−, h+, h− stand for (+)- and (−)-5-({p-[2-(5-ethylpyridin-2-yl)-2-oxoethoxy]phenyl}methyl)-(5-$^2$H)-1,3-thiazolidine-2,4-dione and (+)- and (−)-5-({p-[2-(5-ethylpyridin-2-yl)-2-oxoethoxy]phenyl}methyl)-1,3-thiazolidine-2,4-dione, respectively.

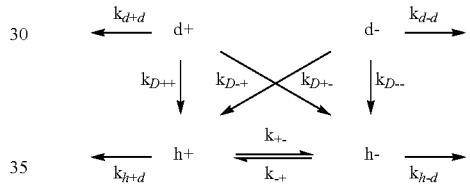

Human plasma stability data and mouse plasma stability data were analyzed independently. Concurrent analysis of the data for h+, h−, and deuterated racemate was performed. Calculated concentrations were obtained through numerical approximation of differential equations (1) and (2) for the stability studies of h+ and h− and equations (3) to (6) for the stability study of deuterated racemate (50:50 d+:d−) by the Euler method (equation (7)). The step between calculated time points was minimized in order to minimize the local error (proportional to the square of the step size) and the global error (proportional to the step size). To limit the complexity of calculations, the assumption was made that degradation was not affected by the isotopic substitution or the chirality, hence $k_{h+d}=k_{h−d}=k_{d+d}=k_{d−d}=k_d$. Data analysis was performed in Microsoft Excel 2013, using the Solver Generalized Reduced Gradient Nonlinear method with central derivatives to minimize the sum of sums of weighted $Δ^2$, square of difference between ISTD-normalized experimental data and calculated value, divided by the calculated value.

Equations 1-6

$$\frac{d[h+]}{dt} = -(k_{+−} + k_d)[h+] + k_{−+}[h−]$$

$$\frac{d[h−]}{dt} = k_{+−}[h+] - (k_{−+} + k_d)[h−]$$

$$\frac{d[h+]}{dt} = -(k_{+−} + k_d)[h+] + k_{−+}[h−] + k_{D++}[d+] + k_{D−+}[d−]$$

-continued $$\frac{d[h-]}{dt} = k_{+-}[h+] - (k_{-+} + k_d)[h-] + k_{D+-}[d+] + k_{D--}[d-]$$

$$\frac{d[d+]}{dt} = -(k_{D++} + k_{D+-} + k_d)[d+]$$

$$\frac{d[d-]}{dt} = -(k_{D--} + k_{D-+} + k_d)[d-]$$

where [h+], [h−], [d+], [d−] are the concentrations on both protonated and deuterated enantiomers, $k_{+-}$ and $k_{-+}$ are the rate constants for the enantiomerization reactions h+ to h− and h− to h+ respectively, $k_{D++}$, $k_{D+-}$, $k_{D-+}$, and $k_{D--}$ are the rate constants for the D/H exchange reactions d+ or d− to h+ or h−, and $k_d$ is the rate constant for the degradation of all four compounds.

$$[X]_{t2} = [X]_{t1} + (t_2 - t_1)[d[X]]_{t1} \quad \text{Equation 7}$$

where $[X]_{ti}$ is the concentration of either enantiomer at time ti, t1 is a time at which [X] is known, t2 is a time at which [X] is calculated, and $[d[X]]_{t1}$ is the calculated value of the differential equation at time t1.

Figure 2:
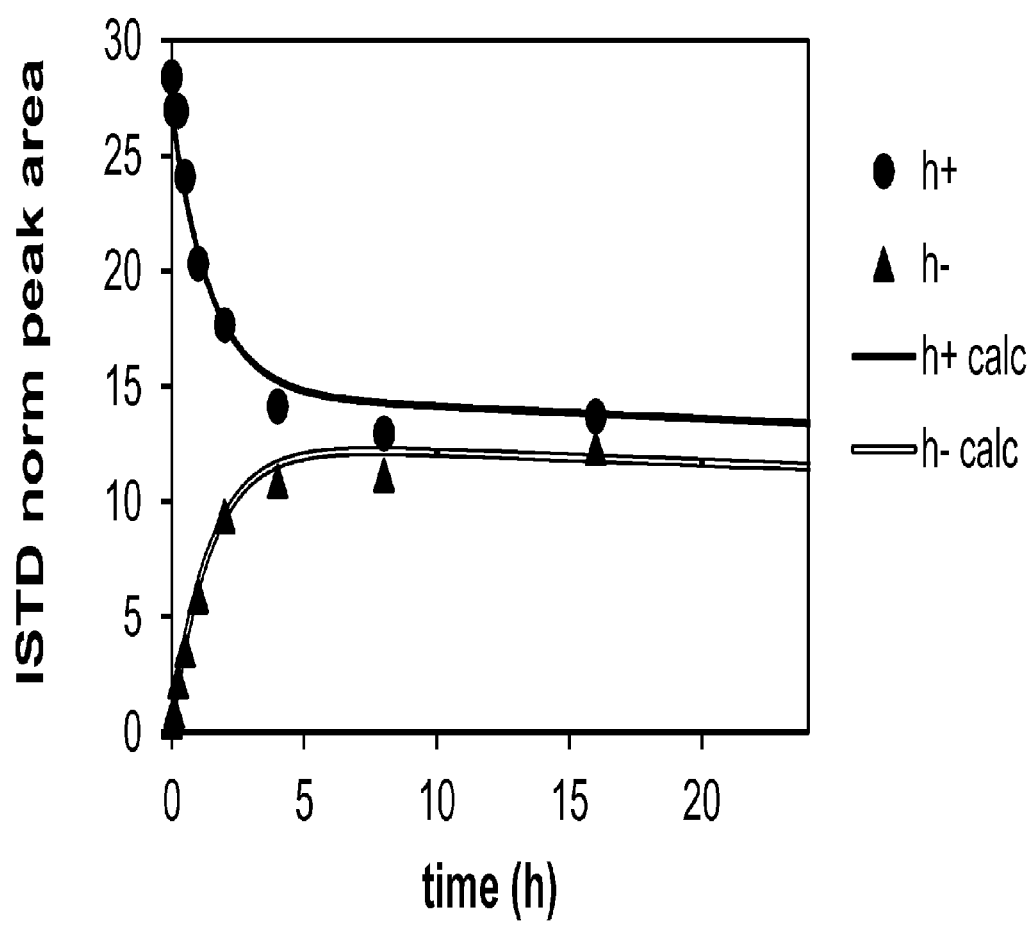
FIG. 2 is a graph showing in vitro stability data for (+)-5-({p-[2-(5-ethylpyridin-2-yl)-2-oxoethoxy]phenyl}methyl)-1,3-thiazolidine-2,4-dione (designated "h+") in human plasma, as described in Example 3, where the abbreviation "calc" indicates results from fitting experimental data to kinetic differential equations.
Figure 3:
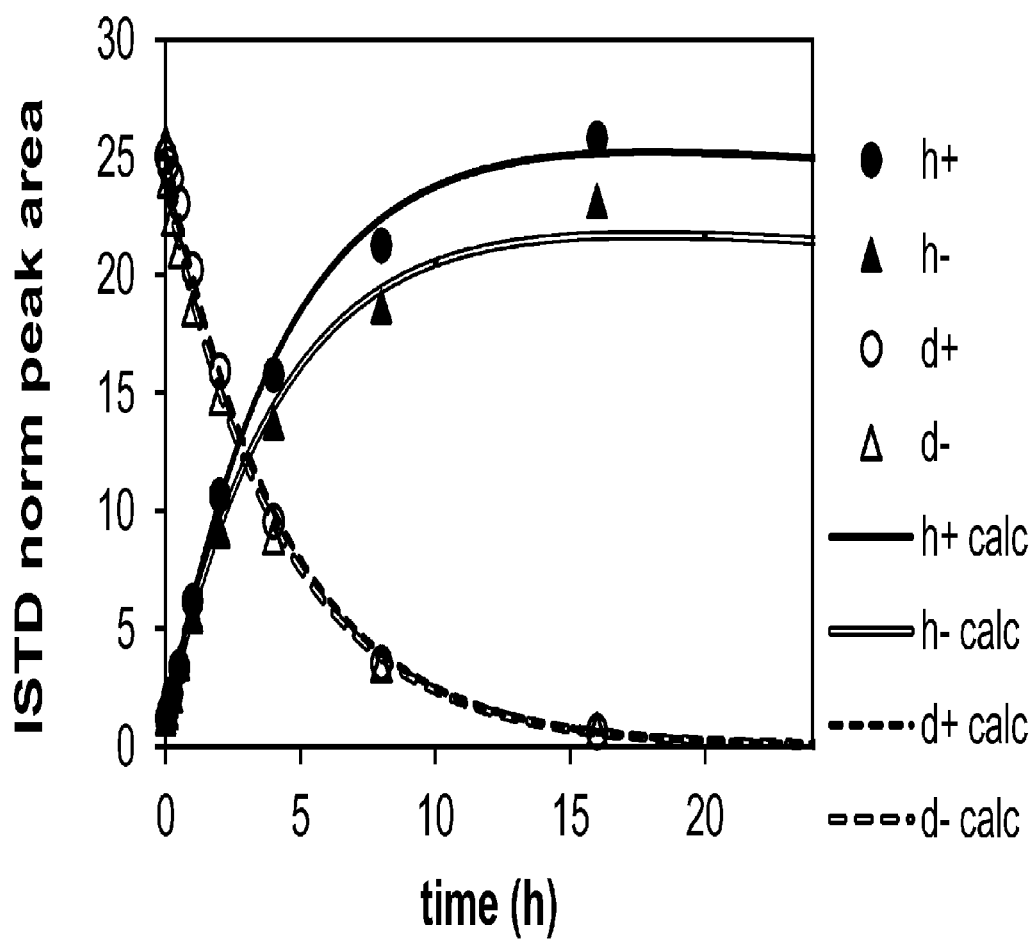
FIG. 3 is a graph showing in vitro stability data for rac-5-({p-[2-(5-ethylpyridin-2-yl)-2-oxoethoxy]phenyl}methyl)-(5-$^2$H)-1,3-thiazolidine-2,4-dione (which is a mixture of the (−)-deuterated enantiomer (i.e., "d−") and (+)-deuterated enantiomer (i.e., "d+") and which is designated "d-rac") in human plasma, as described in Example 3. The abbreviation "calc" indicates results from fitting experimental data to kinetic differential equations.
Figure 4:
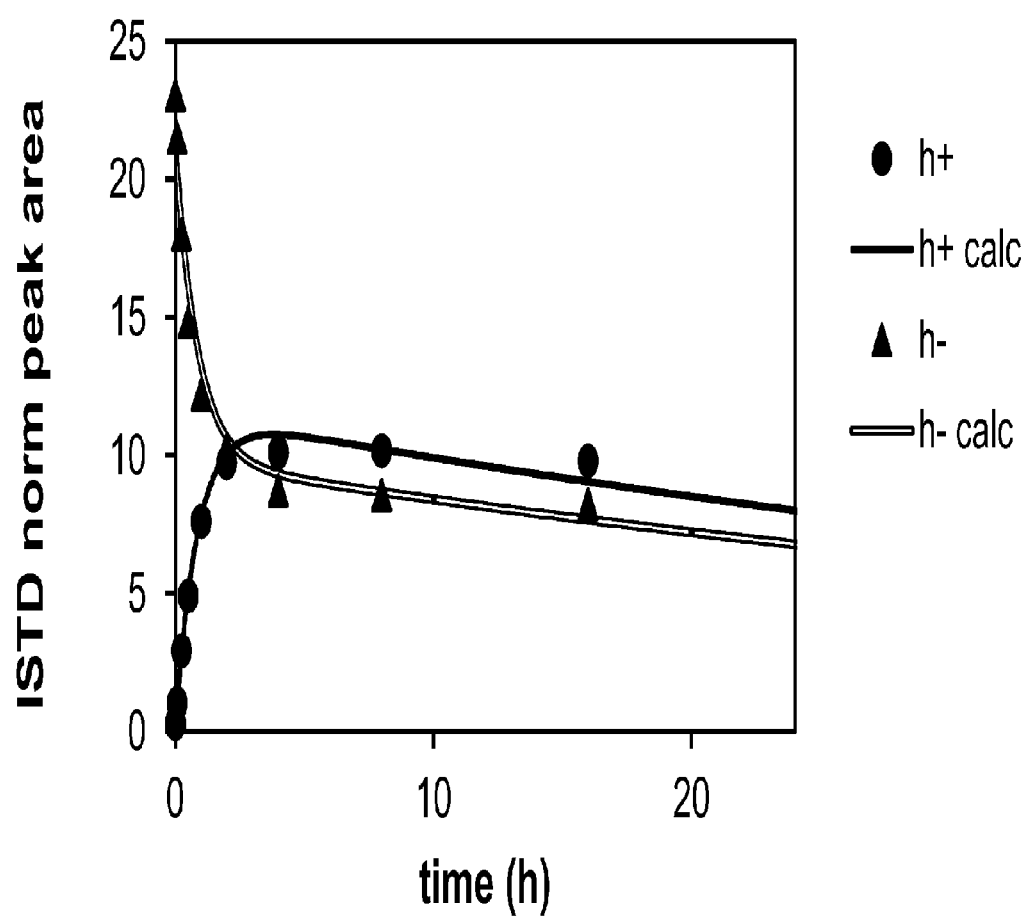
FIG. 4 is a graph showing in vitro stability data for (−)-5-({p-[2-(5-ethylpyridin-2-yl)-2-oxoethoxy]phenyl}methyl)-1,3-thiazolidine-2,4-dione (designated "h-") in mouse plasma, as described in Example 3, where the abbreviation "calc" indicates results from fitting experimental data to kinetic differential equations.
Figure 5:
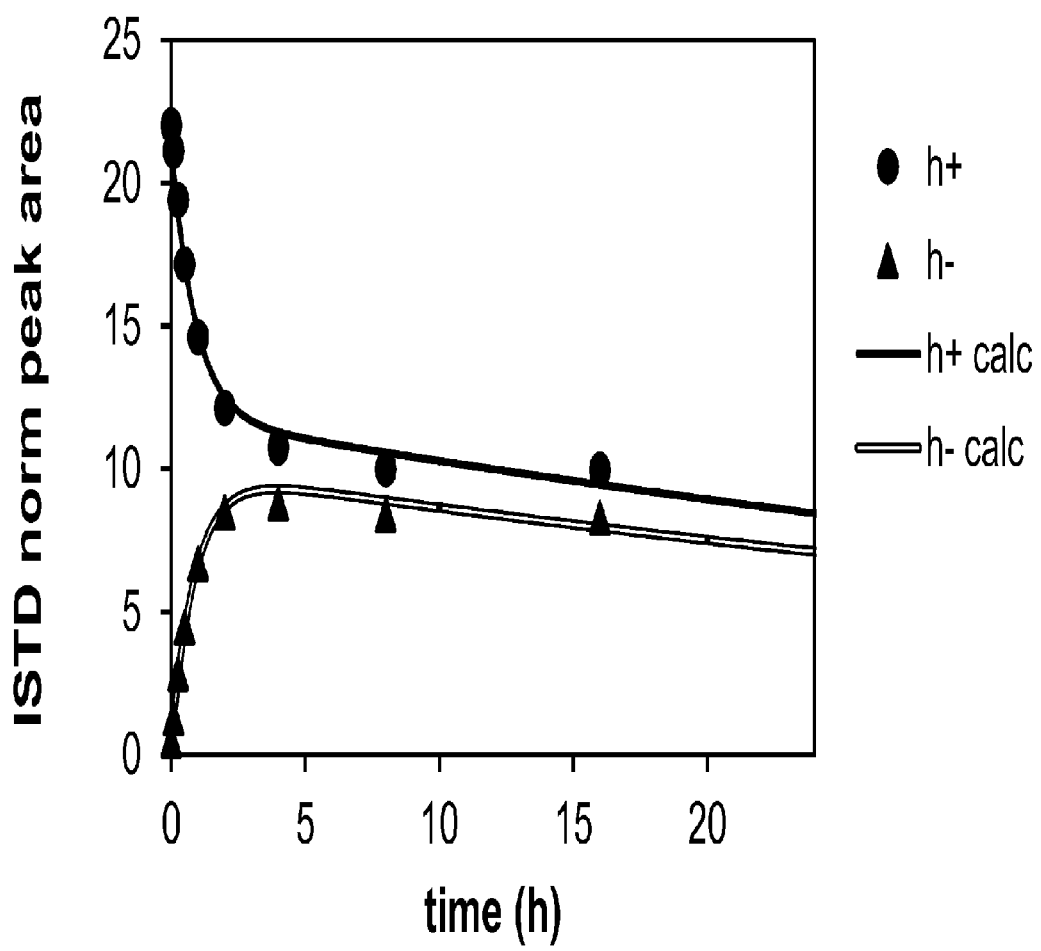
FIG. 5 is a graph showing in vitro stability data for (+)-5-({p-[2-(5-ethylpyridin-2-yl)-2-oxoethoxy]phenyl}methyl)-1,3-thiazolidine-2,4-dione (designated "h+") in mouse plasma, as described in Example 3, where the abbreviation "calc" indicates results from fitting experimental data to kinetic differential equations.
Figure 6:
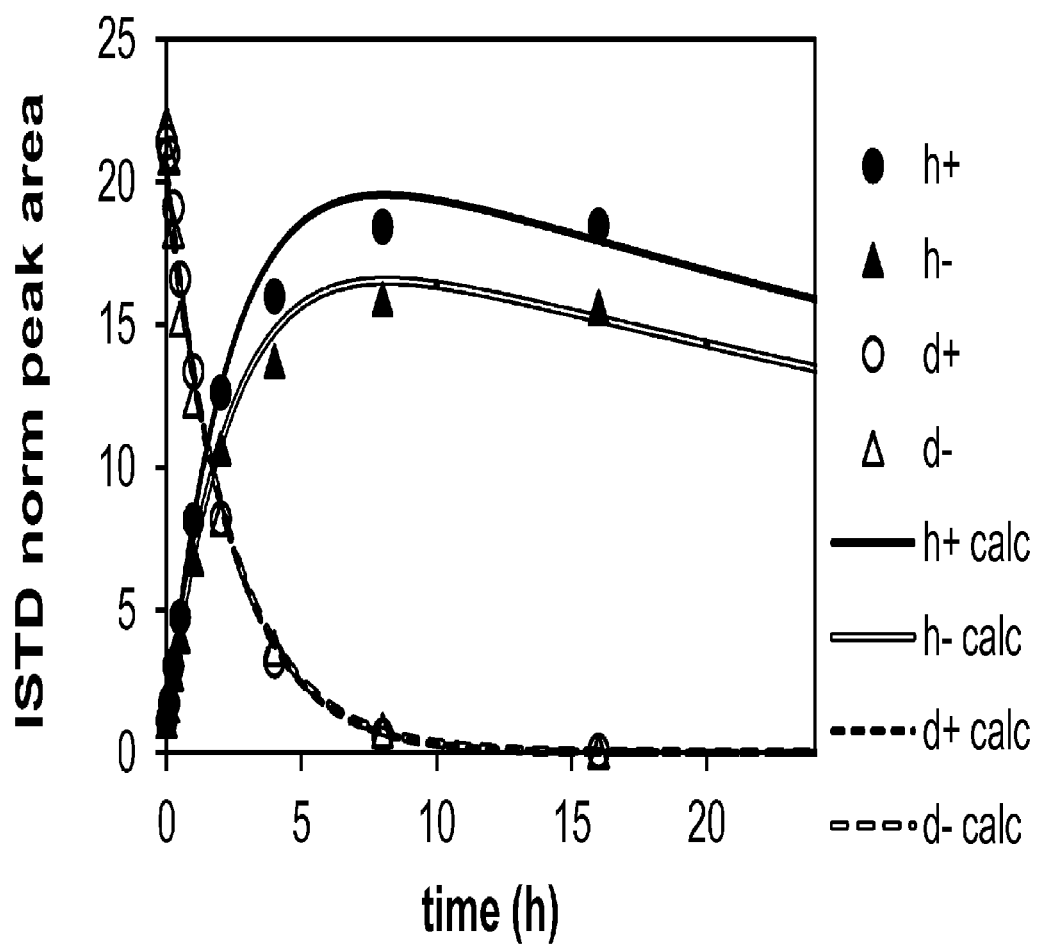
FIG. 6 is a graph showing in vitro stability data for rac-5-({p-[2-(5-ethylpyridin-2-yl)-2-oxoethoxy]phenyl}methyl)-(5-$^2$H)-1,3-thiazolidine-2,4-dione (which is a mixture of the (−)-deuterated enantiomer (i.e., "d−") and (+)-deuterated enantiomer (i.e., "d+") and which is designated "d-rac") in mouse plasma, as described in Example 3. The abbreviation "calc" indicates results from fitting experimental data to kinetic differential equations.

The observed and fitted data are shown in FIGS. 1-3 for human plasma experiments. The observed and fitted data are shown in FIGS. 4-6 for mouse plasma experiments. Fitted parameters are presented in Table 55 below.

Deuterium at the chiral center significantly improved stability against racemization. Indeed, the deuterium/proton exchange half-life is about 3 times longer than the racemization half-life (one half of the enantiomerization half-life reported in Table 55) of the protonated enantiomers h+ and h− irrespective of species.

TABLE 55

Rate constants and calculated half-lives ($t_{1/2}$) for the in vitro stability of h+, h−, and d-rac in human and mouse plasma at 37° C. obtained by fitting experimental data to Equations 1 to 6.

| Species | | D++ | D+− | D−+ | D−− | +− | −+ | d |
|---|---|---|---|---|---|---|---|---|
| human | k (h⁻¹) | 0.022 | 0.203 | 0.217 | 0.00915 | 0.308 | 0.359 | 0.00377 |
| | $t_{1/2}$ (h) | 3.1 | | 3.1 | | 2.2 | 1.9 | 184 |
| mouse | k (h⁻¹) | 0.0450 | 0.361 | 0.391 | <0.0001 | 0.504 | 0.594 | 0.0153 |
| | $t_{1/2}$ (h) | 1.7 | | | 1.8 | 1.4 | 1.2 | 45.4 |

INCORPORATION BY REFERENCE

All references listed herein are individually incorporated in their entirety by reference.

EQUIVALENTS

Numerous modifications and variations of the invention are possible in light of the above teachings. It is therefore to be understood that within the scope of the appended claims, the invention may be practiced otherwise that as specifically described herein.

The invention claimed is:

1. A pharmaceutical composition comprising a pharmaceutically acceptable carrier and a deuterium-enriched compound of Formula II or VII or a stereoisomer or pharmaceutically acceptable salt form of any of the foregoing, wherein Formula II is represented by:

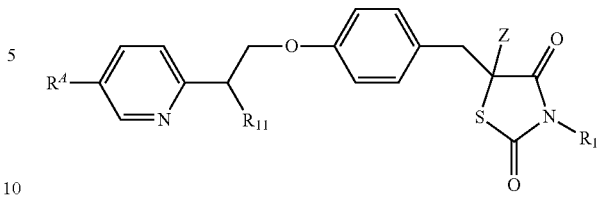

wherein:
 $R^1$ is selected from H and D;
 Z is H or D, provided that the abundance of deuterium in Z is at least 30%;
 $R^A$ is $C_{1-6}$ alkyl; and
 $R^{11}$ is selected from OH and OD; and
Formula VII is represented by:

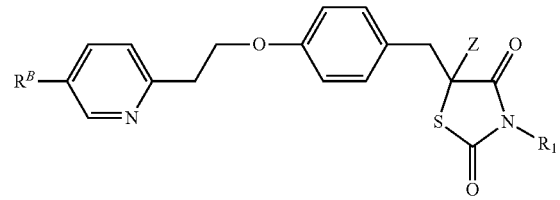

wherein:
 $R^1$ is selected from H and D;
 Z is H or D, provided that the abundance of deuterium in Z is at least 30%;
 $R^B$ is selected from $CH_3C(O)$—, $CH_3CH(OR)$—, and —$CH_2CO_2H$; and
 R is selected from H and D.

2. The pharmaceutical composition of claim 1, wherein the deuterium-enriched compound is a deuterium-enriched compound of Formula II or a stereoisomer or pharmaceutically acceptable salt form thereof.

3. The pharmaceutical composition of claim 1, wherein the deuterium-enriched compound is

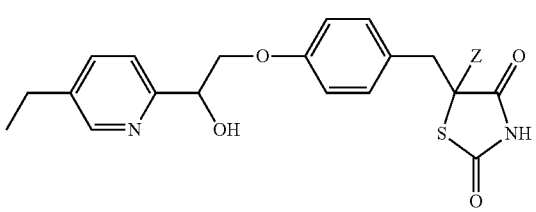

or a stereoisomer thereof or pharmaceutically acceptable salt form thereof; wherein Z is H or D, provided that the abundance of deuterium in Z is at least 30%.

4. The pharmaceutical composition of claim 1, wherein the deuterium-enriched compound is

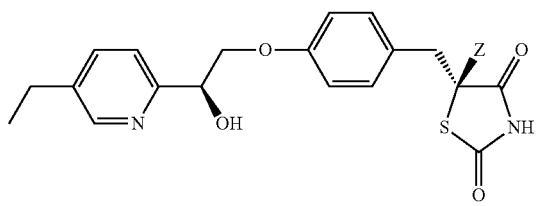

or a pharmaceutically acceptable salt form thereof; wherein Z is H or D, provided that the abundance of deuterium in Z is at least 30%.

5. The pharmaceutical composition of claim 1, wherein the deuterium-enriched compound is

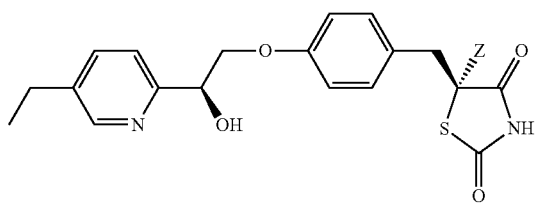

or a pharmaceutically acceptable salt form thereof; wherein Z is H or D, provided that the abundance of deuterium in Z is at least 30%.

6. The pharmaceutical composition of claim 1, wherein the deuterium-enriched compound is

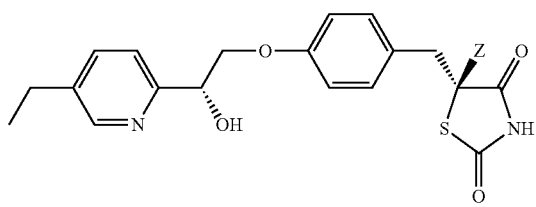

or a pharmaceutically acceptable salt form thereof; wherein the compound has an enantiomeric excess, with respect to the C-Z carbon, of at least 90%, and Z is H or D, provided that the abundance of deuterium in Z is at least 30%.

7. The pharmaceutical composition of claim 1, wherein the deuterium-enriched compound is

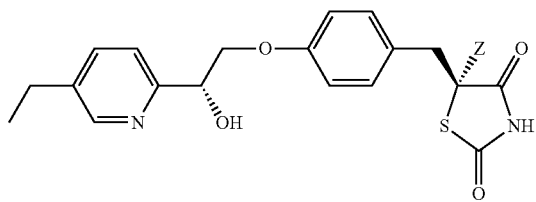

or a pharmaceutically acceptable salt form thereof; wherein the compound has an enantiomeric excess, with respect to the C-Z carbon, of at least 90%, and Z is H or D, provided that the abundance of deuterium in Z is at least 30%.

8. The pharmaceutical composition of claim 1, wherein the deuterium-enriched compound is a deuterium-enriched compound of Formula VII or a stereoisomer or pharmaceutically acceptable salt form thereof.

9. The pharmaceutical composition of claim 8, wherein $R^B$ is $CH_3C(O)$—.

10. The pharmaceutical composition of claim 8, wherein $R^B$ is $CH_3CH(OR)$—.

11. The pharmaceutical composition of claim 8, wherein $R^B$ is —$CH_2CO_2H$.

12. The pharmaceutical composition of claim 1, wherein the deuterium-enriched compound is

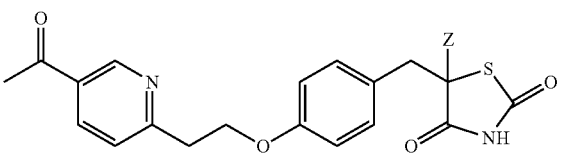

or a stereoisomer or pharmaceutically acceptable salt form thereof; wherein Z is H or D, provided that the abundance of deuterium in Z is at least 30%.

13. The pharmaceutical composition of claim 1, wherein the deuterium-enriched compound is

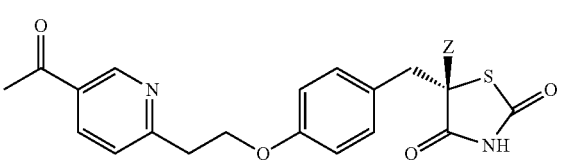

or a pharmaceutically acceptable salt form thereof; wherein the compound has an enantiomeric excess, with respect to the C-Z carbon, of at least 90%, and Z is H or D, provided that the abundance of deuterium in Z is at least 30%.

14. The pharmaceutical composition of claim 1, wherein the deuterium-enriched compound is

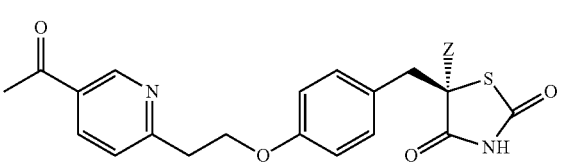

or a pharmaceutically acceptable salt form thereof; wherein the compound has an enantiomeric excess, with respect to the C-Z carbon, of at least 90%, and Z is H or D, provided that the abundance of deuterium in Z is at least 30%.

15. The pharmaceutical composition of claim 1, wherein the deuterium-enriched compound is

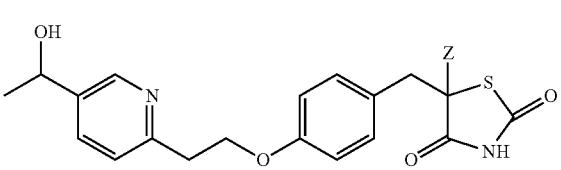

or a stereoisomer or pharmaceutically acceptable salt form thereof; wherein Z is H or D, provided that the abundance of deuterium in Z is at least 30%.

16. The pharmaceutical composition of claim 1, wherein the deuterium-enriched compound is

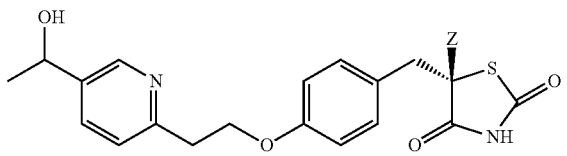

or a pharmaceutically acceptable salt form thereof; wherein the compound has an enantiomeric excess, with respect to the C-Z carbon, of at least 90%, and Z is H or D, provided that the abundance of deuterium in Z is at least 30%.

17. The pharmaceutical composition of claim 1, wherein the deuterium-enriched compound is

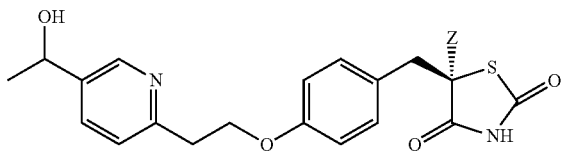

or a pharmaceutically acceptable salt form thereof; wherein the compound has an enantiomeric excess, with respect to the C-Z carbon, of at least 90%, and Z is H or D, provided that the abundance of deuterium in Z is at least 30%.

18. The pharmaceutical composition of claim 1, wherein the deuterium-enriched compound is

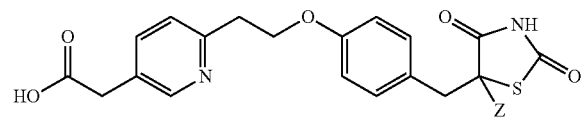

or a stereoisomer or pharmaceutically acceptable salt form thereof; wherein Z is H or D, provided that the abundance of deuterium in Z is at least 30%.

19. The pharmaceutical composition of claim 1, wherein the deuterium-enriched compound is

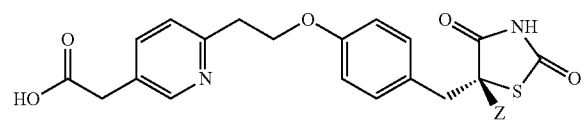

or a pharmaceutically acceptable salt form thereof; wherein the compound has an enantiomeric excess, with respect to the C-Z carbon, of at least 90%, and Z is H or D, provided that the abundance of deuterium in Z is at least 30%.

20. The pharmaceutical composition of claim 1, wherein the deuterium-enriched compound is

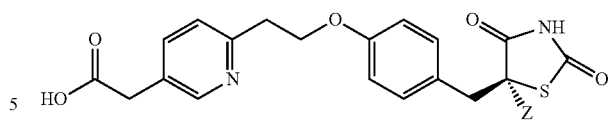

or a pharmaceutically acceptable salt form thereof; wherein the compound has an enantiomeric excess, with respect to the C-Z carbon, of at least 90%, and Z is H or D, provided that the abundance of deuterium in Z is at least 30%.

21. The pharmaceutical composition of claim 2, wherein the abundance of deuterium in Z is at least 90%.

22. The pharmaceutical composition of claim 9, wherein the abundance of deuterium in Z is at least 90%.

23. The pharmaceutical composition of claim 10, wherein the abundance of deuterium in Z is at least 90%.

24. The pharmaceutical composition of claim 11, wherein the abundance of deuterium in Z is at least 90%.

25. The pharmaceutical composition of claim 12, wherein the abundance of deuterium in Z is at least 90%.

26. The pharmaceutical composition of claim 14, wherein the abundance of deuterium in Z is at least 90%.

27. The pharmaceutical composition of claim 14, wherein the abundance of deuterium in Z is at least 95%.

28. The pharmaceutical composition of claim 15, wherein the abundance of deuterium in Z is at least 90%.

29. The pharmaceutical composition of claim 17, wherein the abundance of deuterium in Z is at least 90%.

30. The pharmaceutical composition of claim 17, wherein the abundance of deuterium in Z is at least 95%.

31. The pharmaceutical composition of claim 18, wherein the abundance of deuterium in Z is at least 90%.

32. The pharmaceutical composition of claim 19, wherein the abundance of deuterium in Z is at least 90%.

33. The pharmaceutical composition of claim 26, wherein the compound has an enantiomeric excess, with respect to the C-Z carbon, of at least 95%.

34. The pharmaceutical composition of claim 27, wherein the compound has an enantiomeric excess, with respect to the C-Z carbon, of at least 95%.

35. The pharmaceutical composition of claim 29, wherein the compound has an enantiomeric excess, with respect to the C-Z carbon, of at least 95%.

36. The pharmaceutical composition of claim 30, wherein the compound has an enantiomeric excess, with respect to the C-Z carbon, of at least 95%.

37. A dosage form selected from the group consisting of a tablet, caplet, and capsule, wherein the dosage form comprises a pharmaceutical composition of claim 2.

38. A dosage form selected from the group consisting of a tablet, caplet, and capsule, wherein the dosage form comprises a pharmaceutical composition of claim 8.

39. A dosage form selected from the group consisting of a tablet, caplet, and capsule, wherein the dosage form comprises a pharmaceutical composition of claim 26.

40. A dosage form selected from the group consisting of a tablet, caplet, and capsule, wherein the dosage form comprises a pharmaceutical composition of claim 29.

41. A method of treating a disease selected from the group consisting of Type I diabetes, Type II diabetes, insulin resistance, and inadequate tolerance, comprising administering to a patient in need thereof a therapeutically effective amount a pharmaceutical composition of claim 1 to treat the disease.

42. The method of claim 41, wherein the disease is Type II diabetes.

* * * * *